United States Patent
Shi et al.

(10) Patent No.: US 12,404,323 B2
(45) Date of Patent: *Sep. 2, 2025

(54) ANTIBODY CAPABLE OF BINDING TO THYMIC STROMAL LYMPHOPOIETIN AND USE THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Jinping Shi, Shanghai (CN); Hua Ying, Shanghai (CN); Tingting Li, Shanghai (CN); Yifang Wang, Shanghai (CN); Guimei Yang, Shanghai (CN); Hu Ge, Shanghai (CN); Weikang Tao, Shanghai (CN)

(73) Assignees: JIANGSU HENGRUI MEDICINE CO., LTD, Lianyungang (CN); SHANGHAI HENGRUI PHARMACEUTICAL CO., LTD, Shanghai (CN)

(*) Notice: Subject to any disclaimer, the term of this patent is extended or adjusted under 35 U.S.C. 154(b) by 645 days.

This patent is subject to a terminal disclaimer.

(21) Appl. No.: 17/615,970

(22) PCT Filed: Jun. 3, 2020

(86) PCT No.: PCT/CN2020/094154
§ 371 (c)(1),
(2) Date: Dec. 2, 2021

(87) PCT Pub. No.: WO2020/244544
PCT Pub. Date: Dec. 10, 2020

(65) Prior Publication Data
US 2022/0340654 A1  Oct. 27, 2022

(30) Foreign Application Priority Data

Jun. 4, 2019  (CN) .......................... 201910480579.9

(51) Int. Cl.
*A61K 39/00*  (2006.01)
*A61K 39/395*  (2006.01)
*A61P 11/06*  (2006.01)
*C07K 16/24*  (2006.01)

(52) U.S. Cl.
CPC .............. *C07K 16/24* (2013.01); *A61P 11/06* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 12,202,891 B2* | 1/2025 | Shi | ............. A61P 11/06 |
| 2009/0130119 A1 | 5/2009 | Abate et al. | |
| 2017/0066823 A1 | 3/2017 | Edwards et al. | |
| 2017/0247460 A1 | 8/2017 | Geiger et al. | |
| 2020/0176515 A1 | 6/2020 | Andya et al. | |
| 2022/0144937 A1 | 5/2022 | Wu et al. | |
| 2023/0120270 A1 | 4/2023 | Ying et al. | |
| 2024/0016931 A1* | 1/2024 | Wang | ............. A61K 47/186 |

FOREIGN PATENT DOCUMENTS

| | | |
|---|---|---|
| CN | 101084015 A | 12/2007 |
| CN | 101193917 A | 6/2008 |
| CN | 101389657 A | 3/2009 |
| CN | 101605814 A | 12/2009 |
| CN | 103861102 A | 6/2014 |
| CN | 106474470 A | 3/2017 |
| CN | 107073113 A | 8/2017 |
| CN | 109206517 A | 1/2019 |
| CN | 110538321 A | 12/2019 |
| CN | 111375059 A | 7/2020 |
| WO | 2008155365 A1 | 12/2008 |
| WO | 2009035577 A1 | 3/2009 |
| WO | 2011056772 A1 | 5/2011 |
| WO | 2014031718 A1 | 2/2014 |
| WO | 2016142426 A1 | 9/2016 |
| WO | 2017004149 A1 | 1/2017 |

(Continued)

OTHER PUBLICATIONS

Casale TB. Biologics and biomarkers for asthma, urticaria, and nasal polyposis. Journal of Allergy and Clinical Immunology. 139(5):1411-1421, 2017. (Year: 2017).*
Gauvreau et al. Effects of an anti-TSLP antibody on allergen-induced asthmatic responses. Randomized Controlled Trial N Engl J Med. May 29, 2014;370(22):2102-10. (Year: 2014).*
U.S. Appl. No. 18/607,180, filed Mar. 15, 2024.
Gavreau Gail M et al: "Effects of an anti-TSLP antibody on allergen-induced asthmatic responses", New England Journal of Medicine, vol. 370, No. 22, May 24, 2014, pp. 2102-2110, XP009189903.
Menzies-Gow Andrew et al: "Tezepelumab in Adults and Adolescents with Severe, Uncontrolled Asthma", The New England Journal of Medicine, vol. 384, No. 19, May 13, 2021, pp. 1800-1809, XP093180115.

(Continued)

*Primary Examiner* — Maher M Haddad
(74) *Attorney, Agent, or Firm* — Donald Huddler; Sean Brock

(57) ABSTRACT

Disclosed are an antibody capable of binding to thymic stromal lymphopoietin and the use thereof. Disclosed are an anti-TSLP antibody, comprising a murine antibody, chimeric antibody and humanized antibody of the light chain and heavy chain variable regions of the anti-TSLP antibody and antigen-binding fragments thereof, or a pharmaceutically acceptable salt or solvent compound thereof, and the use thereof as a medicament for treating asthma, especially the use thereof in the preparation of a drug for treating TSLP-positive diseases or conditions.

9 Claims, 5 Drawing Sheets

Specification includes a Sequence Listing.

(56) References Cited

FOREIGN PATENT DOCUMENTS

| WO | 2017042701 A1 | 3/2017 |
| WO | 2018191479 A1 | 10/2018 |
| WO | 2020200099 A1 | 10/2020 |
| WO | 2020244544 A1 | 12/2020 |
| WO | 2021139758 A1 | 7/2021 |
| WO | 2021163504 A1 | 8/2021 |

OTHER PUBLICATIONS

Gail M. Gauvreau, Ph.D. et al., "Effects of an Anti-TSLP Antibody on Allergen-Induced Asthmatic Responses", The New England Journal of Medicine (2014), vol. 370, No. 22, pp. 2102-2110 (9 pages).
International Search Report (English and Chinese) and Written Opinion of the ISA (Chinese) issued in PCT/CN2021/132037, mailed Feb. 17, 2022; ISA/CN.

* cited by examiner

SEQUENCE LISTING

```
<160> NUMBER OF SEQ ID NOS: 146

<210> SEQ ID NO 1
<211> LENGTH: 176
<212> TYPE: PRT
<213> ORGANISM: Artificial Sequence
<220> FEATURE:
<223> OTHER INFORMATION: Synthetic Sequence_Amino acid sequence of his-
      tagged human TSLP antigen (huTSLP-his)

<400> SEQUENCE: 1

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
                20                  25                  30

Asn Cys Asp Phe Glu Lys Ile Lys Ala Ala Tyr Leu Ser Thr Ile Ser
            35                  40                  45

Lys Asp Leu Ile Thr Tyr Met Ser Gly Thr Lys Ser Thr Glu Phe Asn
        50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Ala Arg
        115                 120                 125

Lys Ser Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln Gly
145                 150                 155                 160

Ser Ser Asp Tyr Lys Asp Asp Asp Lys His His His His His
```

```
<210> SEQ ID NO 2
<211> LENGTH: 398
<212> TYPE: PRT
<213> ORGANISM: Artificial Sequence
<220> FEATURE:
<223> OTHER INFORMATION: Synthetic Sequence_Amino acid sequence of Fc-
      tagged human TSLP antigen (huTSLP-Fc)

<400> SEQUENCE: 2
```

| | | | | | | | | | | | | | | |
|---|---|---|---|---|---|---|---|---|---|---|---|---|---|---|
| Met | Phe | Pro | Phe | Ala | Leu | Leu | Tyr | Val | Leu | Ser | Val | Ser | Phe | Arg | Lys |
| 1 | | | | 5 | | | | | 10 | | | | | 15 | |
| Ile | Phe | Ile | Leu | Gln | Leu | Val | Gly | Leu | Val | Leu | Thr | Tyr | Asp | Phe | Thr |
| | | | 20 | | | | | 25 | | | | | 30 | | |
| Asn | Cys | Asp | Phe | Glu | Lys | Ile | Lys | Ala | Ala | Tyr | Leu | Ser | Thr | Ile | Ser |
| | | 35 | | | | | 40 | | | | | 45 | | | |
| Lys | Asp | Leu | Ile | Thr | Tyr | Met | Ser | Gly | Thr | Lys | Ser | Thr | Glu | Phe | Asn |
| 50 | | | | | 55 | | | | | 60 | | | | | |
| Asn | Thr | Val | Ser | Cys | Ser | Asn | Arg | Pro | His | Cys | Leu | Thr | Glu | Ile | Gln |
| 65 | | | | | 70 | | | | | 75 | | | | | 80 |
| Ser | Leu | Thr | Phe | Asn | Pro | Thr | Ala | Gly | Cys | Ala | Ser | Leu | Ala | Lys | Glu |
| | | | | 85 | | | | | 90 | | | | | 95 | |
| Met | Phe | Ala | Met | Lys | Thr | Lys | Ala | Ala | Leu | Ala | Ile | Trp | Cys | Pro | Gly |
| | | | 100 | | | | | 105 | | | | | 110 | | |
| Tyr | Ser | Glu | Thr | Gln | Ile | Asn | Ala | Thr | Gln | Ala | Met | Lys | Lys | Ala | Arg |
| | | 115 | | | | | 120 | | | | | 125 | | | |
| Lys | Ser | Lys | Val | Thr | Thr | Asn | Lys | Cys | Leu | Glu | Gln | Val | Ser | Gln | Leu |
| 130 | | | | | 135 | | | | | 140 | | | | | |
| Gln | Gly | Leu | Trp | Arg | Arg | Phe | Asn | Arg | Pro | Leu | Leu | Lys | Gln | Gln | Asp |
| 145 | | | | | 150 | | | | | 155 | | | | | 160 |
| Ile | Glu | Gly | Arg | Met | Asp | Glu | Pro | Lys | Ser | Ser | Asp | Lys | Thr | His | Thr |
| | | | | 165 | | | | | 170 | | | | | 175 | |
| Cys | Pro | Pro | Cys | Pro | Ala | Pro | Glu | Leu | Leu | Gly | Gly | Pro | Ser | Val | Phe |
| | | | | 180 | | | | | 185 | | | | | 190 | |
| Leu | Phe | Pro | Pro | Lys | Pro | Lys | Asp | Thr | Leu | Met | Ile | Ser | Arg | Thr | Pro |
| | | | 195 | | | | | 200 | | | | | 205 | | |
| Glu | Val | Thr | Cys | Val | Val | Val | Asp | Val | Ser | His | Glu | Asp | Pro | Glu | Val |
| 210 | | | | | 215 | | | | | 220 | | | | | |
| Lys | Phe | Asn | Trp | Tyr | Val | Asp | Gly | Val | Glu | Val | His | Asn | Ala | Lys | Thr |
| 225 | | | | | 230 | | | | | 235 | | | | | 240 |
| Lys | Pro | Arg | Glu | Glu | Gln | Tyr | Asn | Ser | Thr | Tyr | Arg | Val | Val | Ser | Val |
| | | | | 245 | | | | | 250 | | | | | 255 | |
| Leu | Thr | Val | Leu | His | Gln | Asp | Trp | Leu | Asn | Gly | Lys | Glu | Tyr | Lys | Cys |
| | | | 260 | | | | | 265 | | | | | 270 | | |
| Lys | Val | Ser | Asn | Lys | Ala | Leu | Pro | Ala | Pro | Ile | Glu | Lys | Thr | Ile | Ser |
| | | 275 | | | | | 280 | | | | | 285 | | | |
| Lys | Ala | Lys | Gly | Gln | Pro | Arg | Glu | Pro | Gln | Val | Tyr | Thr | Leu | Pro | Pro |
| | | 290 | | | | | 295 | | | | | 300 | | | |
| Ser | Arg | Asp | Glu | Leu | Thr | Lys | Asn | Gln | Val | Ser | Leu | Thr | Cys | Leu | Val |
| 305 | | | | | 310 | | | | | 315 | | | | | 320 |
| Lys | Gly | Phe | Tyr | Pro | Ser | Asp | Ile | Ala | Val | Glu | Trp | Glu | Ser | Asn | Gly |
| | | | | 325 | | | | | 330 | | | | | 335 | |
| Gln | Pro | Glu | Asn | Asn | Tyr | Lys | Thr | Thr | Pro | Pro | Val | Leu | Asp | Ser | Asp |
| | | | 340 | | | | | 345 | | | | | 350 | | |

Gly Ser Phe Phe Leu Tyr Ser Lys Leu Thr Val Asp Lys Ser Arg Trp
            355                 360                 365

Gln Gln Gly Asn Val Phe Ser Cys Ser Val Met His Glu Ala Leu His
        370                 375                 380

Asn His Tyr Thr Gln Lys Ser Leu Ser Leu Ser Pro Gly Lys
385                 390                 395

<210> SEQ ID NO 3
<211> LENGTH: 168
<212> TYPE: PRT
<213> ORGANISM: Artificial Sequence
<220> FEATURE:
<223> OTHER INFORMATION: Synthetic Sequence_Amino acid sequence of his-
    tagged cyno TSLP antigen (cynoTSLP-his)

<400> SEQUENCE: 3

Met Glu Thr Asp Thr Leu Leu Leu Trp Val Leu Leu Leu Trp Val Pro
1               5                   10                  15

Gly Ser Thr Gly Tyr Asp Phe Thr Asn Cys Asp Phe Gln Lys Ile Glu
            20                  25                  30

Ala Asp Tyr Leu Arg Thr Ile Ser Lys Asp Leu Ile Thr Tyr Met Ser
        35                  40                  45

Gly Thr Lys Ser Thr Asp Phe Asn Asn Thr Val Ser Cys Ser Asn Arg
    50                  55                  60

Pro His Cys Leu Thr Glu Ile Gln Ser Leu Thr Phe Asn Pro Thr Pro
65                  70                  75                  80

Arg Cys Ala Ser Leu Ala Lys Glu Met Phe Ala Arg Lys Thr Lys Ala
                85                  90                  95

Thr Leu Ala Leu Trp Cys Pro Gly Tyr Ser Glu Thr Gln Ile Asn Ala
            100                 105                 110

Thr Gln Ala Met Lys Lys Ala Arg Lys Ser Lys Val Thr Thr Asn Lys
        115                 120                 125

Cys Leu Glu Gln Val Ser Gln Leu Leu Gly Leu Trp Arg Arg Phe Ile
    130                 135                 140

Arg Thr Leu Leu Lys Gln Gln Gly Ser Ser Asp Tyr Lys Asp Asp Asp
145                 150                 155                 160

Asp Lys His His His His His His
                165

<210> SEQ ID NO 4
<211> LENGTH: 390
<212> TYPE: PRT
<213> ORGANISM: Artificial Sequence
<220> FEATURE:
<223> OTHER INFORMATION: Synthetic Sequence_Amino acid sequence of Fc-
    tagged cyno TSLP antigen (cyno TSLP-Fc)

<400> SEQUENCE: 4

Met Glu Thr Asp Thr Leu Leu Leu Trp Val Leu Leu Leu Trp Val Pro
1               5                   10                  15

Gly Ser Thr Gly Tyr Asp Phe Thr Asn Cys Asp Phe Gln Lys Ile Glu
            20                  25                  30

Ala Asp Tyr Leu Arg Thr Ile Ser Lys Asp Leu Ile Thr Tyr Met Ser
        35                  40                  45

Gly Thr Lys Ser Thr Asp Phe Asn Asn Thr Val Ser Cys Ser Asn Arg
    50                  55                  60

Pro His Cys Leu Thr Glu Ile Gln Ser Leu Thr Phe Asn Pro Thr Pro
65                  70                  75                  80

```
Arg Cys Ala Ser Leu Ala Lys Glu Met Phe Ala Arg Lys Thr Lys Ala
                85                  90                  95
Thr Leu Ala Leu Trp Cys Pro Gly Tyr Ser Glu Thr Gln Ile Asn Ala
            100                 105                 110
Thr Gln Ala Met Lys Lys Ala Arg Lys Ser Lys Val Thr Thr Asn Lys
        115                 120                 125
Cys Leu Glu Gln Val Ser Gln Leu Leu Gly Leu Trp Arg Arg Phe Ile
    130                 135                 140
Arg Thr Leu Leu Lys Gln Gln Asp Ile Glu Gly Arg Met Asp Glu Pro
145                 150                 155                 160
Lys Ser Ser Asp Lys Thr His Thr Cys Pro Pro Cys Pro Ala Pro Glu
                165                 170                 175
Leu Leu Gly Gly Pro Ser Val Phe Leu Phe Pro Pro Lys Pro Lys Asp
            180                 185                 190
Thr Leu Met Ile Ser Arg Thr Pro Glu Val Thr Cys Val Val Val Asp
        195                 200                 205
Val Ser His Glu Asp Pro Glu Val Lys Phe Asn Trp Tyr Val Asp Gly
    210                 215                 220
Val Glu Val His Asn Ala Lys Thr Lys Pro Arg Glu Glu Gln Tyr Asn
225                 230                 235                 240
Ser Thr Tyr Arg Val Val Ser Val Leu Thr Val Leu His Gln Asp Trp
                245                 250                 255
Leu Asn Gly Lys Glu Tyr Lys Cys Lys Val Ser Asn Lys Ala Leu Pro
            260                 265                 270
Ala Pro Ile Glu Lys Thr Ile Ser Lys Ala Lys Gly Gln Pro Arg Glu
        275                 280                 285
Pro Gln Val Tyr Thr Leu Pro Pro Ser Arg Asp Glu Leu Thr Lys Asn
    290                 295                 300
Gln Val Ser Leu Thr Cys Leu Val Lys Gly Phe Tyr Pro Ser Asp Ile
305                 310                 315                 320
Ala Val Glu Trp Glu Ser Asn Gly Gln Pro Glu Asn Asn Tyr Lys Thr
                325                 330                 335
Thr Pro Pro Val Leu Asp Ser Asp Gly Ser Phe Phe Leu Tyr Ser Lys
            340                 345                 350
Leu Thr Val Asp Lys Ser Arg Trp Gln Gln Gly Asn Val Phe Ser Cys
        355                 360                 365
Ser Val Met His Glu Ala Leu His Asn His Tyr Thr Gln Lys Ser Leu
    370                 375                 380
Ser Leu Ser Pro Gly Lys
385                 390

<210> SEQ ID NO 5
<211> LENGTH: 446
<212> TYPE: PRT
<213> ORGANISM: Artificial Sequence
<220> FEATURE:
<223> OTHER INFORMATION: Synthetic Sequence_Amino acid sequence of Fc-
      tagged human TSLP receptor extracellular domain (human-TSLPR-Fc-
      ECD)

<400> SEQUENCE: 5

Gly Ala Ala Glu Gly Val Gln Ile Gln Ile Ile Tyr Phe Asn Leu Glu
1               5                   10                  15
Thr Val Gln Val Thr Trp Asn Ala Ser Lys Tyr Ser Arg Thr Asn Leu
            20                  25                  30
Thr Phe His Tyr Arg Phe Asn Gly Asp Glu Ala Tyr Asp Gln Cys Thr
```

```
              35                  40                  45
Asn Tyr Leu Leu Gln Glu Gly His Thr Ser Gly Cys Leu Leu Asp Ala
 50                  55                  60

Glu Gln Arg Asp Asp Ile Leu Tyr Phe Ser Ile Arg Asn Gly Thr His
 65                  70                  75                  80

Pro Val Phe Thr Ala Ser Arg Trp Met Val Tyr Leu Lys Pro Ser
                 85                  90                  95

Ser Pro Lys His Val Arg Phe Ser Trp His Gln Asp Ala Val Thr Val
                100                 105                 110

Thr Cys Ser Asp Leu Ser Tyr Gly Asp Leu Leu Tyr Glu Val Gln Tyr
                115                 120                 125

Arg Ser Pro Phe Asp Thr Glu Trp Gln Ser Lys Gln Glu Asn Thr Cys
    130                 135                 140

Asn Val Thr Ile Glu Gly Leu Asp Ala Glu Lys Cys Tyr Ser Phe Trp
145                 150                 155                 160

Val Arg Val Lys Ala Met Glu Asp Val Tyr Gly Pro Asp Thr Tyr Pro
                165                 170                 175

Ser Asp Trp Ser Glu Val Thr Cys Trp Gln Arg Gly Glu Ile Arg Asp
                180                 185                 190

Ala Cys Ala Glu Thr Pro Thr Pro Lys Pro Lys Leu Ser Lys Asp
                195                 200                 205

Ile Glu Gly Arg Met Asp Glu Pro Lys Ser Ser Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
    435                 440                 445

<210> SEQ ID NO 6
```

```
<211> LENGTH: 121
<212> TYPE: PRT
<213> ORGANISM: Mus musculus

<400> SEQUENCE: 6

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Asp
            20                  25                  30

Tyr Met Asn Trp Val Lys Gln Ser His Gly Lys Ser Leu Glu Trp Ile
        35                  40                  45

Gly Ile Ile Ser Pro Tyr Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Glu Asp Tyr Asp Tyr Asp Gly Tyr Ala Met Asp His Trp Gly
            100                 105                 110

Gln Gly Thr Ser Val Thr Val Ser Ser
        115                 120

<210> SEQ ID NO 7
<211> LENGTH: 105
<212> TYPE: PRT
<213> ORGANISM: Mus musculus

<400> SEQUENCE: 7

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Arg Thr Phe
                85                  90                  95

Gly Gly Gly Thr Lys Leu Glu Ile Lys
            100                 105

<210> SEQ ID NO 8
<211> LENGTH: 120
<212> TYPE: PRT
<213> ORGANISM: Mus musculus

<400> SEQUENCE: 8

Gln Ala Tyr Leu Gln Gln Ser Gly Ala Glu Leu Val Arg Pro Gly Ala
1               5                   10                  15

Ser Val Lys Met Ser Cys Lys Ala Ser Gly Phe Ala Phe Thr Thr Tyr
            20                  25                  30

Asn Met His Trp Val Lys His Thr Pro Gly Gln Gly Leu Glu Trp Ile
        35                  40                  45

Gly Ala Ile Tyr Pro Gly Asn Gly Glu Thr Ser Tyr Asn Gln Lys Phe
    50                  55                  60
```

Lys Asp Arg Ala Thr Leu Thr Val Asp Lys Ser Ser Arg Thr Ala Tyr
65                  70                  75                  80

Met Gln Leu Ser Ser Leu Thr Ser Glu Asp Ser Ala Val Tyr Phe Cys
            85                  90                  95

Ala Arg Glu Asp Asp Tyr Gly Glu Gly Tyr Phe Asp Val Trp Gly Ala
            100                 105                 110

Gly Thr Thr Val Thr Val Ser Ser
            115                 120

<210> SEQ ID NO 9
<211> LENGTH: 111
<212> TYPE: PRT
<213> ORGANISM: Mus musculus

<400> SEQUENCE: 9

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Ser
            20                  25                  30

Gly Leu Ser Phe Met His Trp Tyr Gln Gln Lys Pro Gly Gln Pro Pro
        35                  40                  45

Arg Leu Leu Leu Tyr Arg Ala Ser Asn Leu Gly Ser Gly Ile Pro Ala
50                  55                  60

Arg Phe Ser Gly Ser Gly Ser Gly Thr Asp Phe Thr Leu Thr Leu Asn
65                  70                  75                  80

Pro Val Glu Thr Asp Asp Val Ala Thr Tyr Tyr Cys Gln Gln Ile Asn
            85                  90                  95

Thr Asp Pro Leu Thr Phe Gly Ala Gly Thr Lys Leu Glu Leu Lys
            100                 105                 110

<210> SEQ ID NO 10
<211> LENGTH: 119
<212> TYPE: PRT
<213> ORGANISM: Mus musculus

<400> SEQUENCE: 10

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asp Pro Gly Asn Gly Asp Thr Asn Tyr Asn Glu Asn Phe
50                  55                  60

Lys Gly Lys Ala Thr Leu Thr Ala Asp Lys Ser Ser Thr Ala Tyr
65                  70                  75                  80

Ile Glu Leu Ser Arg Leu Thr Ser Glu Asp Ser Ala Val Tyr Phe Cys
            85                  90                  95

Ala Arg Glu Asp Asn Thr Gly Thr Ala Phe Asp Tyr Trp Gly Gln Gly
            100                 105                 110

Thr Thr Leu Thr Val Ser Ser
        115

<210> SEQ ID NO 11
<211> LENGTH: 107
<212> TYPE: PRT
<213> ORGANISM: Mus musculus

```
<400> SEQUENCE: 11

Ser Ile Val Met Thr Gln Thr Pro Lys Phe Leu Leu Val Ser Ala Gly
1               5                   10                  15

Asp Arg Val Thr Ile Ser Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Asn His Tyr Thr Gly Val Pro Asp Arg Phe Thr Gly
    50                  55                  60

Ser Gly Tyr Gly Thr Asp Phe Thr Phe Thr Ile Ser Ser Val Gln Ala
65                  70                  75                  80

Glu Asp Leu Ala Val Tyr Phe Cys Gln Gln His His Arg Phe Pro Leu
                85                  90                  95

Thr Phe Gly Ala Gly Thr Lys Leu Glu Leu Lys
            100                 105

<210> SEQ ID NO 12
<211> LENGTH: 117
<212> TYPE: PRT
<213> ORGANISM: Mus musculus

<400> SEQUENCE: 12

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Thr Tyr
            20                  25                  30

Trp Met His Trp Val Lys Gln Arg Pro Gly Gln Gly Leu Glu Trp Ile
        35                  40                  45

Gly Met Ile Asp Pro Ser Asp Ser Glu Thr Thr Leu Ile Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Thr Leu Asp Gly Tyr Tyr Asp Tyr Trp Gly Gln Gly Thr Thr
            100                 105                 110

Leu Thr Val Ser Ser
        115

<210> SEQ ID NO 13
<211> LENGTH: 107
<212> TYPE: PRT
<213> ORGANISM: Mus musculus

<400> SEQUENCE: 13

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Phe Ala Lys Thr Leu Ala Glu Gly Val Pro Ser Arg Phe Ser Gly
    50                  55                  60

Ser Val Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
```

```
                    85                  90                  95
Thr Phe Gly Gly Gly Thr Lys Leu Glu Ile Lys
                100                 105

<210> SEQ ID NO 14
<211> LENGTH: 5
<212> TYPE: PRT
<213> ORGANISM: Mus musculus

<400> SEQUENCE: 14

Asp Asp Tyr Met Asn
1               5

<210> SEQ ID NO 15
<211> LENGTH: 17
<212> TYPE: PRT
<213> ORGANISM: Mus musculus

<400> SEQUENCE: 15

Ile Ile Ser Pro Tyr Asn Gly Gly Thr Ser Tyr Asn Gln Lys Phe Lys
1               5                   10                  15

Gly

<210> SEQ ID NO 16
<211> LENGTH: 12
<212> TYPE: PRT
<213> ORGANISM: Mus musculus

<400> SEQUENCE: 16

Glu Asp Tyr Asp Tyr Asp Gly Tyr Ala Met Asp His
1               5                   10

<210> SEQ ID NO 17
<211> LENGTH: 10
<212> TYPE: PRT
<213> ORGANISM: Mus musculus

<400> SEQUENCE: 17

Arg Ala Ser Ser Ser Val Ser Tyr Met His
1               5                   10

<210> SEQ ID NO 18
<211> LENGTH: 7
<212> TYPE: PRT
<213> ORGANISM: Mus musculus

<400> SEQUENCE: 18

Ala Thr Ser Asn Leu Ala Ser
1               5

<210> SEQ ID NO 19
<211> LENGTH: 8
<212> TYPE: PRT
<213> ORGANISM: Mus musculus

<400> SEQUENCE: 19

Gln Gln Trp Ser Ser Asn Arg Thr
1               5

<210> SEQ ID NO 20
<211> LENGTH: 5
<212> TYPE: PRT
<213> ORGANISM: Mus musculus
```

<400> SEQUENCE: 20

Thr Tyr Asn Met His
1               5

<210> SEQ ID NO 21
<211> LENGTH: 17
<212> TYPE: PRT
<213> ORGANISM: Mus musculus

<400> SEQUENCE: 21

Ala Ile Tyr Pro Gly Asn Gly Glu Thr Ser Tyr Asn Gln Lys Phe Lys
1               5                   10                  15

Asp

<210> SEQ ID NO 22
<211> LENGTH: 11
<212> TYPE: PRT
<213> ORGANISM: Mus musculus

<400> SEQUENCE: 22

Glu Asp Asp Tyr Gly Glu Gly Tyr Phe Asp Val
1               5                   10

<210> SEQ ID NO 23
<211> LENGTH: 15
<212> TYPE: PRT
<213> ORGANISM: Mus musculus

<400> SEQUENCE: 23

Arg Ala Ser Glu Ser Val Asp Asn Ser Gly Leu Ser Phe Met His
1               5                   10                  15

<210> SEQ ID NO 24
<211> LENGTH: 7
<212> TYPE: PRT
<213> ORGANISM: Mus musculus

<400> SEQUENCE: 24

Arg Ala Ser Asn Leu Gly Ser
1               5

<210> SEQ ID NO 25
<211> LENGTH: 9
<212> TYPE: PRT
<213> ORGANISM: Mus musculus

<400> SEQUENCE: 25

Gln Gln Ile Asn Thr Asp Pro Leu Thr
1               5

<210> SEQ ID NO 26
<211> LENGTH: 5
<212> TYPE: PRT
<213> ORGANISM: Mus musculus

<400> SEQUENCE: 26

Asn Tyr Leu Ile Glu
1               5

<210> SEQ ID NO 27
<211> LENGTH: 17
<212> TYPE: PRT
<213> ORGANISM: Mus musculus

```
<400> SEQUENCE: 27

Val Ile Asp Pro Gly Asn Gly Asp Thr Asn Tyr Asn Glu Asn Phe Lys
1               5                   10                  15

Gly

<210> SEQ ID NO 28
<211> LENGTH: 10
<212> TYPE: PRT
<213> ORGANISM: Mus musculus

<400> SEQUENCE: 28

Glu Asp Asn Thr Gly Thr Ala Phe Asp Tyr
1               5                   10

<210> SEQ ID NO 29
<211> LENGTH: 11
<212> TYPE: PRT
<213> ORGANISM: Mus musculus

<400> SEQUENCE: 29

Lys Ala Ser Gln Ser Val Ser Ser Asp Val Thr
1               5                   10

<210> SEQ ID NO 30
<211> LENGTH: 7
<212> TYPE: PRT
<213> ORGANISM: Mus musculus

<400> SEQUENCE: 30

Tyr Val Ser Asn His Tyr Thr
1               5

<210> SEQ ID NO 31
<211> LENGTH: 9
<212> TYPE: PRT
<213> ORGANISM: Mus musculus

<400> SEQUENCE: 31

Gln Gln His His Arg Phe Pro Leu Thr
1               5

<210> SEQ ID NO 32
<211> LENGTH: 5
<212> TYPE: PRT
<213> ORGANISM: Mus musculus

<400> SEQUENCE: 32

Thr Tyr Trp Met His
1               5

<210> SEQ ID NO 33
<211> LENGTH: 17
<212> TYPE: PRT
<213> ORGANISM: Mus musculus

<400> SEQUENCE: 33

Met Ile Asp Pro Ser Asp Ser Glu Thr Thr Leu Ile Gln Lys Phe Lys
1               5                   10                  15

Asp

<210> SEQ ID NO 34
<211> LENGTH: 8
<212> TYPE: PRT
```

<213> ORGANISM: Mus musculus

<400> SEQUENCE: 34

Thr Leu Asp Gly Tyr Tyr Asp Tyr
1               5

<210> SEQ ID NO 35
<211> LENGTH: 11
<212> TYPE: PRT
<213> ORGANISM: Mus musculus

<400> SEQUENCE: 35

Arg Ala Ser Glu Asn Ile Tyr Ser Tyr Leu Ala
1               5                   10

<210> SEQ ID NO 36
<211> LENGTH: 7
<212> TYPE: PRT
<213> ORGANISM: Mus musculus

<400> SEQUENCE: 36

Phe Ala Lys Thr Leu Ala Glu
1               5

<210> SEQ ID NO 37
<211> LENGTH: 9
<212> TYPE: PRT
<213> ORGANISM: Mus musculus

<400> SEQUENCE: 37

Gln His His Tyr Gly Thr Pro Trp Thr
1               5

<210> SEQ ID NO 38
<211> LENGTH: 105
<212> TYPE: PRT
<213> ORGANISM: Artificial Sequence
<220> FEATURE:
<223> OTHER INFORMATION: Synthetic Sequence_hu3 VL-CDR grafted

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Ser Asn Arg Thr Phe
                85                  90                  95

Gly Gly Gly Thr Lys Val Glu Ile Lys
            100                 105

<210> SEQ ID NO 39
<211> LENGTH: 105
<212> TYPE: PRT
<213> ORGANISM: Artificial Sequence
<220> FEATURE:
<223> OTHER INFORMATION: Synthetic Sequence_hu3VL2

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Leu Ile Tyr
            35                  40                  45

Ala Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Ser Asn Arg Thr Phe
                85                  90                  95

Gly Gly Gly Thr Lys Val Glu Ile Lys
            100                 105

<210> SEQ ID NO 40
<211> LENGTH: 105
<212> TYPE: PRT
<213> ORGANISM: Artificial Sequence
<220> FEATURE:
<223> OTHER INFORMATION: Synthetic Sequence_hu3VL3

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Ser Asn Arg Thr Phe
                85                  90                  95

Gly Gly Gly Thr Lys Val Glu Ile Lys
            100                 105

<210> SEQ ID NO 41
<211> LENGTH: 105
<212> TYPE: PRT
<213> ORGANISM: Artificial Sequence
<220> FEATURE:
<223> OTHER INFORMATION: Synthetic Sequence_hu3VL4

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Thr Leu Thr Ile Ser Arg Leu Glu Pro Glu
65                  70                  75                  80

```
Asp Phe Ala Val Tyr Tyr Cys Gln Gln Trp Ser Ser Asn Arg Thr Phe
                85                  90                  95

Gly Gly Gly Thr Lys Val Glu Ile Lys
            100                 105

<210> SEQ ID NO 42
<211> LENGTH: 121
<212> TYPE: PRT
<213> ORGANISM: Artificial Sequence
<220> FEATURE:
<223> OTHER INFORMATION: Synthetic Sequence_hu3VH1

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Asn Trp Val Arg Gln Ala Pro Gly Gln Arg Leu Glu Trp Met
        35                  40                  45

Gly Ile Ile Ser Pro Tyr Asn Gly Gly Thr Ser Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Asp Tyr Asp Gly Tyr Ala Met Asp His Trp Gly
            100                 105                 110

Gln Gly Thr Thr Val Thr Val Ser Ser
            115                 120

<210> SEQ ID NO 43
<211> LENGTH: 121
<212> TYPE: PRT
<213> ORGANISM: Artificial Sequence
<220> FEATURE:
<223> OTHER INFORMATION: Synthetic Sequence_hu3VH2

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Asn Trp Val Arg Gln Ala Pro Gly Gln Arg Leu Glu Trp Met
        35                  40                  45

Gly Ile Ile Ser Pro Tyr Asn Gly Gly Thr Ser Tyr Asn Gln Lys Phe
    50                  55                  60

Lys Gly Arg Val Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Asp Tyr Asp Gly Tyr Ala Met Asp His Trp Gly
            100                 105                 110

Gln Gly Thr Thr Val Thr Val Ser Ser
            115                 120

<210> SEQ ID NO 44
<211> LENGTH: 121
<212> TYPE: PRT
<213> ORGANISM: Artificial Sequence
```

```
<220> FEATURE:
<223> OTHER INFORMATION: Synthetic Sequence_hu3VH3

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
                20                  25                  30

Tyr Met Asn Trp Val Lys Gln Ala Pro Gly Gln Arg Leu Glu Trp Ile
            35                  40                  45

Gly Ile Ile Ser Pro Tyr Asn Gly Thr Tyr Asn Gln Lys Phe
50                  55                  60

Lys Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Asp Tyr Asp Gly Tyr Ala Met Asp His Trp Gly
            100                 105                 110

Gln Gly Thr Thr Val Thr Val Ser Ser
        115                 120

<210> SEQ ID NO 45
<211> LENGTH: 12
<212> TYPE: PRT
<213> ORGANISM: Artificial Sequence
<220> FEATURE:
<223> OTHER INFORMATION: Synthetic Sequence_hu3 HCDR3-H110Y

<400> SEQUENCE: 45

Glu Asp Tyr Asp Tyr Asp Gly Tyr Ala Met Asp Tyr
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Synthetic Sequence_hu3LCDR3-N93D

<400> SEQUENCE: 46

Gln Gln Trp Ser Ser Asp Arg Thr
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic Sequence_hu3 HCDR3 (general formula)
<220> FEATURE:
<221> NAME/KEY: misc_feature
<222> LOCATION: (12)..(12)
<223> OTHER INFORMATION: Xaa can be any naturally occurring amino acid

<400> SEQUENCE: 47

Glu Asp Tyr Asp Tyr Asp Gly Tyr Ala Met Asp Xaa
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic Sequence_hu3 LCDR (general formula 1)
```

```
<220> FEATURE:
<221> NAME/KEY: misc_feature
<222> LOCATION: (6)..(6)
<223> OTHER INFORMATION: Xaa can be any naturally occurring amino acid

<400> SEQUENCE: 48

Gln Gln Trp Ser Ser Xaa Arg Thr
1               5

<210> SEQ ID NO 49
<211> LENGTH: 105
<212> TYPE: PRT
<213> ORGANISM: Artificial Sequence
<220> FEATURE:
<223> OTHER INFORMATION: Synthetic Sequence_Light chain variable
      sequence of hu3-11

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Trp Ser Ser Asp Arg Thr Phe
                85                  90                  95

Gly Gly Gly Thr Lys Val Glu Ile Lys
            100                 105

<210> SEQ ID NO 50
<211> LENGTH: 121
<212> TYPE: PRT
<213> ORGANISM: Artificial Sequence
<220> FEATURE:
<223> OTHER INFORMATION: Synthetic Sequence_Heavy chain variable
      sequence of hu3-11

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Asn Trp Val Arg Gln Ala Pro Gly Gln Arg Leu Glu Trp Met
        35                  40                  45

Gly Ile Ile Ser Pro Tyr Asn Gly Gly Thr Ser Tyr Asn Gln Lys Phe
    50                  55                  60

Lys Gly Arg Val Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Asp Tyr Asp Gly Tyr Ala Met Asp Tyr Trp Gly
            100                 105                 110

Gln Gly Thr Thr Val Thr Val Ser Ser
        115                 120

<210> SEQ ID NO 51
```

```
<211> LENGTH: 105
<212> TYPE: PRT
<213> ORGANISM: Artificial Sequence
<220> FEATURE:
<223> OTHER INFORMATION: Synthetic Sequence_hu3VL5

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Ser Asp Asn Val Arg Gly Phe
                85                  90                  95

Gly Gly Gly Thr Lys Val Glu Ile Lys
            100                 105

<210> SEQ ID NO 52
<211> LENGTH: 105
<212> TYPE: PRT
<213> ORGANISM: Artificial Sequence
<220> FEATURE:
<223> OTHER INFORMATION: Synthetic Sequence_hu3VL6

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Ser Asp Ser Gly Arg Glu Phe
                85                  90                  95

Gly Gly Gly Thr Lys Val Glu Ile Lys
            100                 105

<210> SEQ ID NO 53
<211> LENGTH: 8
<212> TYPE: PRT
<213> ORGANISM: Artificial Sequence
<220> FEATURE:
<223> OTHER INFORMATION: Synthetic Sequence_hu3 LCDR3-V1

<400> SEQUENCE: 53

Gln Gln Ser Asp Asn Val Arg Gly
1               5

<210> SEQ ID NO 54
<211> LENGTH: 8
<212> TYPE: PRT
<213> ORGANISM: Artificial Sequence
<220> FEATURE:
```

<223> OTHER INFORMATION: Synthetic Sequence_hu3 LCDR3-V2

<400> SEQUENCE: 54

Gln Gln Ser Asp Ser Gly Arg Glu
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Sequence_hu3 LCDR3 (general formula
      2)
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 55

Gln Gln Ser Asp Xaa Xaa Arg Xaa
1               5

<210> SEQ ID NO 56
<211> LENGTH: 111
<212> TYPE: PRT
<213> ORGANISM: Artificial Sequence
<220> FEATURE:
<223> OTHER INFORMATION: Synthetic Sequence_hu119-VL CDR grafted(IGKV4-
      1*01)

<400> SEQUENCE: 56

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Ser
                20                  25                  30

Gly Leu Ser Phe Met His Trp Tyr Gln Gln Lys Pro Gly Gln Pro Pro
            35                  40                  45

Lys Leu Leu Ile Tyr Arg Ala Ser Asn Leu Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Asn
                85                  90                  95

Thr Asp Pro Leu Thr Phe Gly Gln Gly Thr Lys Leu Glu Ile Lys
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Synthetic Sequence_hu119VL2

<400> SEQUENCE: 57

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Ser
                20                  25                  30

Gly Leu Ser Phe Met His Trp Tyr Gln Gln Lys Pro Gly Gln Pro Pro
            35                  40                  45

```
Lys Leu Leu Ile Tyr Arg Ala Ser Asn Leu Gly Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ile Asn
                 85                  90                  95

Thr Asp Pro Leu Thr Phe Gly Gln Gly Thr Lys Leu Glu Ile Lys
                100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Synthetic Sequence_hu119VL3

<400> SEQUENCE: 58

Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Asp Asn Ser
                 20                  25                  30

Gly Leu Ser Phe Met His Trp Tyr Gln Gln Lys Pro Gly Gln Pro Pro
             35                  40                  45

Lys Leu Leu Leu Tyr Arg Ala Ser Asn Leu Gly Ser Gly Ile Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ile Asn
                 85                  90                  95

Thr Asp Pro Leu Thr Phe Gly Gln Gly Thr Lys Leu Glu Ile Lys
                100                 105                 110

<210> SEQ ID NO 59
<211> LENGTH: 111
<212> TYPE: PRT
<213> ORGANISM: Artificial Sequence
<220> FEATURE:
<223> OTHER INFORMATION: Synthetic Sequence_hu119VL4 (Grafted, IGKV3-
      11*01)

<400> SEQUENCE: 59

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Asp Asn Ser
                 20                  25                  30

Gly Leu Ser Phe Met His Trp Tyr Gln Gln Lys Pro Gly Gln Ala Pro
             35                  40                  45

Arg Leu Leu Ile Tyr Arg Ala Ser Asn Leu Gly Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ile Asn
                 85                  90                  95

Thr Asp Pro Leu Thr Phe Gly Gln Gly Thr Lys Leu Glu Ile Lys
                100                 105                 110

<210> SEQ ID NO 60
<211> LENGTH: 111
```

```
<212> TYPE: PRT
<213> ORGANISM: Artificial Sequence
<220> FEATURE:
<223> OTHER INFORMATION: Synthetic Sequence_hu119VL5

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Ser
            20                  25                  30

Gly Leu Ser Phe Met His Trp Tyr Gln Gln Lys Pro Gly Gln Pro Pro
        35                  40                  45

Arg Leu Leu Leu Tyr Arg Ala Ser Asn Leu Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ile Asn
                85                  90                  95

Thr Asp Pro Leu Thr Phe Gly Gln Gly Thr Lys Leu Glu Ile Lys
            100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Synthetic Sequence_hu119VL6

<400> SEQUENCE: 61

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Ser
            20                  25                  30

Gly Leu Ser Phe Met His Trp Tyr Gln Gln Lys Pro Gly Gln Pro Pro
        35                  40                  45

Arg Leu Leu Leu Tyr Arg Ala Ser Asn Leu Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ile Asn
                85                  90                  95

Thr Asp Pro Leu Thr Phe Gly Gln Gly Thr Lys Leu Glu Ile Lys
            100                 105                 110

<210> SEQ ID NO 62
<211> LENGTH: 120
<212> TYPE: PRT
<213> ORGANISM: Artificial Sequence
<220> FEATURE:
<223> OTHER INFORMATION: Synthetic Sequence_hu119VH1 (Grafted)

<400> SEQUENCE: 62

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Glu Thr Ser Tyr Asn Gln Lys Phe
```

```
                50                  55                  60
Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Asp Asp Tyr Gly Glu Gly Tyr Phe Asp Val Trp Gly Gln
               100                 105                 110

Gly Thr Thr Val Thr Val Ser Ser
               115                 120

<210> SEQ ID NO 63
<211> LENGTH: 120
<212> TYPE: PRT
<213> ORGANISM: Artificial Sequence
<220> FEATURE:
<223> OTHER INFORMATION: Synthetic Sequence_hu119VH2

<400> SEQUENCE: 63

Glu Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Ser Thr Tyr
                 20                  25                  30

Asn Met His Trp Val Arg Gln Ala Pro Gly Gln Gly Leu Glu Trp Met
                 35                  40                  45

Gly Ala Ile Tyr Pro Gly Asn Gly Glu Thr Ser Tyr Asn Gln Lys Phe
                 50                  55                  60

Lys Asp Arg Val Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Asp Tyr Gly Glu Gly Tyr Phe Asp Val Trp Gly Gln
                100                 105                 110

Gly Thr Thr Val Thr Val Ser Ser
                115                 120

<210> SEQ ID NO 64
<211> LENGTH: 120
<212> TYPE: PRT
<213> ORGANISM: Artificial Sequence
<220> FEATURE:
<223> OTHER INFORMATION: Synthetic Sequence_hu119VH3

<400> SEQUENCE: 64

Glu Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Ser Thr Tyr
                 20                  25                  30

Asn Met His Trp Val Lys His Ala Pro Gly Gln Gly Leu Glu Trp Ile
                 35                  40                  45

Gly Ala Ile Tyr Pro Gly Asn Gly Glu Thr Ser Tyr Asn Gln Lys Phe
                 50                  55                  60

Lys Asp Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Asp Tyr Gly Glu Gly Tyr Phe Asp Val Trp Gly Gln
                100                 105                 110
```

```
Gly Thr Thr Val Thr Val Ser Ser
        115                 120

<210> SEQ ID NO 65
<211> LENGTH: 120
<212> TYPE: PRT
<213> ORGANISM: Artificial Sequence
<220> FEATURE:
<223> OTHER INFORMATION: Synthetic Sequence_hu119VH4

<400> SEQUENCE: 65

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Thr Tyr
            20                  25                  30

Asn Met His Trp Val Lys His Ala Pro Gly Gln Gly Leu Glu Trp Ile
        35                  40                  45

Gly Ala Ile Tyr Pro Gly Asn Gly Glu Thr Ser Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp Tyr Gly Glu Gly Tyr Phe Asp Val Trp Gly Gln
            100                 105                 110

Gly Thr Thr Val Thr Val Ser Ser
        115                 120

<210> SEQ ID NO 66
<211> LENGTH: 120
<212> TYPE: PRT
<213> ORGANISM: Artificial Sequence
<220> FEATURE:
<223> OTHER INFORMATION: Synthetic Sequence_hu119VH5

<400> SEQUENCE: 66

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Asn Met His Trp Val Arg Gln Ala Pro Gly Gln Gly Leu Glu Trp Ile
        35                  40                  45

Gly Ala Ile Tyr Pro Gly Asn Gly Glu Thr Ser Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp Tyr Gly Glu Gly Tyr Phe Asp Val Trp Gly Gln
            100                 105                 110

Gly Thr Thr Val Thr Val Ser Ser
        115                 120

<210> SEQ ID NO 67
<211> LENGTH: 120
<212> TYPE: PRT
<213> ORGANISM: Artificial Sequence
<220> FEATURE:
<223> OTHER INFORMATION: Synthetic Sequence_hu119VH6
```

-continued

```
<400> SEQUENCE: 67

Glu Ala Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Thr Tyr
            20                  25                  30

Asn Met His Trp Val Arg Gln Ala Pro Gly Gln Gly Leu Glu Trp Ile
        35                  40                  45

Gly Ala Ile Tyr Pro Gly Asn Gly Glu Thr Ser Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp Tyr Gly Glu Gly Tyr Phe Asp Val Trp Gly Gln
            100                 105                 110

Gly Thr Thr Val Thr Val Ser Ser
        115                 120

<210> SEQ ID NO 68
<211> LENGTH: 120
<212> TYPE: PRT
<213> ORGANISM: Artificial Sequence
<220> FEATURE:
<223> OTHER INFORMATION: Synthetic Sequence_hu119VH7

<400> SEQUENCE: 68

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Asn Met His Trp Val Arg Gln Ala Pro Gly Gln Gly Leu Glu Trp Ile
        35                  40                  45

Gly Ala Ile Tyr Pro Gly Asn Gly Glu Thr Ser Tyr Asn Gln Lys Phe
    50                  55                  60

Lys Asp Arg Ala Thr Leu Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp Tyr Gly Glu Gly Tyr Phe Asp Val Trp Gly Gln
            100                 105                 110

Gly Thr Thr Val Thr Val Ser Ser
        115                 120

<210> SEQ ID NO 69
<211> LENGTH: 120
<212> TYPE: PRT
<213> ORGANISM: Artificial Sequence
<220> FEATURE:
<223> OTHER INFORMATION: Synthetic Sequence_hu119VH8

<400> SEQUENCE: 69

Glu Ala Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Thr Tyr
            20                  25                  30

Asn Met His Trp Val Arg Gln Ala Pro Gly Gln Gly Leu Glu Trp Ile
        35                  40                  45
```

Gly Ala Ile Tyr Pro Gly Asn Gly Glu Thr Ser Tyr Asn Gln Lys Phe
            50                  55                  60

Lys Asp Arg Ala Thr Leu Thr Val Asp Lys Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Asp Tyr Gly Glu Gly Tyr Phe Asp Val Trp Gly Gln
                100                 105                 110

Gly Thr Thr Val Thr Val Ser Ser
            115                 120

<210> SEQ ID NO 70
<211> LENGTH: 15
<212> TYPE: PRT
<213> ORGANISM: Artificial Sequence
<220> FEATURE:
<223> OTHER INFORMATION: Synthetic Sequence_hu119 LCDR1-N31S

<400> SEQUENCE: 70

Arg Ala Ser Glu Ser Val Asp Ser Ser Gly Leu Ser Phe Met His
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic Sequence_hu119 LCDR1-N31Q

<400> SEQUENCE: 71

Arg Ala Ser Glu Ser Val Asp Gln Ser Gly Leu Ser Phe Met His
 1               5                  10                  15

<210> SEQ ID NO 72
<211> LENGTH: 111
<212> TYPE: PRT
<213> ORGANISM: Artificial Sequence
<220> FEATURE:
<223> OTHER INFORMATION: Synthetic Sequence_hu119VL2-N31S

<400> SEQUENCE: 72

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Glu Ser Val Asp Ser Ser
                20                  25                  30

Gly Leu Ser Phe Met His Trp Tyr Gln Gln Lys Pro Gly Gln Pro Pro
             35                  40                  45

Lys Leu Leu Ile Tyr Arg Ala Ser Asn Leu Gly Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ile Asn
                 85                  90                  95

Thr Asp Pro Leu Thr Phe Gly Gln Gly Thr Lys Leu Glu Ile Lys
                100                 105                 110

<210> SEQ ID NO 73
<211> LENGTH: 111
<212> TYPE: PRT
<213> ORGANISM: Artificial Sequence
<220> FEATURE:
<223> OTHER INFORMATION: Synthetic Sequence_hu119VL2-N31Q

<400> SEQUENCE: 73

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Gln Ser
            20                  25                  30

Gly Leu Ser Phe Met His Trp Tyr Gln Gln Lys Pro Gly Gln Pro Pro
        35                  40                  45

Lys Leu Leu Ile Tyr Arg Ala Ser Asn Leu Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Asn
                85                  90                  95

Thr Asp Pro Leu Thr Phe Gly Gln Gly Thr Lys Leu Glu Ile Lys
            100                 105                 110

<210> SEQ ID NO 74
<211> LENGTH: 111
<212> TYPE: PRT
<213> ORGANISM: Artificial Sequence
<220> FEATURE:
<223> OTHER INFORMATION: Synthetic Sequence_hu119VL6-N31S

<400> SEQUENCE: 74

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Ser
            20                  25                  30

Gly Leu Ser Phe Met His Trp Tyr Gln Gln Lys Pro Gly Gln Pro Pro
        35                  40                  45

Arg Leu Leu Leu Tyr Arg Ala Ser Asn Leu Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ile Asn
                85                  90                  95

Thr Asp Pro Leu Thr Phe Gly Gln Gly Thr Lys Leu Glu Ile Lys
            100                 105                 110

<210> SEQ ID NO 75
<211> LENGTH: 111
<212> TYPE: PRT
<213> ORGANISM: Artificial Sequence
<220> FEATURE:
<223> OTHER INFORMATION: Synthetic Sequence_hu119VL6-N31Q

<400> SEQUENCE: 75

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Gln Ser
            20                  25                  30

Gly Leu Ser Phe Met His Trp Tyr Gln Gln Lys Pro Gly Gln Pro Pro
        35                  40                  45

Arg Leu Leu Leu Tyr Arg Ala Ser Asn Leu Gly Ser Gly Ile Pro Ala
    50                  55                  60

Arg Phe Ser Gly Ser Gly Ser Gly Thr Asp Phe Thr Leu Thr Ile Ser
65                  70                  75                  80

```
Ser Leu Glu Pro Glu Asp Phe Ala Val Tyr Tyr Cys Gln Gln Ile Asn
                85                  90                  95

Thr Asp Pro Leu Thr Phe Gly Gln Gly Thr Lys Leu Glu Ile Lys
            100                 105                 110

<210> SEQ ID NO 76
<211> LENGTH: 15
<212> TYPE: PRT
<213> ORGANISM: Artificial Sequence
<220> FEATURE:
<223> OTHER INFORMATION: Synthetic Sequence_hu119 LCDR1-general formula
<220> FEATURE:
<221> NAME/KEY: misc_feature
<222> LOCATION: (8)..(8)
<223> OTHER INFORMATION: Xaa can be any naturally occurring amino acid

<400> SEQUENCE: 76

Arg Ala Ser Glu Ser Val Asp Xaa Ser Gly Leu Ser Phe Met His
1               5                   10                  15

<210> SEQ ID NO 77
<211> LENGTH: 107
<212> TYPE: PRT
<213> ORGANISM: Artificial Sequence
<220> FEATURE:
<223> OTHER INFORMATION: Synthetic Sequence_hu179VL1 (Graft (IGKV4-
      1*01))

<400> SEQUENCE: 77

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Pro Pro Lys Leu Leu Ile
        35                  40                  45

Tyr Tyr Val Ser Asn His Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 78
<211> LENGTH: 107
<212> TYPE: PRT
<213> ORGANISM: Artificial Sequence
<220> FEATURE:
<223> OTHER INFORMATION: Synthetic Sequence_hu179VL2

<400> SEQUENCE: 78

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Asn His Tyr Thr Gly Val Pro Asp Arg Phe Ser Gly
    50                  55                  60

Ser Gly Ser Gly Thr Asp Phe Thr Leu Thr Ile Ser Ser Leu Gln Ala
```

```
                65                  70                  75                  80
Glu Asp Val Ala Val Tyr Tyr Cys Gln Gln His His Arg Phe Pro Leu
                    85                  90                  95

Thr Phe Gly Gln Gly Thr Lys Leu Glu Ile Lys
            100                 105

<210> SEQ ID NO 79
<211> LENGTH: 107
<212> TYPE: PRT
<213> ORGANISM: Artificial Sequence
<220> FEATURE:
<223> OTHER INFORMATION: Synthetic Sequence_hu179 VL3

<400> SEQUENCE: 79

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
                20                  25                  30

Val Thr Trp Tyr Gln Gln Lys Pro Gly Gln Ser Pro Lys Leu Leu Ile
            35                  40                  45

Tyr Tyr Val Ser Asn His Tyr Thr Gly Val Pro Asp Arg Phe Ser Gly
        50                  55                  60

Ser Gly Ser Gly Thr Asp Phe Thr Phe Thr Ile Ser Ser Leu Gln Ala
65                  70                  75                  80

Glu Asp Val Ala Val Tyr Tyr Cys Gln Gln His His Arg Phe Pro Leu
                    85                  90                  95

Thr Phe Gly Gln Gly Thr Lys Leu Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: Synthetic Sequence_hu179 VL4

<400> SEQUENCE: 80

Ser Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
                20                  25                  30

Val Thr Trp Tyr Gln Gln Lys Pro Gly Gln Ser Pro Lys Leu Leu Ile
            35                  40                  45

Tyr Tyr Val Ser Asn His Tyr Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                    85                  90                  95

Thr Phe Gly Gln Gly Thr Lys Leu Glu Ile Lys
            100                 105

<210> SEQ ID NO 81
<211> LENGTH: 107
<212> TYPE: PRT
<213> ORGANISM: Artificial Sequence
<220> FEATURE:
<223> OTHER INFORMATION: Synthetic Sequence_hu179VL5 (Grafted(IGKV2-
      29*02))
```

```
<400> SEQUENCE: 81

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Ser Ser Asp
            20                  25                  30

Val Thr Trp Tyr Leu Gln Lys Pro Gly Gln Ser Pro Gln Leu Leu Ile
        35                  40                  45

Tyr Tyr Val Ser Asn His Tyr Thr Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 82
<211> LENGTH: 107
<212> TYPE: PRT
<213> ORGANISM: Artificial Sequence
<220> FEATURE:
<223> OTHER INFORMATION: Synthetic Sequence_hu179VL6

<400> SEQUENCE: 82

Ser Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Ser Ser Asp
            20                  25                  30

Val Thr Trp Tyr Leu Gln Lys Pro Gly Gln Ser Pro Gln Leu Leu Ile
        35                  40                  45

Tyr Tyr Val Ser Asn His Tyr Thr Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 83
<211> LENGTH: 107
<212> TYPE: PRT
<213> ORGANISM: Artificial Sequence
<220> FEATURE:
<223> OTHER INFORMATION: Synthetic Sequence_hu179VL7

<400> SEQUENCE: 83

Ser Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Ser Ser Asp
            20                  25                  30

Val Thr Trp Tyr Leu Gln Lys Pro Gly Gln Ser Pro Gln Leu Leu Ile
        35                  40                  45

Tyr Tyr Val Ser Asn His Tyr Thr Gly Val Pro Asp Arg Phe Ser Gly
    50                  55                  60

Ser Gly Ser Gly Thr Asp Phe Thr Phe Lys Ile Ser Arg Val Glu Ala
65                  70                  75                  80
```

```
Glu Asp Val Gly Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: Synthetic Sequence_hu179VL8

<400> SEQUENCE: 84

Ser Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Ser Ser Asp
            20                  25                  30

Val Thr Trp Tyr Leu Gln Lys Pro Gly Gln Ser Pro Gln Leu Leu Ile
        35                  40                  45

Tyr Tyr Val Ser Asn His Tyr Thr Gly Val Pro Asp Arg Phe Ser Gly
50                  55                  60

Ser Gly Tyr Gly Thr Asp Phe Thr Leu Lys Ile Ser Arg Val Glu Ala
65                  70                  75                  80

Glu Asp Val Gly Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 85
<211> LENGTH: 119
<212> TYPE: PRT
<213> ORGANISM: Artificial Sequence
<220> FEATURE:
<223> OTHER INFORMATION: Synthetic Sequence_hu179VH1 (Grafted)

<400> SEQUENCE: 85

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Leu Ile Glu Trp Val Arg Gln Ala Pro Gly Gln Gly Leu Glu Trp Met
        35                  40                  45

Gly Val Ile Asp Pro Gly Asn Gly Asp Thr Asn Tyr Asn Glu Asn Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asn Thr Gly Thr Ala Phe Asp Tyr Trp Gly Gln Gly
            100                 105                 110

Thr Thr Val Thr Val Ser Ser
            115

<210> SEQ ID NO 86
<211> LENGTH: 119
<212> TYPE: PRT
<213> ORGANISM: Artificial Sequence
<220> FEATURE:
<223> OTHER INFORMATION: Synthetic Sequence_hu179VH2
```

<400> SEQUENCE: 86

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Leu Ile Glu Trp Val Arg Gln Ala Pro Gly Gln Gly Leu Glu Trp Met
        35                  40                  45

Gly Val Ile Asp Pro Gly Asn Gly Asp Thr Asn Tyr Asn Glu Asn Phe
50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asn Thr Gly Thr Ala Phe Asp Tyr Trp Gly Gln Gly
            100                 105                 110

Thr Thr Val Thr Val Ser Ser
        115

<210> SEQ ID NO 87
<211> LENGTH: 119
<212> TYPE: PRT
<213> ORGANISM: Artificial Sequence
<220> FEATURE:
<223> OTHER INFORMATION: Synthetic Sequence_hu179VH3

<400> SEQUENCE: 87

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Leu Ile Glu Trp Val Arg Gln Ala Pro Gly Gln Gly Leu Glu Trp Ile
        35                  40                  45

Gly Val Ile Asp Pro Gly Asn Gly Asp Thr Asn Tyr Asn Glu Asn Phe
50                  55                  60

Lys Gly Arg Ala Thr Leu Thr Ala Asp Lys Ser Thr Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Glu Asp Asn Thr Gly Thr Ala Phe Asp Tyr Trp Gly Gln Gly
            100                 105                 110

Thr Thr Val Thr Val Ser Ser
        115

<210> SEQ ID NO 88
<211> LENGTH: 119
<212> TYPE: PRT
<213> ORGANISM: Artificial Sequence
<220> FEATURE:
<223> OTHER INFORMATION: Synthetic Sequence_hu179VH4

<400> SEQUENCE: 88

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Leu Ile Glu Trp Val Lys Gln Ala Pro Gly Gln Gly Leu Glu Trp Ile
        35                  40                  45

Gly Val Ile Asp Pro Gly Asn Gly Asp Thr Asn Tyr Asn Glu Asn Phe
                50                  55                  60

Lys Gly Lys Ala Thr Leu Thr Ala Asp Lys Ser Thr Ser Thr Ala Tyr
 65                  70                  75                  80

Ile Glu Leu Ser Arg Leu Arg Ser Glu Asp Thr Ala Val Tyr Tyr Cys
                 85                  90                  95

Ala Arg Glu Asp Asn Thr Gly Thr Ala Phe Asp Tyr Trp Gly Gln Gly
                100                 105                 110

Thr Thr Val Thr Val Ser Ser
            115

<210> SEQ ID NO 89
<211> LENGTH: 119
<212> TYPE: PRT
<213> ORGANISM: Artificial Sequence
<220> FEATURE:
<223> OTHER INFORMATION: Synthetic Sequence_hu179VH5

<400> SEQUENCE: 89

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Asn Tyr
                20                  25                  30

Leu Ile Glu Trp Val Arg Gln Ala Pro Gly Gln Gly Leu Glu Trp Ile
             35                  40                  45

Gly Val Ile Asp Pro Gly Asn Gly Asp Thr Asn Tyr Asn Glu Asn Phe
         50                  55                  60

Lys Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Asn Thr Gly Thr Ala Phe Asp Tyr Trp Gly Gln Gly
                100                 105                 110

Thr Thr Val Thr Val Ser Ser
            115

<210> SEQ ID NO 90
<211> LENGTH: 119
<212> TYPE: PRT
<213> ORGANISM: Artificial Sequence
<220> FEATURE:
<223> OTHER INFORMATION: Synthetic Sequence_hu179VH1- N55Q

<400> SEQUENCE: 90

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
                20                  25                  30

Leu Ile Glu Trp Val Arg Gln Ala Pro Gly Gln Gly Leu Glu Trp Met
             35                  40                  45

Gly Val Ile Asp Pro Gly Gln Gly Asp Thr Asn Tyr Asn Glu Asn Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Asp Asn Thr Gly Thr Ala Phe Asp Tyr Trp Gly Gln Gly
                100                 105                 110

```
Thr Thr Val Thr Val Ser Ser
        115

<210> SEQ ID NO 91
<211> LENGTH: 119
<212> TYPE: PRT
<213> ORGANISM: Artificial Sequence
<220> FEATURE:
<223> OTHER INFORMATION: Synthetic Sequence_hu179VH1- N55V

<400> SEQUENCE: 91

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Leu Ile Glu Trp Val Arg Gln Ala Pro Gly Gln Gly Leu Glu Trp Met
        35                  40                  45

Gly Val Ile Asp Pro Gly Val Gly Asp Thr Asn Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asn Thr Gly Thr Ala Phe Asp Tyr Trp Gly Gln Gly
            100                 105                 110

Thr Thr Val Thr Val Ser Ser
        115

<210> SEQ ID NO 92
<211> LENGTH: 119
<212> TYPE: PRT
<213> ORGANISM: Artificial Sequence
<220> FEATURE:
<223> OTHER INFORMATION: Synthetic Sequence_hu179VH1- G56V

<400> SEQUENCE: 92

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Leu Ile Glu Trp Val Arg Gln Ala Pro Gly Gln Gly Leu Glu Trp Met
        35                  40                  45

Gly Val Ile Asp Pro Gly Asn Val Asp Thr Asn Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asn Thr Gly Thr Ala Phe Asp Tyr Trp Gly Gln Gly
            100                 105                 110

Thr Thr Val Thr Val Ser Ser
        115

<210> SEQ ID NO 93
<211> LENGTH: 17
<212> TYPE: PRT
<213> ORGANISM: Artificial Sequence
<220> FEATURE:
<223> OTHER INFORMATION: Synthetic Sequence_hu179 HCDR2-N55Q
```

```
<400> SEQUENCE: 93

Val Ile Asp Pro Gly Gln Gly Asp Thr Asn Tyr Asn Glu Asn Phe Lys
1               5                   10                  15

Gly

<210> SEQ ID NO 94
<211> LENGTH: 17
<212> TYPE: PRT
<213> ORGANISM: Artificial Sequence
<220> FEATURE:
<223> OTHER INFORMATION: Synthetic Sequence_hu179 HCDR2-N55V

<400> SEQUENCE: 94

Val Ile Asp Pro Gly Val Gly Asp Thr Asn Tyr Asn Glu Asn Phe Lys
1               5                   10                  15

Gly

<210> SEQ ID NO 95
<211> LENGTH: 17
<212> TYPE: PRT
<213> ORGANISM: Artificial Sequence
<220> FEATURE:
<223> OTHER INFORMATION: Synthetic Sequence_hu179 HCDR2-G56V

<400> SEQUENCE: 95

Val Ile Asp Pro Gly Asn Val Asp Thr Asn Tyr Asn Glu Asn Phe Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic Sequence_hu179 HCDR2 (general
      formula)
<220> FEATURE:
<221> NAME/KEY: misc_feature
<222> LOCATION: (6)..(7)
<223> OTHER INFORMATION: Xaa can be any naturally occurring amino acid

<400> SEQUENCE: 96

Val Ile Asp Pro Gly Xaa Xaa Asp Thr Asn Tyr Asn Glu Asn Phe Lys
1               5                   10                  15

Gly

<210> SEQ ID NO 97
<211> LENGTH: 119
<212> TYPE: PRT
<213> ORGANISM: Artificial Sequence
<220> FEATURE:
<223> OTHER INFORMATION: Synthetic Sequence_hu179VH3-N55V

<400> SEQUENCE: 97

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
                20                  25                  30

Leu Ile Glu Trp Val Arg Gln Ala Pro Gly Gln Gly Leu Glu Trp Ile
            35                  40                  45

Gly Val Ile Asp Pro Gly Val Gly Asp Thr Asn Tyr Asn Glu Asn Phe
        50                  55                  60
```

Lys Gly Arg Ala Thr Leu Thr Ala Asp Lys Ser Thr Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Glu Asp Asn Thr Gly Thr Ala Phe Asp Tyr Trp Gly Gln Gly
            100                 105                 110

Thr Thr Val Thr Val Ser Ser
        115

<210> SEQ ID NO 98
<211> LENGTH: 107
<212> TYPE: PRT
<213> ORGANISM: Artificial Sequence
<220> FEATURE:
<223> OTHER INFORMATION: Synthetic Sequence_hu179VL2-Y50E

<400> SEQUENCE: 98

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Glu Val Ser Asn His Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 99
<211> LENGTH: 107
<212> TYPE: PRT
<213> ORGANISM: Artificial Sequence
<220> FEATURE:
<223> OTHER INFORMATION: Synthetic Sequence_hu179VL2-S52D

<400> SEQUENCE: 99

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Asp Asn His Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 100
<211> LENGTH: 107
<212> TYPE: PRT

<213> ORGANISM: Artificial Sequence
<220> FEATURE:
<223> OTHER INFORMATION: Synthetic Sequence_hu179VL2-S52E

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Glu Asn His Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 101
<211> LENGTH: 107
<212> TYPE: PRT
<213> ORGANISM: Artificial Sequence
<220> FEATURE:
<223> OTHER INFORMATION: Synthetic Sequence_hu179VL2-N53Q

<400> SEQUENCE: 101

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Gln His Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Synthetic Sequence_hu179VL2-N53D

<400> SEQUENCE: 102

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Asp His Tyr Thr Gly Val Pro Asp Arg Phe Ser Gly
    50                  55                  60

```
Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Synthetic Sequence_hu179VL2-N53E

<400> SEQUENCE: 103

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Glu His Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 104
<211> LENGTH: 107
<212> TYPE: PRT
<213> ORGANISM: Artificial Sequence
<220> FEATURE:
<223> OTHER INFORMATION: Synthetic Sequence_hu179VL2-H54Y

<400> SEQUENCE: 104

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Asn Tyr Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 105
<211> LENGTH: 107
<212> TYPE: PRT
<213> ORGANISM: Artificial Sequence
<220> FEATURE:
<223> OTHER INFORMATION: Synthetic Sequence_hu179VL2-H54D
```

<400> SEQUENCE: 105

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Asn Asp Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 106
<211> LENGTH: 107
<212> TYPE: PRT
<213> ORGANISM: Artificial Sequence
<220> FEATURE:
<223> OTHER INFORMATION: Synthetic Sequence_hu179VL2-H54E

<400> SEQUENCE: 106

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Asn Glu Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95

Thr Phe Gly Gln Gly Thr Lys Leu Glu Ile Lys
            100                 105

<210> SEQ ID NO 107
<211> LENGTH: 107
<212> TYPE: PRT
<213> ORGANISM: Artificial Sequence
<220> FEATURE:
<223> OTHER INFORMATION: Synthetic Sequence_hu179VL2-Y55E

<400> SEQUENCE: 107

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ser Asp
            20                  25                  30

Val Thr Trp Tyr Gln Gln Lys Pro Gly Gln Ser Pro Lys Leu Leu Ile
        35                  40                  45

Tyr Tyr Val Ser Asn His Glu Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His His Arg Phe Pro Leu
                85                  90                  95
Thr Phe Gly Gln Gly Thr Lys Leu Glu Ile Lys
            100                 105

<210> SEQ ID NO 108
<211> LENGTH: 7
<212> TYPE: PRT
<213> ORGANISM: Artificial Sequence
<220> FEATURE:
<223> OTHER INFORMATION: Synthetic Sequence_hu179 LCDR2-Y50E

<400> SEQUENCE: 108

Glu Val Ser Asn His Tyr Thr
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic Sequence_hu179 LCDR2-S52D

<400> SEQUENCE: 109

Tyr Val Asp Asn His Tyr Thr
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic Sequence_hu179 LCDR2-S52E

<400> SEQUENCE: 110

Tyr Val Glu Asn His Tyr Thr
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic Sequence_hu179LCDR2-N53Q

<400> SEQUENCE: 111

Tyr Val Ser Gln His Tyr Thr
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic Sequence_hu179 LCDR2-N53D

<400> SEQUENCE: 112

Tyr Val Ser Asp His Tyr Thr
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic Sequence_hu179 LCDR2-N53E

```
<400> SEQUENCE: 113

Tyr Val Ser Glu His Tyr Thr
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic Sequence_hu179 LCDR2-H54Y

<400> SEQUENCE: 114

Tyr Val Ser Asn Tyr Tyr Thr
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic Sequence_hu179 LCDR2-H54D

<400> SEQUENCE: 115

Tyr Val Ser Asn Asp Tyr Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic Sequence_hu179 LCDR2-H54E

<400> SEQUENCE: 116

Tyr Val Ser Asn Glu Tyr Thr
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic Sequence_hu179 LCDR2-Y55E

<400> SEQUENCE: 117

Tyr Val Ser Asn His Glu Thr
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic Sequence_mab179 humanized antibody
      LCDR2 general formula
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid

<400> SEQUENCE: 118

Xaa Val Xaa Xaa Xaa Xaa Thr
1               5
```

<210> SEQ ID NO 119
<211> LENGTH: 107
<212> TYPE: PRT
<213> ORGANISM: Artificial Sequence
<220> FEATURE:
<223> OTHER INFORMATION: Synthetic Sequence_hu179VL8-N53E

<400> SEQUENCE: 119

```
Ser Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Ser Ser Asp
            20                  25                  30

Val Thr Trp Tyr Leu Gln Lys Pro Gly Gln Ser Pro Gln Leu Leu Ile
        35                  40                  45

Tyr Tyr Val Ser Glu His Tyr Thr Gly Val Pro Asp Arg Phe Ser Gly
    50                  55                  60

Ser Gly Tyr Gly Thr Asp Phe Thr Leu Lys Ile Ser Arg Val Glu Ala
65                  70                  75                  80

Glu Asp Val Gly Val Tyr Tyr Cys Gln Gln His His Arg Phe Pro Leu
                85                  90                  95

Thr Phe Gly Gln Gly Thr Lys Leu Glu Ile Lys
            100                 105
```

<210> SEQ ID NO 120
<211> LENGTH: 107
<212> TYPE: PRT
<213> ORGANISM: Artificial Sequence
<220> FEATURE:
<223> OTHER INFORMATION: Synthetic Sequence_hu199VL1 (Grafted)

<400> SEQUENCE: 120

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Phe Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Trp
                85                  90                  95

Thr Phe Gly Gly Gly Thr Lys Val Glu Ile Lys
            100                 105
```

<210> SEQ ID NO 121
<211> LENGTH: 107
<212> TYPE: PRT
<213> ORGANISM: Artificial Sequence
<220> FEATURE:
<223> OTHER INFORMATION: Synthetic Sequence_hu199VL2

<400> SEQUENCE: 121

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30
```

```
Leu Ala Trp Tyr Gln Gln Lys Pro Gly Lys Ala Pro Lys Leu Leu Val
            35                  40                  45

Tyr Phe Ala Lys Thr Leu Ala Glu Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Thr Pro Trp
                 85                  90                  95

Thr Phe Gly Gly Gly Thr Lys Val Glu Ile Lys
                100                 105

<210> SEQ ID NO 122
<211> LENGTH: 107
<212> TYPE: PRT
<213> ORGANISM: Artificial Sequence
<220> FEATURE:
<223> OTHER INFORMATION: Synthetic Sequence_hu199VL3

<400> SEQUENCE: 122

Asp Ile Gln Met Thr Gln Ser Pro Ser Ser Leu Ser Ala Ser Val Gly
 1                5                  10                  15

Asp Arg Val Thr Ile Thr Cys Arg Ala Ser Glu Asn Ile Tyr Ser Tyr
                 20                  25                  30

Leu Ala Trp Tyr Gln Gln Lys Pro Gly Lys Ser Pro Gln Leu Leu Val
            35                  40                  45

Tyr Phe Ala Lys Thr Leu Ala Glu Gly Val Pro Ser Arg Phe Ser Gly
 50                  55                  60

Ser Gly Ser Gly Thr Gln Phe Thr Leu Thr Ile Ser Ser Leu Gln Pro
 65                  70                  75                  80

Glu Asp Phe Ala Thr Tyr Tyr Cys Gln His His Tyr Gly Thr Pro Trp
                 85                  90                  95

Thr Phe Gly Gly Gly Thr Lys Val Glu Ile Lys
                100                 105

<210> SEQ ID NO 123
<211> LENGTH: 107
<212> TYPE: PRT
<213> ORGANISM: Artificial Sequence
<220> FEATURE:
<223> OTHER INFORMATION: Synthetic Sequence_hu199VL4

<400> SEQUENCE: 123

Asp Ile Gln Met Thr Gln Ser Pro Ser Ser Leu Ser Ala Ser Val Gly
 1                5                  10                  15

Asp Arg Val Thr Ile Thr Cys Arg Ala Ser Glu Asn Ile Tyr Ser Tyr
                 20                  25                  30

Leu Ala Trp Tyr Gln Gln Lys Pro Gly Lys Ala Pro Lys Leu Leu Ile
            35                  40                  45

Tyr Phe Ala Lys Thr Leu Ala Glu Gly Val Pro Ser Arg Phe Ser Gly
 50                  55                  60

Ser Val Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Thr Pro Trp
                 85                  90                  95

Thr Phe Gly Gly Gly Thr Lys Val Glu Ile Lys
                100                 105

<210> SEQ ID NO 124
```

```
<211> LENGTH: 107
<212> TYPE: PRT
<213> ORGANISM: Artificial Sequence
<220> FEATURE:
<223> OTHER INFORMATION: Synthetic Sequence_hu199VL5

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Phe Ala Lys Thr Leu Ala Glu Gly Val Pro Ser Arg Phe Ser Gly
    50                  55                  60

Ser Val Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Trp
                85                  90                  95

Thr Phe Gly Gly Gly Thr Lys Val Glu Ile Lys
            100                 105

<210> SEQ ID NO 125
<211> LENGTH: 107
<212> TYPE: PRT
<213> ORGANISM: Artificial Sequence
<220> FEATURE:
<223> OTHER INFORMATION: Synthetic Sequence_hu199VL6

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Gln Leu Leu Val
        35                  40                  45

Tyr Phe Ala Lys Thr Leu Ala Glu Gly Val Pro Ser Arg Phe Ser Gly
    50                  55                  60

Ser Val Ser Gly Thr Gln Phe Thr Leu Thr Ile Ser Ser Leu Gln Pro
65                  70                  75                  80

Glu Asp Phe Ala Thr Tyr Tyr Cys Gln His His Tyr Gly Thr Pro Trp
                85                  90                  95

Thr Phe Gly Gly Gly Thr Lys Val Glu Ile Lys
            100                 105

<210> SEQ ID NO 126
<211> LENGTH: 117
<212> TYPE: PRT
<213> ORGANISM: Artificial Sequence
<220> FEATURE:
<223> OTHER INFORMATION: Synthetic Sequence_hu199VH1 (Grafted)

<400> SEQUENCE: 126

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45
```

Gly Met Ile Asp Pro Ser Asp Ser Glu Thr Thr Leu Ile Gln Lys Phe
        50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Thr Leu Asp Gly Tyr Tyr Asp Tyr Trp Gly Gln Gly Thr Thr
                100                 105                 110

Val Thr Val Ser Ser
            115

<210> SEQ ID NO 127
<211> LENGTH: 117
<212> TYPE: PRT
<213> ORGANISM: Artificial Sequence
<220> FEATURE:
<223> OTHER INFORMATION: Synthetic Sequence_hu199VH2

<400> SEQUENCE: 127

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                 20                  25                  30

Trp Met His Trp Val Arg Gln Ala Pro Gly Gln Gly Leu Glu Trp Met
            35                  40                  45

Gly Met Ile Asp Pro Ser Asp Ser Glu Thr Thr Leu Ile Gln Lys Phe
        50                  55                  60

Lys Asp Arg Val Thr Met Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Leu Asp Gly Tyr Tyr Asp Tyr Trp Gly Gln Gly Thr Thr
                100                 105                 110

Val Thr Val Ser Ser
            115

<210> SEQ ID NO 128
<211> LENGTH: 117
<212> TYPE: PRT
<213> ORGANISM: Artificial Sequence
<220> FEATURE:
<223> OTHER INFORMATION: Synthetic Sequence_hu199VH3

<400> SEQUENCE: 128

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                 20                  25                  30

Trp Met His Trp Val Arg Gln Ala Pro Gly Gln Gly Leu Glu Trp Met
            35                  40                  45

Gly Met Ile Asp Pro Ser Asp Ser Glu Thr Thr Leu Ile Gln Lys Phe
        50                  55                  60

Lys Asp Arg Val Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Leu Asp Gly Tyr Tyr Asp Tyr Trp Gly Gln Gly Thr Thr
                100                 105                 110

```
Val Thr Val Ser Ser
        115

<210> SEQ ID NO 129
<211> LENGTH: 117
<212> TYPE: PRT
<213> ORGANISM: Artificial Sequence
<220> FEATURE:
<223> OTHER INFORMATION: Synthetic Sequence_hu199VH4

<400> SEQUENCE: 129

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met His Trp Val Arg Gln Ala Pro Gly Gln Gly Leu Glu Trp Ile
            35                  40                  45

Gly Met Ile Asp Pro Ser Asp Ser Glu Thr Thr Leu Ile Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Leu Asp Gly Tyr Tyr Asp Tyr Trp Gly Gln Gly Thr Thr
            100                 105                 110

Val Thr Val Ser Ser
        115

<210> SEQ ID NO 130
<211> LENGTH: 117
<212> TYPE: PRT
<213> ORGANISM: Artificial Sequence
<220> FEATURE:
<223> OTHER INFORMATION: Synthetic Sequence_hu199VH5

<400> SEQUENCE: 130

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met His Trp Val Lys Gln Ala Pro Gly Gln Gly Leu Glu Trp Ile
            35                  40                  45

Gly Met Ile Asp Pro Ser Asp Ser Glu Thr Thr Leu Ile Gln Lys Phe
    50                  55                  60

Lys Asp Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Leu Asp Gly Tyr Tyr Asp Tyr Trp Gly Gln Gly Thr Thr
            100                 105                 110

Val Thr Val Ser Ser
        115

<210> SEQ ID NO 131
<211> LENGTH: 117
<212> TYPE: PRT
<213> ORGANISM: Artificial Sequence
<220> FEATURE:
<223> OTHER INFORMATION: Synthetic Sequence_hu199VH6
```

<400> SEQUENCE: 131

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Lys Gln Ala Pro Gly Gln Gly Leu Glu Trp Met
        35                  40                  45

Gly Met Ile Asp Pro Ser Asp Ser Glu Thr Thr Leu Ile Gln Lys Phe
    50                  55                  60

Lys Asp Lys Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Leu Asp Gly Tyr Tyr Asp Tyr Trp Gly Gln Gly Thr Thr
                100                 105                 110

Val Thr Val Ser Ser
            115

<210> SEQ ID NO 132
<211> LENGTH: 117
<212> TYPE: PRT
<213> ORGANISM: Artificial Sequence
<220> FEATURE:
<223> OTHER INFORMATION: Synthetic Sequence_hu199VH7

<400> SEQUENCE: 132

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Lys Gln Ala Pro Gly Gln Gly Leu Glu Trp Met
        35                  40                  45

Gly Met Ile Asp Pro Ser Asp Ser Glu Thr Thr Leu Ile Gln Lys Phe
    50                  55                  60

Lys Asp Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Leu Asp Gly Tyr Tyr Asp Tyr Trp Gly Gln Gly Thr Thr
                100                 105                 110

Val Thr Val Ser Ser
            115

<210> SEQ ID NO 133
<211> LENGTH: 330
<212> TYPE: PRT
<213> ORGANISM: Artificial Sequence
<220> FEATURE:
<223> OTHER INFORMATION: Synthetic Sequence_IgG1-YTE heavy chain
      constant region

<400> SEQUENCE: 133

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                    35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Tyr Ile Thr Arg Glu Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 134
<211> LENGTH: 107
<212> TYPE: PRT
<213> ORGANISM: Artificial Sequence
<220> FEATURE:
<223> OTHER INFORMATION: Synthetic Sequence_kappa light chain constant
      region

<400> SEQUENCE: 134

Arg Thr Val Ala Ala Pro Ser Val Phe Ile Phe Pro Pro Ser Asp Glu
  1               5                  10                  15
Gln Leu Lys Ser Gly Thr Ala Ser Val Val Cys Leu Leu Asn Asn Phe
             20                  25                  30
Tyr Pro Arg Glu Ala Lys Val Gln Trp Lys Val Asp Asn Ala Leu Gln
         35                  40                  45
Ser Gly Asn Ser Gln Glu Ser Val Thr Glu Gln Asp Ser Lys Asp Ser
 50                  55                  60
```

```
Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 135
<211> LENGTH: 451
<212> TYPE: PRT
<213> ORGANISM: Artificial Sequence
<220> FEATURE:
<223> OTHER INFORMATION: Synthetic Sequence_hu3-13 antibody heavy chain

<400> SEQUENCE: 135

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
                20                  25                  30

Tyr Met Asn Trp Val Arg Gln Ala Pro Gly Gln Arg Leu Glu Trp Met
            35                  40                  45

Gly Ile Ile Ser Pro Tyr Asn Gly Gly Thr Ser Tyr Asn Gln Lys Phe
50                  55                  60

Lys Gly Arg Val Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Asp Tyr Asp Gly Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320
```

-continued

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 136
<211> LENGTH: 212
<212> TYPE: PRT
<213> ORGANISM: Artificial Sequence
<220> FEATURE:
<223> OTHER INFORMATION: Synthetic Sequence_hu3-13 antibody light chain

<400> SEQUENCE: 136

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Ser Asp Ser Gly Arg Glu Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 137
<211> LENGTH: 450
<212> TYPE: PRT
<213> ORGANISM: Artificial Sequence
<220> FEATURE:
<223> OTHER INFORMATION: Synthetic Sequence_hu119-30 antibody heavy chain

<400> SEQUENCE: 137

```
Glu Ala Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Thr Tyr
            20                  25                  30

Asn Met His Trp Val Arg Gln Ala Pro Gly Gln Gly Leu Glu Trp Ile
        35                  40                  45

Gly Ala Ile Tyr Pro Gly Asn Gly Glu Thr Ser Tyr Asn Gln Lys Phe
    50                  55                  60

Lys Asp Arg Ala Thr Leu Thr Val Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asp Tyr Gly Glu Gly Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 138
<211> LENGTH: 218
<212> TYPE: PRT
<213> ORGANISM: Artificial Sequence
<220> FEATURE:
<223> OTHER INFORMATION: Synthetic Sequence_hu119-30 antibody light
      chain

<400> SEQUENCE: 138

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Ser
            20                  25                  30

Gly Leu Ser Phe Met His Trp Tyr Gln Gln Lys Pro Gly Gln Pro Pro
        35                  40                  45

Arg Leu Leu Leu Tyr Arg Ala Ser Asn Leu Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ile Asn
                85                  90                  95

Thr Asp Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 139
<211> LENGTH: 449
<212> TYPE: PRT
<213> ORGANISM: Artificial Sequence
<220> FEATURE:
<223> OTHER INFORMATION: Synthetic Sequence_hu179-33 antibody heavy
``` chain

<400> SEQUENCE: 139

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Leu Ile Glu Trp Val Arg Gln Ala Pro Gly Gln Gly Leu Glu Trp Ile
        35                  40                  45

Gly Val Ile Asp Pro Gly Val Gly Asp Thr Asn Tyr Asn Glu Asn Phe
50                  55                  60

Lys Gly Arg Ala Thr Leu Thr Ala Asp Lys Ser Thr Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Glu Asp Asn Thr Gly Thr Ala Phe Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys
```

```
<210> SEQ ID NO 140
<211> LENGTH: 214
<212> TYPE: PRT
<213> ORGANISM: Artificial Sequence
<220> FEATURE:
<223> OTHER INFORMATION: Synthetic Sequence_hu179-33 antibody light
      chain

<400> SEQUENCE: 140

Ser Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Ser Ser Asp
            20                  25                  30

Val Thr Trp Tyr Leu Gln Lys Pro Gly Gln Ser Pro Gln Leu Leu Ile
        35                  40                  45

Tyr Tyr Val Ser Glu His Tyr Thr Gly Val Pro Asp Arg Phe Ser Gly
50                  55                  60

Ser Gly Tyr Gly Thr Asp Phe Thr Leu Lys Ile Ser Arg Val Glu Ala
65                  70                  75                  80

Glu Asp Val Gly Val Tyr Tyr Cys Gln Gln His His Arg Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 141
<211> LENGTH: 447
<212> TYPE: PRT
<213> ORGANISM: Artificial Sequence
<220> FEATURE:
<223> OTHER INFORMATION: Synthetic Sequence_hu199-36 antibody heavy
      chain

<400> SEQUENCE: 141

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
```

-continued

```
            20                  25                  30
Trp Met His Trp Val Lys Gln Ala Pro Gly Gln Gly Leu Glu Trp Met
            35                  40                  45
Gly Met Ile Asp Pro Ser Asp Ser Glu Thr Thr Leu Ile Gln Lys Phe
 50                  55                  60
Lys Asp Lys Val Thr Leu Thr Val Asp Lys Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Thr Leu Asp Gly Tyr Tyr Asp Tyr Trp Gly Gln Gly Thr Thr
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
            210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Tyr Ile Thr Arg Glu
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445
```

<210> SEQ ID NO 142
<211> LENGTH: 214
<212> TYPE: PRT
<213> ORGANISM: Artificial Sequence
<220> FEATURE:
<223> OTHER INFORMATION: Synthetic Sequence_hu199-36 antibody light chain

<400> SEQUENCE: 142

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Gln Leu Leu Val
        35                  40                  45

Tyr Phe Ala Lys Thr Leu Ala Glu Gly Val Pro Ser Arg Phe Ser Gly
    50                  55                  60

Ser Val Ser Gly Thr Gln Phe Thr Leu Thr Ile Ser Ser Leu Gln Pro
65                  70                  75                  80

Glu Asp Phe Ala Thr Tyr Tyr Cys Gln His His Tyr Gly Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 143
<211> LENGTH: 448
<212> TYPE: PRT
<213> ORGANISM: Artificial Sequence
<220> FEATURE:
<223> OTHER INFORMATION: Synthetic Sequence_AMG157 heavy chain sequence

<400> SEQUENCE: 143

```
Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Thr Arg Asp Asn Ser Lys Asn Thr Leu Asn
65                  70                  75                  80
```

-continued

Leu Gln Met Asn Ser Leu Arg Ala Glu Asp Thr Ala Val Tyr Tyr Cys
                 85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 144
<211> LENGTH: 214
<212> TYPE: PRT
<213> ORGANISM: Artificial Sequence
<220> FEATURE:
<223> OTHER INFORMATION: Synthetic Sequence_AMG157 light chain sequence

<400> SEQUENCE: 144

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
    50                  55                  60

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 145
<211> LENGTH: 371
<212> TYPE: PRT
<213> ORGANISM: Artificial Sequence
<220> FEATURE:
<223> OTHER INFORMATION: Synthetic Sequence_Amino acid sequence of human
      TSLP receptor full-length sequence

<400> SEQUENCE: 145

Met Gly Arg Leu Val Leu Leu Trp Gly Ala Ala Val Phe Leu Leu Gly
1               5                   10                  15

Gly Trp Met Ala Leu Gly Gln Gly Gly Ala Ala Glu Gly Val Gln Ile
            20                  25                  30

Gln Ile Ile Tyr Phe Asn Leu Glu Thr Val Gln Val Thr Trp Asn Ala
        35                  40                  45

Ser Lys Tyr Ser Arg Thr Asn Leu Thr Phe His Tyr Arg Phe Asn Gly
    50                  55                  60

Asp Glu Ala Tyr Asp Gln Cys Thr Asn Tyr Leu Leu Gln Glu Gly His
65                  70                  75                  80

Thr Ser Gly Cys Leu Leu Asp Ala Glu Gln Arg Asp Asp Ile Leu Tyr
                85                  90                  95

Phe Ser Ile Arg Asn Gly Thr His Pro Val Phe Thr Ala Ser Arg Trp
            100                 105                 110

Met Val Tyr Tyr Leu Lys Pro Ser Ser Pro Lys His Val Arg Phe Ser
        115                 120                 125

Trp His Gln Asp Ala Val Thr Val Thr Cys Ser Asp Leu Ser Tyr Gly
    130                 135                 140
```

```
Asp Leu Leu Tyr Glu Val Gln Tyr Arg Ser Pro Phe Asp Thr Glu Trp
145                 150                 155                 160

Gln Ser Lys Gln Glu Asn Thr Cys Asn Val Thr Ile Glu Gly Leu Asp
                165                 170                 175

Ala Glu Lys Cys Tyr Ser Phe Trp Val Arg Val Lys Ala Met Glu Asp
            180                 185                 190

Val Tyr Gly Pro Asp Thr Tyr Pro Ser Asp Trp Ser Glu Val Thr Cys
        195                 200                 205

Trp Gln Arg Gly Glu Ile Arg Asp Ala Cys Ala Glu Thr Pro Thr Pro
210                 215                 220

Pro Lys Pro Lys Leu Ser Lys Phe Ile Leu Ile Ser Ser Leu Ala Ile
225                 230                 235                 240

Leu Leu Met Val Ser Leu Leu Leu Ser Leu Trp Lys Leu Trp Arg
                245                 250                 255

Val Lys Lys Phe Leu Ile Pro Ser Val Pro Asp Pro Lys Ser Ile Phe
            260                 265                 270

Pro Gly Leu Phe Glu Ile His Gln Gly Asn Phe Gln Glu Trp Ile Thr
        275                 280                 285

Asp Thr Gln Asn Val Ala His Leu His Lys Met Ala Gly Ala Glu Gln
290                 295                 300

Glu Ser Gly Pro Glu Glu Pro Leu Val Val Gln Leu Ala Lys Thr Glu
305                 310                 315                 320

Ala Glu Ser Pro Arg Met Leu Asp Pro Gln Thr Glu Lys Glu Ala
            325                 330                 335

Ser Gly Gly Ser Leu Gln Leu Pro His Gln Pro Leu Gln Gly Gly Asp
                340                 345                 350

Val Val Thr Ile Gly Gly Phe Thr Phe Val Met Asn Asp Arg Ser Tyr
                355                 360                 365

Val Ala Leu
    370

<210> SEQ ID NO 146
<211> LENGTH: 459
<212> TYPE: PRT
<213> ORGANISM: Artificial Sequence
<220> FEATURE:
<223> OTHER INFORMATION: Synthetic Sequence_Amino acid sequence of human
      IL7R alpha full-length sequence

<400> SEQUENCE: 146

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
        50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
```

```
            115                 120                 125
Pro Glu Ala Pro Phe Asp Leu Ser Val Ile Tyr Arg Glu Gly Ala Asn
        130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
        210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
                260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
        290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
                340                 345                 350

Asp Val Val Ile Thr Pro Glu Ser Phe Gly Arg Asp Ser Ser Leu Thr
                355                 360                 365

Cys Leu Ala Gly Asn Val Ser Ala Cys Asp Ala Pro Ile Leu Ser Ser
        370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
                420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
        450                 455
```

ANTIBODY CAPABLE OF BINDING TO THYMIC STROMAL LYMPHOPOIETIN AND USE THEREOF

CROSS-REFERENCE TO RELATED APPLICATIONS

The present application is the national stage of International Patent Application No. PCT/CN2020/094154, filed on Jun. 3, 2020, which claims the benefit of and priority to Chinese Patent Application No. 201910480579.9 filed on Jun. 4, 2019, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 4, 2019, is named "702048CPUS_126268-5026-US_ST25_Sequence_Listing.TXT" and is 145 kilobytes in size.

FIELD OF THE INVENTION

The present disclosure relates to the field of antibody agents. Specifically, the present disclosure relates to anti-TSLP antibody agents and the use thereof.

BACKGROUND OF THE INVENTION

The statements herein only provide background information related to the present disclosure and do not necessarily constitute the prior art.

Asthma is a serious chronic inflammatory airway disease. There are about 334 million asthma patients worldwide and about 30 million asthma patients in China, where the mortality rate is much higher than that in developed countries. As the environment deteriorates and air pollution increases, more people may suffer from this disease, which will seriously endanger human life and health.

Thymic stromal lymphopoietin (TSLP) is an epithelial cell-derived cytokine produced in response to pro-inflammatory stimuli. It mainly promotes allergic inflammation through its activity on dendritic cells and mast cells. TSLP is a type of interleukin 7 (IL-7)-like cytokine, which was first discovered in the conditioned medium of mouse thymic stromal cells. TSLP is mainly expressed in lung, skin and intestinal epithelial cells. TSLP consists of 4 α-helices and two loops AB and CD. In the molecule, there are three pairs of disulfide bonds consisting of six cysteine, two N-glycosylation sites, and the molecular weight is about 15-20 kD. TSLP receptor is a complex consisting of two moieties, one is TSLPR and the other is IL7Rα. TSLP first binds to TSLPR with relatively low affinity, then recruits the binding of IL7Rα with high affinity, and finally activates signal pathways of stat5, etc., leading to the maturation of DCs and the differentiation of T cells.

Myeloid dendritic cells (mDCs) are the major effector cells for TSLP. TSLP acts on immature mDCs, which secrete cytokines IL-8, eotaxin-2, TARC and MDC, while highly express OX40L. In the absence of IL-12, OX40L binds into the native CD4+ T cells, leading to their differentiation into Th2 cells. Th2 cells then secrete Th2 cytokines such as IL-5, IL-4, IL-9, IL-9 and TNF, inducing Th2 inflammatory response in the body. In addition, TSLP can also induce DC cells to produce the cytokine IL-8, which recruits neutrophils in turn, leading to neutrophilic innate immune inflammation. TSLP can also induce DCs to produce eotaxin-2, which recruits eosinophils, and acts together with IL5 to make the body quickly enter the inflammatory state of eosinophil infiltration. TSLP also acts on mast cells and natural killer cells, and mediates innate inflammation by inducing the production of IL-4, IL-6, IgE, etc. In summary, TSLP can cause innate inflammation and Th2 inflammation at the same time, which in turn increases tissue mucus, remodels the airway, which leads to tracheal stenosis, and makes cell fibrosis become severe. The inflammation gradually evolves into the three major allergic diseases, asthma, allergic dermatitis and allergic rhinitis. Therefore, blocking TSLP is a potentially effective strategy for the treatment of diseases such as asthma, allergic dermatitis, etc.

Currently, anti-TSLP antibodies are disclosed in WO2008155365, WO2009035577, WO2011056772, WO2016142426 and WO2017004149. However, there is no corresponding antibody commercially available. Therefore, it is necessary to continue the development of effective medicament for treating TSLP-related diseases.

SUMMARY OF THE INVENTION

The present disclosure provides an anti-TSLP antibody.
In some embodiments, the anti-TSLP antibody as described above comprises an antibody heavy chain variable region and a light chain variable region, wherein:
i) the heavy chain variable region comprises HCDR1, HCDR2 and HCDR3 as shown in SEQ ID NO: 14, SEQ ID NO: 15 and SEQ ID NO: 47, respectively, and the light chain variable region comprises LCDR1, LCDR2 as shown in SEQ ID NO: 17, SEQ ID NO: 18, respectively, and LCDR3 as shown in SEQ ID NO: 48 or 55;
wherein, the sequence of SEQ ID NO: 47 is EDYDYDG-YAMDX$_1$, the sequence of SEQ ID NO: 48 is QQWSSX$_2$RT, the sequence of SEQ ID NO: 55 is QQSDX$_3$X$_4$RX$_5$, wherein X$_1$ is H or Y, X$_2$ is N or D, X$_3$ is N or S, X$_4$ is V or G, X$_5$ is G or E; or
ii) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 76, SEQ ID NO: 24 and SEQ ID NO: 25, respectively;
wherein, the sequence of SEQ ID NO: 76 is RASESVDX$_6$SGLSFMH, wherein, X$_6$ is selected from N, S or Q; or
iii) the heavy chain variable region comprises HCDR1, HCDR2 and HCDR3 as shown in SEQ ID NO: 26, SEQ ID NO: 96 and SEQ ID NO: 28, respectively, and the light chain variable region comprises LCDR1, LCDR2 and LCDR3 as shown in SEQ ID NO: 29, SEQ ID NO: 118 and SEQ ID NO: 31, respectively;
wherein, the sequence of SEQ ID NO: 96 is VIDPGX$_7$X$_8$DTNYNE, the sequence of SEQ ID NO: 118 is X$_9$VX$_{10}$X$_{11}$X$_{12}$X$_{13}$T, wherein X$_7$ is selected from N, Q and V, X$_8$ is G or V; X$_9$ is Y or E, X$_{10}$ is selected from S, D and E, X$_{11}$ is selected from N, Q, D and E, X$_{12}$ is selected from H, Y, D and E, X$_{13}$ is E or Y; or
iv) the heavy chain variable region comprises HCDR1, HCDR2 and HCDR3 as shown in SEQ ID NO: 32, SEQ ID NO: 33 and SEQ ID NO: 34, respectively, and the light chain variable region comprises LCDR1, LCDR2 and LCDR3 as shown in SEQ ID NO: 35, SEQ ID NO: 36 and SEQ ID NO: 37, respectively.

In some embodiments, the anti-TSLP antibody as described above comprises a heavy chain variable region and a light chain variable region, wherein:
  i) the heavy chain variable region comprises HCDR1, HCDR2 and HCDR3 as shown in SEQ ID NO: 14, SEQ ID NO: 15 and SEQ ID NO: 16, respectively, and the light chain variable region comprises LCDR1, LCDR2 and LCDR3 as shown in SEQ ID NO: 17, SEQ ID NO: 18 and SEQ ID NO: 19, respectively; or
  ii) the heavy chain variable region comprises HCDR1, HCDR2 and HCDR3 as shown in SEQ ID NO: 14, SEQ ID NO: 15 and SEQ ID NO: 45, respectively, and the light chain variable region comprises LCDR1, LCDR2 and LCDR3 as shown in SEQ ID NO: 17, SEQ ID NO: 18 and SEQ ID NO: 46, respectively; or
  iii) the heavy chain variable region comprises HCDR1, HCDR2 and HCDR3 as shown in SEQ ID NO: 14, SEQ ID NO: 15 and SEQ ID NO: 45, respectively, and the light chain variable region comprises LCDR1, LCDR2 and LCDR3 as shown in SEQ ID NO: 17, SEQ ID NO: 18 and SEQ ID NO: 53, respectively; or
  iv) the heavy chain variable region comprises HCDR1, HCDR2 and HCDR3 as shown in SEQ ID NO: 14, SEQ ID NO: 15 and SEQ ID NO: 45, respectively, and the light chain variable region comprises LCDR1, LCDR2 and LCDR3 as shown in SEQ ID NO: 17, SEQ ID NO: 18 and SEQ ID NO: 54, respectively; or
  v) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 23, SEQ ID NO: 24 and SEQ ID NO: 25, respectively; or
  vi) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 70, SEQ ID NO: 24 and SEQ ID NO: 25, respectively; or
  vii) the heavy chain variable region comprises HCDR1, HCDR2 and HCDR3 as shown in SEQ ID NO: 20, SEQ ID NO: 21 and SEQ ID NO: 22, respectively, and the light chain variable region comprises LCDR1, LCDR2 and LCDR3 as shown in SEQ ID NO: 71, SEQ ID NO: 24 and SEQ ID NO: 25, respectively; or
  viii) the heavy chain variable region comprises HCDR1 and HCDR3 as shown in SEQ ID NO: 26, SEQ ID NO: 28, respectively, and HCDR2 as shown in SEQ ID NO: 27, 93, 94 or 95, and the light chain variable region comprises LCDR1 and LCDR3 as shown in SEQ ID NO: 29, SEQ ID NO: 31, respectively, and LCDR2 as shown in SEQ ID NO: 30, 108, 109, 110, 111, 112, 113, 114, 115, 116 or 117.

In some embodiments, the anti-TSLP antibody as described above comprises a heavy chain variable region and a light chain variable region, wherein:
  a) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
  b) the heavy chain variable region comprises HCDR1, HCDR2 and HCDR3 as shown in SEQ ID NO: 26, SEQ ID NO: 93 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
  c) the heavy chain variable region comprises HCDR1, HCDR2 and HCDR3 as shown in SEQ ID NO: 26, SEQ ID NO: 94 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
  d) the heavy chain variable region comprises HCDR1, HCDR2 and HCDR3 as shown in SEQ ID NO: 26, SEQ ID NO: 95 and SEQ ID NO: 28, respectively, and the light chain variable region comprises LCDR1, LCDR2 and LCDR3 as shown in SEQ ID NO: 29, SEQ ID NO: 30 and SEQ ID NO: 31, respectively; or
  e) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 108 and SEQ ID NO: 31, respectively; or
  f) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 109 and SEQ ID NO: 31, respectively; or
  g) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 110 and SEQ ID NO: 31, respectively; or
  h) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 111 and SEQ ID NO: 31, respectively; or
  i) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 112 and SEQ ID NO: 31, respectively; or
  j) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 113 and SEQ ID NO: 31, respectively; or
  k) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 114 and SEQ ID NO: 31, respectively; or
  l) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 115 and SEQ ID NO: 31, respectively; or
  m) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 116 and SEQ ID NO: 31, respectively; or n) the heavy chain variable region comprises HCDR1, HCDR2 and HCDR3 as shown in SEQ ID NO: 26, SEQ ID NO: 27 and SEQ ID NO: 28, respectively, and the light chain variable region comprises LCDR1, LCDR2 and LCDR3 as shown in SEQ ID NO: 29, SEQ ID NO: 117 and SEQ ID NO: 31, respectively.

In some embodiments of the anti-TSLP antibody as described above, the anti-TSLP antibody is a murine antibody, a chimeric antibody or a humanized antibody.

In some embodiments of the anti-TSLP antibody as described above, the anti-TSLP antibody comprises framework region(s) derived from a human antibody, or the anti-TSLP antibody comprises a light chain variable region and/or a heavy chain variable region selected from those described in (a), (b), (c) or (d) below:

a) the heavy chain variable region comprises HCDR1 and HCDR2 as shown in SEQ ID NO: 14, SEQ ID NO: 15, respectively, and HCDR3 as shown in SEQ ID NO: 16 or 45, and the framework region(s) thereof comprise(s) at most 10 back mutations, preferably, the back mutation is selected from one or more of 38K, 48I, 67A, 69L, 71V and 73K; and/or the light chain variable region comprises LCDR1 and LCDR2 as shown in SEQ ID NO: 17, SEQ ID NO: 18, respectively, and LCDR3 as shown in SEQ ID NO: 19, 46, 53 or 54, and the framework region(s) thereof comprise(s) at most 10 amino acid back mutations, preferably, the back mutation is selected from one or more of 46P, 47W, 58V, 70S and 71Y;

b) the heavy chain variable region comprises HCDR1, HCDR2 and HCDR3 as shown in SEQ ID NO: 20, SEQ ID NO: 21 and SEQ ID NO: 22, respectively, and the framework region(s) thereof comprise(s) at most 10 back mutations, preferably, the back mutation is selected from one or more of 2A, 27F, 38K, 39H, 48I, 67A, 69L, 71V and 76R; and/or the light chain variable region comprises LCDR2 and LCDR3 as shown in SEQ ID NO: 24, SEQ ID NO: 25, respectively, and LCDR1 as shown in SEQ ID NO: 23, 70 or 71, and the framework region(s) thereof comprise(s) at most 10 amino acid back mutations, preferably, the back mutation is one or more of 1D, 4L, 43P, 48L and 58I;

c) the heavy chain variable region comprises HCDR1 and HCDR3 as shown in SEQ ID NO: 26, SEQ ID NO: 28, respectively, and HCDR2 as shown in SEQ ID NO: 27, 93, 94 or 95, and the framework region(s) thereof comprise(s) at most 10 back mutations, preferably, the back mutation is selected from one or more of 27Y, 28A, 38K, 48I, 66K, 67A, 69L, 80I and 82b R; and/or the light chain variable region comprises LCDR1 and LCDR3 as shown in SEQ ID NO: 29, SEQ ID NO: 31, respectively, and LCDR2 as shown in SEQ ID NO: 30, 108, 109, 110, 111, 112, 113, 114, 115, 116 or 117, and the framework region(s) thereof comprise(s) at most 10 back mutations, preferably, the back mutation is selected from one or more of 1S, 43S, 67Y and 73F; or d) the heavy chain variable region comprises HCDR1, HCDR2 and HCDR3 as shown in SEQ ID NO: 32, SEQ ID NO: 33 and SEQ ID NO: 34, respectively, and the framework region(s) thereof comprise(s) at most 10 back mutations, preferably, the back mutation is selected from one or more of 38K, 48I, 66K, 67A, 69L, 71V, 73K and 78A; and/or the light chain variable region comprises LCDR1, LCDR2 and LCDR3 as shown in SEQ ID NO: 35, SEQ ID NO: 36 and SEQ ID NO: 37, respectively, and the framework region(s) thereof comprise(s) at most 10 back mutations, preferably, the back mutation is selected from one or more of 43S, 45Q, 48V, 66V and 70Q.

In some embodiments, the anti-TSLP antibody as described above comprises a heavy chain variable region and a light chain variable region, wherein:

i) the heavy chain variable region has at least 90%, 92%, 94%, 95%, 96%, 97%, 98% or 99% sequence identity with the heavy chain variable region as shown in amino acid sequence SEQ ID NO: 6, 42, 43, 44 or 50, and the light chain variable region has at least 90%, 92%, 94%, 95%, 96%, 97%, 98% or 99% sequence identity with the light chain variable region as shown in amino acid sequence SEQ ID NO: 7, 38, 39, 40, 41, 49, 51 or 52; or ii) the heavy chain variable region has at least 90%, 92%, 94%, 95%, 96%, 97%, 98% or 99% sequence identity with the heavy chain variable region as shown in amino acid sequence SEQ ID NO: 8, 62, 63, 64, 65, 66, 67, 68 or 69, and the light chain variable region has at least 90%, 92%, 94%, 95%, 96%, 97%, 98% or 99% sequence identity with the light chain variable region as shown in amino acid sequence SEQ ID NO: 9, 56, 57, 58, 59, 60, 61, 72, 73, 74 or 75; or iii) the heavy chain variable region has at least 90%, 92%, 94%, 95%, 96%, 97%, 98% or 99% sequence identity with the heavy chain variable region as shown in amino acid sequence SEQ ID NO: 10, 85, 86, 87, 88, 89, 90, 91, 92 or 97, and the light chain variable region has at least 90%, 92%, 94%, 95%, 96%, 97%, 98% or 99% sequence identity with the light chain variable region as shown in amino acid sequence SEQ ID NO: 11, 77, 78, 79, 80, 81, 82, 83, 84, 98, 99, 100, 101, 102, 103, 104, 105, 106, 107 or 119; or iv) the heavy chain variable region has at least 90%, 92%, 94%, 95%, 96%, 97%, 98% or 99% sequence identity with the heavy chain variable region as shown in amino acid sequence SEQ ID NO: 12, 126, 127, 128, 129, 130, 131 or 132, and the light chain variable region has at least 90%, 92%, 94%, 95%, 96%, 97%, 98% or 99% sequence identity with the light chain variable region as shown in amino acid sequence SEQ ID NO: 13, 120, 121, 122, 123, 124 or 125.

In some embodiments of the anti-TSLP antibody as described above, the anti-TSLP antibody is a humanized antibody, which comprises framework region(s) derived from a human antibody or a framework region variant thereof, said framework region variant has at most 1, 2, 3, 4, 5, 6, 7, 8, 9 or 10 amino acid back mutations in the light chain framework region(s) and/or heavy chain framework region(s) of the human antibody, respectively.

In some embodiments of the anti-TSLP antibody as described above, the framework region variant comprises back mutations selected from those described in (a), (b), (c) or (d) below:

a) one or more amino acid back mutations selected from the group consisting of 46P, 47W, 58V, 70S and 71Y comprised in the framework region(s) of the light chain variable region as shown in SEQ ID NO: 38, 49, 51 or 52, and/or one or more amino acid back mutations selected from the group consisting of 38K, 48I, 67A, 69L, 71V and 73K comprised in the framework region (s) of the heavy chain variable region as shown in SEQ ID NO: 42 or 50;

b) one or more amino acid back mutations selected from the group consisting of 1D, 4L, 43P, 48L and 58I comprised in the framework region(s) of the light chain variable region as shown in SEQ ID NO: 56, 59, 72, 73, 74 or 75, and/or one or more amino acid back mutations selected from the group consisting of 2A, 27F, 38K, 39H, 48I, 67A, 69L, 71V and 76R comprised in the framework region(s) of the heavy chain variable region as shown in SEQ ID NO: 62;

c) one or more amino acid back mutations selected from the group consisting of 1S, 43S, 67Y and 73F comprised in the framework region(s) of the light chain variable region as shown in SEQ ID NO: 77, 81, 98, 99, 100, 101, 102, 103, 104, 105, 106, 107 or 119, and/or one or more amino acid back mutations selected from the group consisting of 27Y, 28A, 38K, 48I, 66K, 67A, 69L, 80I and 82b R comprised in the framework region(s) of the heavy chain variable region as shown in SEQ ID NO: 85, 90, 91, 92 or 97;

d) one or more amino acid back mutations selected from the group consisting of 43S, 45Q, 48V, 66V and 70Q comprised in the framework region(s) of the light chain variable region as shown in SEQ ID NO: 120, and/or one or more amino acid back mutations selected from the group consisting of 38K, 48I, 66K, 67A, 69L, 71V, 73K and 78A comprised in the framework region of the heavy chain variable region as shown in SEQ ID NO: 126.

In some embodiments, the anti-TSLP antibody as described above comprises a heavy chain variable region and a light chain variable region, wherein:

i) the amino acid sequence of the heavy chain variable region is as shown in SEQ ID NO: 6, 42, 43, 44 or 50, and the amino acid sequence of the light chain variable region is as shown in SEQ ID NO: 7, 38, 39, 40, 41, 49, 51 or 52; or ii) the amino acid sequence of the heavy chain variable region is as shown in SEQ ID NO: 8, 62, 63, 64, 65, 66, 67, 68 or 69, and the amino acid sequence of the light chain variable region is as shown in SEQ ID NO: 9, 56, 57, 58, 59, 60, 61, 72, 73, 74 or 75; or iii) the amino acid sequence of the heavy chain variable region is as shown in SEQ ID NO: 10, 85, 86, 87, 88, 89, 90, 91, 92 or 97, and the amino acid sequence of the light chain variable region is as shown in SEQ ID NO: 11, 77, 78, 79, 80, 81, 82, 83, 84, 98, 99, 100, 101, 102, 103, 104, 105, 106, 107 or 119; or iv) the amino acid sequence of the heavy chain variable region is as shown in SEQ ID NO: 12, 126, 127, 128, 129, 130, 131 or 132, and the amino acid sequence of the light chain variable region is as shown in SEQ ID NO: 13, 120, 121, 122, 123, 124 or 125.

In some embodiments, the anti-TSLP antibody as described above comprises a heavy chain variable region and a light chain variable region as shown below:

(a) the sequence of the heavy chain variable region is as shown in SEQ ID NO: 6, and the sequence of the light chain variable region is as shown in SEQ ID NO: 7;

(b) the sequence of the heavy chain variable region is as shown in SEQ ID NO: 42, 43 or 44, and the sequence of the light chain variable region is as shown in SEQ ID NO: 39, 40 or 41;

(c) the sequence of the heavy chain variable region is as shown in SEQ ID NO: 43, and the sequence of the light chain variable region is as shown in SEQ ID NO: 38;

(d) the sequence of the heavy chain variable region is as shown in SEQ ID NO: 50, and the sequence of the light chain variable region is as shown in SEQ ID NO: 49, 51 or 52;

(e) the sequence of the heavy chain variable region is as shown in SEQ ID NO: 8, and the sequence of the light chain variable region is as shown in SEQ ID NO: 9;

(f) the sequence of the heavy chain variable region is as shown in SEQ ID NO: 62, 63, 64 or 65, and the sequence of the light chain variable region is as shown in SEQ ID NO: 56, 57 or 58;

(g) the sequence of the heavy chain variable region is as shown in SEQ ID NO: 64, 66, 67, 68 or 69, and the sequence of the light chain variable region is as shown in SEQ ID NO: 59, 60 or 61;

(h) the sequence of the heavy chain variable region is as shown in SEQ ID NO: 64, and the sequence of the light chain variable region is as shown in SEQ ID NO: 72 or 73;

(i) the sequence of the heavy chain variable region is as shown in SEQ ID NO: 69, and the sequence of the light chain variable region is as shown in SEQ ID NO: 74;

(j) the sequence of the heavy chain variable region is as shown in SEQ ID NO: 10, and the sequence of the light chain variable region is as shown in SEQ ID NO: 11;

(k) the sequence of the heavy chain variable region is as shown in SEQ ID NO: 85, and the sequence of the light chain variable region is as shown in SEQ ID NO: 77, 78, 102 or 104;

(l) the sequence of the heavy chain variable region is as shown in SEQ ID NO: 86 or 88, and the sequence of the light chain variable region is as shown in SEQ ID NO: 77 or 78;

(m) the sequence of the heavy chain variable region is as shown in SEQ ID NO: 87, and the sequence of the light chain variable region is as shown in SEQ ID NO: 77, 78, 79, 81, 82, 83, 84, 98, 99, 100, 101, 103, 105, 106 or 107;

(n) the sequence of the heavy chain variable region is as shown in SEQ ID NO: 89, and the sequence of the light chain variable region is as shown in SEQ ID NO: 79, 81, 82, 83 or 84;

(o) the sequence of the heavy chain variable region is as shown in SEQ ID NO: 90, 91 or 92, and the sequence of the light chain variable region is as shown in SEQ ID NO: 78;

(p) the sequence of the heavy chain variable region is as shown in SEQ ID NO: 97, and the sequence of the light chain variable region is as shown in SEQ ID NO: 119;

(q) the sequence of the heavy chain variable region is as shown in SEQ ID NO: 12, and the sequence of the light chain variable region is as shown in SEQ ID NO: 13;

(r) the sequence of the heavy chain variable region is as shown in SEQ ID NO: 127, 128, 129, 130, 131 or 132, and the sequence of the light chain variable region is as shown in SEQ ID NO: 120, 121, 123, 124 or 125; or (s) the sequence of the heavy chain variable region is as shown in SEQ ID NO: 132, and the sequence of the light chain variable region is as shown in SEQ ID NO: 125.

In some embodiments of the anti-TSLP antibody as described above, the combinations of the light chain variable region and the heavy chain variable region of the antibodies are shown as follows:

TABLE 1

Combinations of the light and heavy chain variable regions of the mAb3 humanized antibodies

| Antibody | VH (SEQ ID NO) | VL (SEQ ID NO) |
|---|---|---|
| hu3-01 | 42 | 39 |
| hu3-02 | 42 | 40 |
| hu3-03 | 42 | 41 |
| hu3-04 | 43 | 38 |
| hu3-05 | 43 | 39 |
| hu3-06 | 43 | 40 |
| hu3-07 | 43 | 41 |
| hu3-08 | 44 | 39 |
| hu3-09 | 44 | 40 |
| hu3-10 | 44 | 41 |
| hu3-11 | 50 | 49 |
| hu3-12 | 50 | 51 |
| hu3-13 | 50 | 52 |

TABLE 2

Combinations of the light and heavy chain variable regions of the mAb119 humanized antibodies

| Antibody | VH (SEQ ID NO) | VL (SEQ ID NO) |
|---|---|---|
| hu119-01 | 62 | 56 |
| hu119-02 | 63 | 56 |
| hu119-03 | 64 | 56 |
| hu119-04 | 65 | 56 |
| hu119-05 | 62 | 57 |
| hu119-06 | 63 | 57 |
| hu119-07 | 64 | 57 |
| hu119-08 | 65 | 57 |
| hu119-09 | 62 | 58 |
| hu119-10 | 63 | 58 |
| hu119-11 | 64 | 58 |
| hu119-12 | 65 | 58 |
| hu119-13 | 64 | 59 |
| hu119-14 | 66 | 59 |
| hu119-15 | 67 | 59 |
| hu119-16 | 68 | 59 |
| hu119-17 | 69 | 59 |
| hu119-18 | 64 | 60 |
| hu119-19 | 66 | 60 |
| hu119-20 | 67 | 60 |
| hu119-21 | 68 | 60 |
| hu119-22 | 69 | 60 |
| hu119-23 | 64 | 61 |
| hu119-24 | 66 | 61 |
| hu119-25 | 67 | 61 |
| hu119-26 | 68 | 61 |
| hu119-27 | 69 | 61 |
| hu119-28 | 64 | 72 |
| hu119-29 | 64 | 73 |
| hu119-30 | 69 | 74 |

TABLE 3

Combinations of the light and heavy chain variable regions of the mAb179 humanized antibodies

| Antibody | VH (SEQ ID NO) | VL (SEQ ID NO) |
|---|---|---|
| hu179-01 | 85 | 77 |
| hu179-02 | 85 | 78 |
| hu179-03 | 86 | 77 |
| hu179-04 | 86 | 78 |
| hu179-05 | 87 | 77 |
| hu179-06 | 87 | 78 |
| hu179-07 | 87 | 79 |
| hu179-08 | 87 | 81 |
| hu179-09 | 87 | 82 |
| hu179-10 | 87 | 83 |
| hu179-11 | 87 | 84 |
| hu179-12 | 88 | 77 |
| hu179-13 | 88 | 78 |
| hu179-14 | 89 | 79 |
| hu179-15 | 89 | 80 |
| hu179-16 | 89 | 81 |
| hu179-17 | 89 | 82 |
| hu179-18 | 89 | 83 |
| hu179-19 | 89 | 84 |
| hu179-20 | 90 | 78 |
| hu179-21 | 91 | 78 |
| hu179-22 | 92 | 78 |
| hu179-23 | 85 | 102 |
| hu179-24 | 85 | 104 |
| hu179-25 | 87 | 98 |
| hu179-26 | 87 | 99 |
| hu179-27 | 87 | 100 |
| hu179-28 | 87 | 101 |
| hu179-29 | 87 | 103 |
| hu179-30 | 87 | 105 |
| hu179-31 | 87 | 106 |
| hu179-32 | 87 | 107 |
| hu179-33 | 97 | 119 |

TABLE 4

Combinations of the light and heavy chain variable regions of the mAb199 humanized antibodies

| Antibody | VH (SEQ ID NO) | VL (SEQ ID NO) |
|---|---|---|
| hu199-01 | 127 | 120 |
| hu199-02 | 127 | 121 |
| hu199-03 | 127 | 122 |
| hu199-04 | 127 | 123 |
| hu199-05 | 127 | 124 |
| hu199-06 | 127 | 125 |
| hu199-07 | 128 | 120 |
| hu199-08 | 128 | 121 |
| hu199-09 | 128 | 122 |
| hu199-10 | 128 | 123 |
| hu199-11 | 128 | 124 |
| hu199-12 | 128 | 125 |
| hu199-13 | 129 | 120 |
| hu199-14 | 129 | 121 |
| hu199-15 | 129 | 122 |
| hu199-16 | 129 | 123 |
| hu199-17 | 129 | 124 |
| hu199-18 | 129 | 125 |
| hu199-19 | 130 | 120 |
| hu199-20 | 130 | 121 |
| hu199-21 | 130 | 122 |
| hu199-22 | 130 | 123 |
| hu199-23 | 130 | 124 |
| hu199-24 | 130 | 125 |
| hu199-25 | 131 | 120 |
| hu199-26 | 131 | 121 |
| hu199-27 | 131 | 122 |
| hu199-28 | 131 | 123 |
| hu199-29 | 131 | 124 |
| hu199-30 | 131 | 125 |
| hu199-31 | 132 | 120 |
| hu199-32 | 132 | 121 |
| hu199-33 | 132 | 122 |
| hu199-34 | 132 | 123 |
| hu199-35 | 132 | 124 |
| hu199-36 | 132 | 125 |

In some embodiments of the anti-TSLP antibody as described above, the antibody further comprises antibody constant region(s); preferably, the heavy chain constant region of the antibody constant regions is selected from the group consisting of human IgG1, IgG2, IgG3 and IgG4 constant regions and conventional variants thereof, the light chain constant region of the antibody constant regions is selected from the group consisting of human antibody κ and λ chain constant regions and conventional variants thereof; more preferably, the antibody comprises the heavy chain constant region as shown in sequence SEQ ID NO: 133, and the light chain constant region as shown in sequence SEQ ID NO: 134.

In some embodiments, the anti-TSLP antibody as described above comprises a heavy chain and a light chain as shown below:
(a) the amino acid sequence of the heavy chain is as shown in SEQ ID NO: 135 or has at least 90%, 92%, 94%, 95%, 96%, 97%, 98% or 99% sequence identity with the same, and the amino acid sequence of the light chain is as shown in SEQ ID NO: 136 or has at least 90%, 92%, 94%, 95%, 96%, 97%, 98% or 99% sequence identity with the same;
(b) the amino acid sequence of the heavy chain is as shown in SEQ ID NO: 137 or has at least 90%, 92%, 94%, 95%, 96%, 97%, 98% or 99% sequence identity with the same, and the amino acid sequence of the light chain is as shown in SEQ ID NO: 138 or has at least 90%, 92%, 94%, 95%, 96%, 97%, 98% or 99% sequence identity with the same;
(c) the amino acid sequence of the heavy chain is as shown in SEQ ID NO: 139 or has at least 90%, 92%, 94%, 95%, 96%, 97%, 98% or 99% sequence identity with the same, and the amino acid sequence of the light chain is as shown in SEQ ID NO: 140 or has at least 90% sequence identity with the same; or
(d) the amino acid sequence of the heavy chain is as shown in SEQ ID NO: 141 or has at least 90%, 92%, 94%, 95%, 96%, 97%, 98% or 99% sequence identity with the same, and the amino acid sequence of the light chain is as shown in SEQ ID NO: 142 or has at least 90%, 92%, 94%, 95%, 96%, 97%, 98% or 99% sequence identity with the same.

In some embodiments, the anti-TSLP antibody as described above comprises a heavy chain and a light chain as shown below:
(a) the amino acid sequence of the heavy chain is as shown in SEQ ID NO: 135, and the amino acid sequence of the light chain is as shown in SEQ ID NO: 136;
(b) the amino acid sequence of the heavy chain is as shown in SEQ ID NO: 137, and the amino acid sequence of the light chain is as shown in SEQ ID NO: 138;
(c) the amino acid sequence of the heavy chain is as shown in SEQ ID NO: 139, and the amino acid sequence of the light chain is as shown in SEQ ID NO: 140; or
(d) the amino acid sequence of the heavy chain is as shown in SEQ ID NO: 141, and the amino acid sequence of the light chain is as shown in SEQ ID NO: 142.

In some embodiments, the antibody competitively binds to human TSLP with the anti-TSLP antibody as described above or antigen-binding fragment thereof.

In another aspect, the present disclosure also provides a nucleic acid molecule encoding the anti-TSLP antibody as described above.

In another aspect, the present disclosure also provides an expression vector comprising the nucleic acid molecule as described above.

In another aspect, the present disclosure also provides a host cell comprising the nucleic acid molecule as described above or the expression vector as described above, preferably, the cell is a bacterial cell, a fungal cell, an insect animal cell or a mammalian cell.

In some embodiments, the present disclosure provides a method for preparing the TSLP antibody as described above.

In some embodiments, the present disclosure provides a pharmaceutical composition containing a therapeutically effective amount of the anti-TSLP antibody as described above, or the nucleic acid molecule as described above, or the host cell as described above, as well as one or more pharmaceutically acceptable carriers, diluents, buffers or excipients. Preferably, the therapeutically effective amount means 0.1-3000 mg or 1-1000 mg of the anti-TSLP antibody as described above contained in a unit dose of the composition.

In some embodiments, the present disclosure provides a method for immunodetection or determination of TSLP in vitro or ex vivo, which comprises a step of using the anti-TSLP antibody as described above.

In some embodiments, the present disclosure provides use of the anti-TSLP antibody as described above in preparing reagents for immunodetection of human TSLP.

In some embodiments, the present disclosure provides an anti-TSLP antibody as described above for use in immunodetection or determination of TSLP.

In some embodiments, the present disclosure provides a kit comprising the anti-TSLP antibody as described above.

In some embodiments, the present disclosure provides use of the anti-TSLP antibody as described above, or the nucleic acid molecule as described above, or the host cell as described above or the pharmaceutical composition as described above, in preparing a medicament for treating TSLP-related diseases: wherein the TSLP-related disease includes, but is not limited to: asthma, idiopathic pulmonary fibrosis, atopic dermatitis, allergic conjunctivitis, allergic rhinitis, allergic sinusitis, urticaria, Netherton syndrome, eosinophilic esophagitis, food allergy, allergic diarrhea, eosinophilic gastroenteritis, allergic bronchopulmonary aspergillosis, allergic fungal sinusitis, chronic pruritus, cancer, breast cancer, colon cancer, lung cancer, ovarian cancer, prostate cancer, rheumatoid arthritis, chronic obstructive pulmonary disease, systemic sclerosis, multiple sclerosis, keloidosis, ulcerative colitis, nasal polyposis, chronic eosinophilic pneumonia, eosinophilic bronchitis, celiac disease, Churg-Strauss syndrome, eosinophilic myalgia syndrome, hypereosinophilic syndrome, eosinophilic granulomatosis with polyangiitis, inflammatory bowel disease, scleroderma, interstitial lung disease, fibrosis caused by chronic hepatitis B or C, fibrosis induced by radiation and fibrosis caused by wound healing.

In some embodiments, the present disclosure provides a method for treating TSLP-related diseases, which comprises administering to a subject a therapeutically effective amount of the anti-TSLP antibody as described above, or the nucleic acid molecule as described above, or the host cell as described above or the pharmaceutical composition as described above; asthma, idiopathic pulmonary fibrosis, atopic dermatitis, allergic conjunctivitis, allergic rhinitis, allergic sinusitis, urticaria, Netherton syndrome, eosinophilic esophagitis, food allergy, allergic diarrhea, eosinophilic gastroenteritis, allergic bronchopulmonary aspergillosis, allergic fungal sinusitis, chronic pruritus, cancer, breast cancer, colon cancer, lung cancer, ovarian cancer, prostate cancer, rheumatoid arthritis, chronic obstructive pulmonary disease, systemic sclerosis, multiple sclerosis, keloidosis, ulcerative colitis, nasal polyposis, chronic eosinophilic pneumonia, eosinophilic bronchitis, celiac disease, Churg-Strauss syndrome, eosinophilic myalgia syndrome, hypereosinophilic syndrome, eosinophilic granulomatosis with polyangiitis, inflammatory bowel disease, scleroderma, interstitial lung disease, fibrosis caused by chronic hepatitis B or C, fibrosis induced by radiation and fibrosis caused by wound healing.

In some embodiments, the present disclosure provides an anti-TSLP antibody for use as a medicament, wherein the anti-TSLP antibody is for use in treating TSLP-related diseases, wherein the TSLP-related disease includes, but is not limited to: asthma, idiopathic pulmonary fibrosis, atopic dermatitis, allergic conjunctivitis, allergic rhinitis, allergic sinusitis, urticaria, Netherton syndrome, eosinophilic esophagitis, food allergy, allergic diarrhea, eosinophilic gastroenteritis, allergic bronchopulmonary aspergillosis, allergic fungal sinusitis, chronic pruritus, cancer, breast cancer, colon cancer, lung cancer, ovarian cancer, prostate cancer, rheumatoid arthritis, chronic obstructive pulmonary disease, systemic sclerosis, multiple sclerosis, keloidosis, ulcerative colitis, nasal polyposis, chronic eosinophilic pneumonia, eosinophilic bronchitis, celiac disease, Churg-Strauss syndrome, eosinophilic myalgia syndrome, hypereosinophilic syndrome, eosinophilic granulomatosis with polyangiitis, inflammatory bowel disease, scleroderma, interstitial lung disease, fibrosis caused by chronic hepatitis B or C, fibrosis induced by radiation and fibrosis caused by wound healing.

DETAILED DESCRIPTION OF THE DISCLOSURE

Detailed Description of the Invention

Terminology

Figure 1:
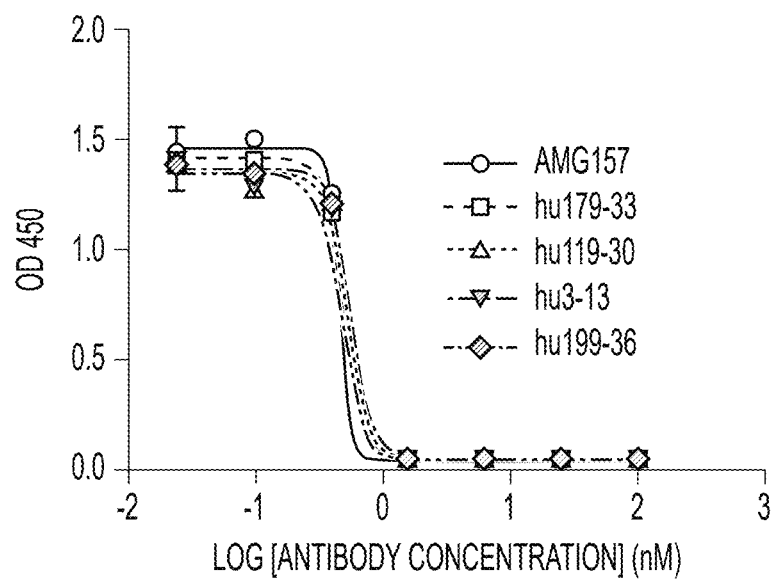
FIG. 1: The result of the antibody blocking the binding activity of TSLP to TSLP receptor.
Figure 2:
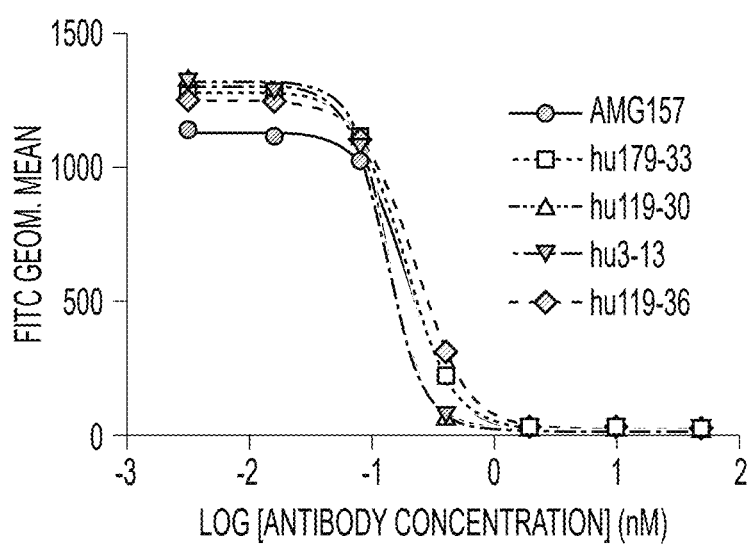
FIG. 2: The result of the antibody blocking the binding activity of TSLP to cell surface TSLP receptor.

To make the present disclosure easier to be understood, certain technical and scientific terms are specifically defined below. Unless clearly defined otherwise herein, all other technical and scientific terms used herein have the meanings commonly understood by those of ordinary skill in the art to which the present disclosure belongs.

The three-letter codes and one-letter codes of amino acids used in the present disclosure are as described in J. biol. chem, 243, p 3558 (1968).

The term "Thymic Stromal Lymphopoietin (TSLP)" is a type I cytokine with four α-helix bundle, and also known as an epithelial cell-derived cytokine produced in response to pro-inflammatory stimuli. It is closely related to interleukin-7 (IL-7), initiates allergic reactions by stimulating dendritic cells (DCs), and is an important factor in regulating the immune response in the human body. The term "TSLP" includes variants, isoforms, homologs, orthologs and paralogues of TSLP.

The "antibody" described in the present disclosure refers to an immunoglobulin, generally, the intact antibody is a tetrapeptide chain structure composed of two identical heavy chains and two identical light chains linked by interchain disulfide bonds. Immunoglobulin heavy chain constant regions exhibit different amino acid compositions and rank orders, hence present different antigenicity. Accordingly, immunoglobulins can be divided into five types, or named as immunoglobulin isotypes, namely IgM, IgD, IgG, IgA and IgE, and the corresponding heavy chains are p chain, δ chain, y chain, a chain and F chain, respectively. The same type of Ig can be further divided into different subclasses according to the difference in the amino acid composition of the hinge region and the number and position of heavy chain disulfide bonds. For example, IgG can be divided into IgG1, IgG2, IgG3 and IgG4. The light chain is divided into κ chain or λ chain by the difference of the constant region. Each of the five types of Ig can have κ chain or λ chain.

The sequence of about 110 amino acids near the N-terminus of the antibody heavy and light chains varies greatly and known as the variable region (Fv region); the remaining amino acid sequence near the C-terminus is relatively stable and is the constant region. The variable region includes 3 hypervariable regions (HVR) and 4 framework regions (FR) with relatively conservative sequences. The 3 hypervariable regions determine the specificity of the antibody, and is also known as complementarity determining regions (CDR). Each light chain variable region (VL) and heavy chain variable region (VH) consists of 3 CDR regions and 4 FR regions. The order from the amino terminus to the carboxy terminus is: FR1, CDR1, FR2, CDR2, FR3, CDR3, FR4. The 3 CDR regions of the light chain refer to LCDR1, LCDR2 and LCDR3; the 3 CDR regions of the heavy chain refer to HCDR1, HCDR2 and HCDR3.

The antibodies of the present disclosure include murine antibodies, chimeric antibodies and humanized antibodies.

The term "murine antibody" in the present disclosure refers to a monoclonal antibody against human TSLP prepared according to the knowledge and skills in the art. During preparation, the test subject is injected with TSLP antigen, and then hybridomas expressing antibodies with the desired sequence or functional properties are isolated. In a preferred embodiment of the present disclosure, the murine anti-TSLP antibody or antigen-binding fragment thereof may further comprise a light chain constant region of murine κ, λ chain or variants thereof, or further comprise a heavy chain constant region of murine IgG1, IgG2, IgG3 or variants thereof.

The term "chimeric antibody" is an antibody formed by fusing the variable region of a murine antibody with the constant region of a human antibody, which can alleviate the immune response induced by murine antibody. Establishing a chimeric antibody requires first establishing a hybridoma secreting murine specific monoclonal antibodies, then cloning the variable region gene from the murine hybridoma cells, and then cloning the constant region gene of the human antibody as necessary, linking the murine variable region gene with the human constant region gene to form a chimeric gene to be inserted into an expression vector, and finally expressing the chimeric antibody molecule in a eukaryotic system or a prokaryotic system. In a preferred embodiment of the present disclosure, the antibody light chain of the TSLP chimeric antibody further comprises a light chain constant region of a human κ, λ chain or variant thereof. The antibody heavy chain of the TSLP chimeric antibody further comprises the heavy chain constant region of human IgG1, IgG2, IgG3, IgG4 or variant thereof, preferably comprises the heavy chain constant region of human IgG1, IgG2 or IgG4, or IgG1, IgG2, or IgG4 variants with amino acid mutations (for example L234A and/or L235A mutations, and/or S228P mutations).

The term "humanized antibody", also known as CDR-grafted antibody, refers to the antibody produced by grafting murine CDR sequences into the framework of human antibody variable regions, that is, an antibody produced in different types of human germline antibody framework sequences. It can overcome the heterogeneous reaction induced by the chimeric antibody as it carries a large amount of murine protein components. Such framework sequences can be obtained from public DNA databases or published references that include germline antibody gene sequences. For example, the germline DNA sequences of the human heavy chain and light chain variable region genes can be found in the "VBase" human germline sequence database (available on the Internet www.mrccpe.com.ac.uk/vbase), as well as in Kabat, E. A., et al., 1991, Sequences of Proteins of Immunological Interest, 5th edition. In order to avoid the decrease in activity at the same time caused by the decrease in immunogenicity, the human antibody variable region framework sequence can be subjected to minimal reverse mutations or back mutations to maintain activity. The humanized antibody of the present disclosure also includes humanized antibodies on which CDR affinity maturation is performed by yeast display.

CDR grafting may result in reduced affinity of the produced antibody or antigen-binding fragment thereof to the antigen due to changes of the framework residues in contact with the antigen. Such interactions may be the result of hypermutation of somatic cells. Therefore, it may still be necessary to graft such donor framework amino acids to the framework of the humanized antibody. The amino acid residues involved in antigen binding and from non-human antibodies or antigen-binding fragments thereof can be identified by examining the sequence and structure of the animal monoclonal antibody variable region. Residues in the CDR donor framework that differ from the germline can be considered related. If the closest germline cannot be determined, the sequence can be compared with the consensus sequence of a subclass or animal antibody sequence with a high percentage of similarity. Rare framework residues are thought to be the result of hypermutation of somatic cells and thus play an important role in binding.

In one embodiment of the present disclosure, the antibody or antigen-binding fragment thereof may further comprise the light chain constant region of human or murine κ, λ chain or variant thereof, or further comprise the heavy chain constant region of human or murine IgG1, IgG2, IgG3, IgG4 or variant thereof, preferably comprising the heavy chain constant region of human IgG1, IgG2 or IgG4, or IgG1, IgG2 or IgG4 variants with amino acid mutations (for example L234A/L235A mutation, S228P mutation, YTE mutation).

The "conventional variant" of the human antibody heavy chain constant region and the human antibody light chain constant region described in the present disclosure refer to the variant of heavy chain constant region or light chain constant region that has been disclosed in the prior art and does not change the structure and function of the antibody variable region. Exemplary variants include IgG1, IgG2, IgG3 or IgG4 heavy chain constant region variants with site-directed modifications and amino acid substitutions of the heavy chain constant region. Specific substitutions are such as YTE mutations, L234A and/or L235A mutations, S228P mutations, and/or mutations to obtain a knob-into-hole structure (making the antibody heavy chain have a combination of knob-Fc and hole-Fc) known in the art. These mutations have been confirmed to make the antibody have new properties, but does not change the function of the antibody variable region.

"Human antibody (HuMAb)", "antibody derived from human", "fully human antibody" and "completely human antibody" can be used interchangeably, and can be antibodies derived from humans or antibodies obtained from a genetically modified organism which has been "engineered" to produce specific human antibodies in response to antigen stimulation and can be produced by any method known in the art. In some technologies, the elements of human heavy chain and light chain gene loci are introduced into cell lines of organisms derived from embryonic stem cell lines, in which the endogenous heavy chain and light chain genetic loci are target disrupted. Transgenic organisms can synthesize human antibodies specific to human antigens, and the organisms can be used to produce human antibody-secreting hybridomas. A human antibody can also be an antibody in which the heavy and light chains are encoded by nucleotide sequences derived from one or more human DNA sources. A fully human antibody can also be constructed by gene or chromosome transfection methods and phage display technology, or constructed by B cells activated in vitro, all of which are known in the art.

The terms "full-length antibody", "intact antibody", "complete antibody" and "whole antibody" are used interchangeably herein and refer to an antibody in a substantially intact form, as distinguished from the antigen-binding fragments defined below. These terms specifically refer to an antibody whose light chain and heavy chain comprises constant region. The "antibody" of the present disclosure includes "full-length antibody" and antigen-binding fragments thereof.

In some embodiments, the full-length antibody of the present disclosure includes antibodies formed by linking the light chain variable region to the light chain constant region, and linking the heavy chain variable region to the heavy chain constant region, as shown in the light and heavy chain combination in the table 1 to 4 below. Those skilled in the art can select different antibody-derived light chain constant regions and heavy chain constant regions according to actual needs, for example, human antibody-derived light chain constant regions and heavy chain constant regions.

The term "antigen-binding fragment" or "functional fragment" of an antibody refers to one or more fragments of the antibody that retain the ability to specifically bind to an antigen (for example, TSLP). It has been shown that fragments of full-length antibodies can be used to perform the antigen-binding function of antibodies. Examples of the binding fragment included in the term "antigen-binding fragment" of an antibody include (i) Fab fragment, a monovalent fragment consisting of VL, VH, CL and CH1 domains; (ii) F(ab')₂ fragment, a bivalent fragment comprising two Fab fragments linked by a disulfide bridge in the hinge region; (iii) Fd fragment, consisting of VH and CH1 domains; (iv) Fv fragment, consisting of VH and VL domains of one arm of the antibody; (V) dsFv, a stable antigen-binding fragment formed by interchain disulfide bonds between VH and VL; (vi) diabody, bispecific antibody and multispecific antibody, comprising fragments like scFv, dsFv, Fab, etc. In addition, although the two domains VL and VH of the Fv fragment are encoded by separate genes, recombination methods can be used to link them by synthetic linkers so that it can be produced as a single protein chain in which the VL and VH regions pair to form a monovalent molecule (referred to as single-chain Fv (scFv); see, for example, Bird et al. (1988) Science 242:423-426; and Huston et al. (1988) Proc. Natl. Acad. Sci USA 85: 5879-5883). Such single chain antibodies are also included in the term "antigen-binding fragment" of an antibody. Such antibody fragments are obtained by using conventional techniques known to those skilled in the art, and screened in the same manner as that used for intact antibodies. The antigen binding moiety can be produced by recombinant DNA technology or by enzymatic or chemical fragmentation of the intact immunoglobulin. The antibodies may be antibodies of different isotypes, for example, IgG (for example, IgG1, IgG2, IgG3 or IgG4 subtypes), IgA1, IgA2, IgD, IgE or IgM antibodies.

Fab is an antibody fragment that has a molecular weight of about 50,000 and has antigen-binding activity among fragments obtained by treating IgG antibody molecules with papain (which cleaves the amino acid residue at position 224 of the H chain), in which about half of the H chain of the N-terminal side and the entire L chain are joined together by disulfide bonds.

F(ab')2 is an antibody fragment that has a molecular weight of about 100,000 and has antigen-binding activity and comprises two Fab regions connected at the hinge position among fragments obtained by digesting the lower part of the two disulfide bonds in the hinge region of IgG with the enzyme pepsin.

Fab' is an antibody fragment that has a molecular weight of about 50,000 and has antigen-binding activity obtained by cleaving the disulfide bond in the hinge region of the F(ab')2. The Fab' of the present disclosure can be produced by using reducing agents, for example dithiothreitol, to treat the F(ab')2 of the present disclosure which specifically recognizes TSLP and binds to the amino acid sequence of the extracellular domain or three-dimensional structure thereof.

In addition, the Fab' can be produced by inserting the DNA encoding the Fab' fragment of the antibody into a prokaryotic expression vector or a eukaryotic expression vector and introducing the vector into a prokaryotic organism or eukaryotic organism to express the Fab'.

The term "single-chain antibody", "single-chain Fv" or "scFv" refers to molecules comprising an antibody heavy chain variable domain (or region, VH) and an antibody light chain variable domain (or region, VL) connected by a linker. Such scFv molecules can have the general structure: NH₂-VL-linker-VH-COOH or NH₂-VH-linker-VL-COOH. Suitable prior art linkers consist of repeated GGGGS amino acid sequences or variants thereof, for example using 1 to 4 repeated variants (Holliger et al. (1993), Proc. Natl. Acad. Sci. USA 90: 6444-6448). Other linkers that can be used in the present disclosure are described in Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

Diabody is an antibody fragment in which scFv or Fab is dimerized, and is an antibody fragment with bivalent antigen-binding activity. In the bivalent antigen binding activity, the two antigens can be the same or different.

Bispecific antibody and multispecific antibody refer to an antibody that can simultaneously bind to two or more antigens or antigenic determinants, including scFv or Fab fragments that can bind to TSLP.

The diabody of the present disclosure can be produced by the following steps: obtaining the coding cDNA of VH and VL of the monoclonal antibody of the present disclosure which specifically recognizes human TSLP and binds to the amino acid sequence of the extracellular domain or three-dimensional structure thereof, constructing the DNA encoding scFv so that the amino acid sequence length of the peptide linker is 8 residues or less, inserting the DNA into a prokaryotic expression vector or a eukaryotic expression vector, and then introducing the expression vector into a prokaryote organism or eukaryotic organism to express the diabody.

dsFv is obtained by linking VH and VL polypeptides in which one amino acid residue in each is substituted with a cysteine residue via disulfide bonds between the cysteine residues. The amino acid residues substituted with cysteine residues can be selected according to known methods (Protein Engineering, 7, 697 (1994)) based on the three-dimensional structure prediction of the antibody.

The full-length antibody or antigen-binding fragment of the present disclosure can be produced by the following steps: obtaining the coding cDNA of VH and VL of the monoclonal antibody of the present disclosure which specifically recognizes human TSLP and binds to the amino acid sequence of the extracellular domain or three-dimensional structure thereof, constructing the DNA encoding the full-length antibody or antigen-binding fragment, inserting the DNA into a prokaryotic expression vector or a eukaryotic expression vector, and then introducing the expression vector into a prokaryotic organism or eukaryotic organism for expression.

The term "amino acid difference" or "amino acid mutation" refers to the presence of amino acid changes or mutations in the variant protein or polypeptide compared with the original protein or polypeptide, including occurrence of 1, 2, 3 or more amino acid insertion, deletion or substitution on the basis of the original protein or polypeptide.

The term "antibody framework" or "FR region" refers to a moiety of the variable domain VL or VH, which serves as a scaffold for the antigen binding loop (CDR) of the variable domain. Essentially, it is a variable domain without CDR.

The term "complementarity determining region", "CDR" or "hypervariable region" refers to one of the six hypervariable regions in the variable domain of an antibody that mainly contribute to antigen binding. Generally, there are three CDRs (HCDR1, HCDR2, HCDR3) in each heavy chain variable region, and three CDRs (LCDR1, LCDR2, LCDR3) in each light chain variable region. Any one of a variety of well-known schemes can be used to determine the amino acid sequence boundaries of the CDRs, including the "Kabat" numbering rules (see Kabat et al. (1991), "Sequences of Proteins of Immunological Interest", 5th edition, Public Health Service, National Institutes of Health, Bethesda, MD), "Chothia" numbering rules (see Al-Lazikani et al., (1997) JMB 273: 927-948) and ImmunoGenTics (IMGT) numbering rules (Lefranc M. P., Immunologist, 7, 132-136 (1999); Lefranc, M. P., et al., Dev. Comp. Immunol., 27, 55-77 (2003)), etc. For example, for the classical format, following the Kabat rule, the amino acid residue numbers of CDRs in the heavy chain variable domain (VH) are 31-35 (HCDR1), 50-65 (HCDR2) and 95-102 (HCDR3); the amino acid residue numbers of CDRs in the light chain variable domain (VL) are 24-34 (LCDR1), 50-56 (LCDR2) and 89-97 (LCDR3). Following the Chothia rule, the amino acid residue numbers of CDRs in VH are 26-32 (HCDR1), 52-56 (HCDR2) and 95-102 (HCDR3); and the amino acid residue numbers in VL are 26-32 (LCDR1), 50-52 (LCDR2) and 91-96 (LCDR3). By combining the CDR definitions of both Kabat and Chothia, the CDRs consist of amino acid residues 26-35 (HCDR1), 50-65 (HCDR2) and 95-102 (HCDR3) in human VH and amino acid residues 24-34 (LCDR1), 50-56 (LCDR2) and 89-97 (LCDR3) in human VL. Following IMGT rules, the amino acid residue numbers of CDRs in VH are roughly 26-35 (CDR1), 51-57 (CDR2) and 93-102 (CDR3), and the amino acid residue numbers of CDRss in VL are roughly 27-32 (CDR1), 50-52 (CDR2) and 89-97 (CDR3). Following IMGT rules, the CDR regions of an antibody can be determined by using the program IMGT/DomainGap Align.

The term "epitope" or "antigenic determinant" refers to a site on an antigen where an immunoglobulin or antibody specifically binds (for example, a specific site on TSLP molecules). Epitopes generally include at least 3, 4, 5, 6, 7, 8, 9, 10, 11, 12, 13, 14 or 15 consecutive or non-consecutive amino acids in a unique spatial conformation. See, for example, Epitope Mapping Protocols in Methods in Molecular Biology, Vol. 66, G. E. Morris, Ed. (1996).

The terms "specifically binds", "selectively binds", "binds selectively" and "binds specifically" refer to the binding of an antibody to an epitope on a predetermined antigen. Generally, an antibody binds with an affinity (KD) of about less than $10^{-8}$M, for example about less than $10^{-9}$M, $10^{-10}$M, $10^{-11}$ M, $10^{-12}$ M or less.

The term "KD" refers to the dissociation equilibrium constant of a specific antibody-antigen interaction. Generally, the antibody of the present disclosure binds to TSLP with an affinity (KD) of about less than $10^{-7}$M, for example about less than $10^{-8}$M or $10^{-9}$M, for example, in the present disclosure, the affinity of the antibody to the cell surface antigen is determined by the FACS or Biacore method to determine the KD value.

When the term "competition" is used in the context of antigen-binding proteins (for example neutralizing antigen-binding protein or neutralizing antibody) that compete for the same epitope, it refers to the competition between the antigen-binding proteins, which is determined by the following assay: in the assay, the antigen-binding proteins to be tested (for example antibodies or immunological functional fragments thereof) prevent or inhibit (for example reduce) the specific binding of a reference antigen-binding protein (for example a ligand or a reference antibody) to a common antigen (for example TSLP antigen or fragment thereof). Numerous types of competitive binding assays can be used to determine whether one antigen-binding protein competes with another, these assays are for example: solid phase direct or indirect radioimmunoassay (RIA), solid phase direct or indirect enzyme immunoassay (EIA), sandwich competition assay (see for example Stahli et al., 1983, Methods in Enzymology 9:242-253); solid phase directbiotin-avidin EIA (see for example Kirkland et al., 1986, J. Immunol. 137:3614-3619), solid phase direct labeling assay, solid phase direct labeling sandwich assay (see for example Harlow and Lane, 1988, Antibodies, A Laboratory Manual, Cold Spring Harbor Press); solid phase direct labeling RIA with I-125 labels (see for example Morel et al., 1988, Molec. Immunol. 25: 7-15); solid-phase direct biotin-avidin EIA (see for example Cheung, et al., 1990, Virology 176: 546-552); and directly labeling RIA (Moldenhauer et al., 1990, Scand. J. Immunol. 32:77-82). Generally, the assays involve using any one of unlabeled test antigen-binding protein and labeled reference antigen-binding protein to bind purified antigens bound to a solid surface or cells. Competitive inhibition is measured by measuring the amount of label bound to the solid surface or cells in the presence of the test antigen-binding protein. Generally, the test antigen-binding protein is present in excess. The antigen-binding proteins identified by competition assays (competitive antigen-binding proteins) include: antigen-binding proteins that bind to the same epitope as the reference antigen-binding protein; and antigen-binding proteins that binds to adjacent epitopes that are sufficiently close to the binding epitope of the reference antigen-binding protein, the two epitopes sterically hindering each other from binding. Generally, when the competitive antigen-binding protein is present in excess, it will inhibit (for example reduce) the specific binding of the reference antigen-binding protein to the common antigen by at least 40-45%, 45-50%, 50-55%, 55-60%, 60-65%, 65-70%, 70%-75% or 75% or more. In some cases, the binding is inhibited by at least 80-85%, 85-90%, 90-95%, 95-97%, or 97% or more.

The term "nucleic acid molecule" used herein refers to DNA molecule and RNA molecule. The nucleic acid molecule can be single-stranded or double-stranded, and is preferably double-stranded DNA or single-stranded mRNA or modified mRNA. When a nucleic acid is placed in a functional relationship with another nucleic acid sequence, the nucleic acid is "operably linked". For example, if a promoter or enhancer affects the transcription of a coding sequence, then the promoter or enhancer is operably linked to the coding sequence.

Amino acid sequence "identity" "identity" refers to the percentage of the amino acid residues that are identical between the first and the second sequence when the amino acid sequences are aligned (introducing gaps when necessary) to achieve the maximum percentage of sequence identity, and no conservative substitutions are considered as part of the sequence identity. For the purpose of determining the percentage of amino acid sequence identity, the alignment can be achieved by a variety of ways within the technical scope of the art, for example, using publicly available computer software, such as BLAST, BLAST-2, ALIGN, ALIGN-2 or Megalign (DNASTAR) software. Those skilled in the art can determine the parameters suitable for measuring the alignment, including any algorithm required to achieve the maximum alignment over the entire length of the sequences being compared.

The term "expression vector" refers to a nucleic acid molecule capable of transporting another nucleic acid to which it has been linked. In one embodiment, the vector is a "plasmid", which refers to a circular double-stranded DNA loop into which additional DNA segments can be linked. In another embodiment, the vector is a viral vector in which additional DNA segments can be linked into the viral genome. The vectors disclosed herein can replicate autonomously in the host cell into which they have been introduced (for example, bacterial vectors with bacterial origin of replication and episomal mammalian vectors) or can be integrated into the genome of the host cell after being introduced into the host cell, so as to replicate together with the host genome (for example, non-episomal mammalian vectors).

The methods for producing and purifying antibodies and antigen-binding fragments are well known in the prior art, such as Antibody Experiment Technical Guide, Cold Spring Harbor, Chapters 5-8 and 15. For example, mice can be immunized with human TSLP or fragment thereof, and the obtained antibodies can be renatured and purified, and amino acid sequencing can be performed by using conventional methods. Antigen-binding fragments can also be prepared by using conventional methods. The antibody or antigen-binding fragment according to the present disclosure is genetically engineered to add one or more human FR regions to the non-human CDR regions. The human FR germline sequences can be obtained from the ImmunoGeneTics (IMGT) website http://imgt.cines.fr by comparing the IMGT human antibody variable region germline gene database and MOE software, or be obtained from The Immunoglobulin FactsBook, 2001ISBN012441351.

The term "host cell" refers to a cell into which an expression vector has been introduced. Host cells can include bacteria, microorganisms, plant or animal cells. Bacteria that can be easily transformed include members of the enterobacteriaceae, for example *Escherichia coli* or *Salmonella* strains; Bacillaceae, for example *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese Hamster Ovary Cell Line), 293 cells and NS0 cells.

The engineered antibodies or antigen-binding fragments of the present disclosure can be prepared and purified by conventional methods. For example, the cDNA sequences encoding the heavy chain and light chain can be cloned and recombined into a GS expression vector. The recombinant immunoglobulin expression vectors can stably transfect CHO cells. As a more recommended prior art, mammalian expression systems can lead to glycosylation of antibodies, especially in the highly conserved N-terminal sites of the Fc region. Stable clones are obtained by expressing antibodies that specifically bind to human TSLP. Positive clones are expanded in serum-free medium of bioreactors to produce antibodies. The medium into which the antibodies are secreted can be purified by conventional techniques. For example, using A or G Sepharose FF column with adjusted buffer for purification. Non-specifically bound components are washed off. Then the bound antibodies are eluted by the pH gradient method, and the antibody fragments are detected by SDS-PAGE and collected. The antibodies can be filtered and concentrated by conventional methods. Soluble mixtures and polymers can also be removed by conventional methods, for example molecular sieves and ion exchange. The resulting product needs to be frozen immediately, such as at −70° C., or lyophilized.

"Administering", "giving" and "treating", when applied to animals, humans, experimental subjects, cells, tissues, organs or biological fluids, refer to the contact of the exogenous medicament, therapeutic agent, diagnostic agent or composition with the animals, humans, subjects, cells, tissues, organs or biological fluids. "Administering", "giving" and "treating" can refer to for example treatment, pharmacokinetics, diagnosis, research and experimental methods. Treating cells includes contacting reagents with cells, and contacting reagents with fluids, wherein the fluids are in contact with the cells. "Administering", "giving" and "treating" also refer to treating for example cells by reagents, diagnosis, binding compositions or by another cell in vitro and ex vivo. "Treating" when applied to human, veterinary or research subjects, refers to therapeutic treatment, preventive or prophylactic measures, research and diagnostic applications.

"Treatment" refers to giving an internal or external therapeutic agent, for example a composition comprising any one of the binding compounds of the present disclosure, to a patient with one or more disease symptoms on which the therapeutic agent is known to have therapeutic effect. Generally, the therapeutic agent is given at an amount effective to alleviate one or more disease symptoms in the patient or population treated to induce the regression of such symptoms or inhibit the development of such symptoms to any clinically measurable extent. The amount of therapeutic agent that is effective to alleviate any specific disease symptom (also referred to as a "therapeutically effective amount") can vary according to a variety of factors, for example the patient's disease state, age and body weight, and the ability of the drug to produce the desired therapeutic effect in the patient. Whether the disease symptoms have been alleviated can be evaluated by any clinical testing methods commonly used by doctors or other health care professionals to evaluate the severity or progression of the symptoms. Although the embodiments of the present disclosure (for example treatment methods or products) may not be effective in alleviating the target disease symptom(s) in every patient, as determined according to any statistical testing methods known in the art, such as Student t-test, chi-square test, Mann and Whitney's U test, Kruskal-Wallis test (H test), Jonckheere-Terpstra test and Wilcoxon test, they should reduce the target disease symptom(s) in a statistically significant number of patients.

"Conservative modification" or "conservative replacement or substitution" refers to substitutions of amino acids in a protein with other amino acids having similar characteristics (e.g. charge, side-chain size, hydrophobicity/hydrophilicity, backbone conformation and rigidity, etc.), so that changes can be frequently made without changing the biological activity of the protein. Those skilled in the art know that, generally speaking, a single amino acid substitution in a non-essential region of a polypeptide does not substantially change the biological activity (see for example Watson et al. (1987) Molecular Biology of the Gene, The Benjamin/Cummings Pub. Co., Page 224, (4th edition)). In addition, the substitution of amino acids with similar structure or function is unlikely to disrupt the biological activity. Exemplary conservative substitutions are stated in the table "Exemplary amino acid conservative substitutions" below.

TABLE 5

Exemplary amino acid conservative substitutions

| Original residue | Conservative substitution |
|---|---|
| Ala (A) | Gly; Ser |
| Arg (R) | Lys; His |
| Asn (N) | Gln; His; Asp |
| Asp (D) | Glu; Asn |
| Cys (C) | Ser; Ala; Val |
| Gln (Q) | Asn; Glu |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |

TABLE 5-continued

Exemplary amino acid conservative substitutions

| Original residue | Conservative substitution |
|---|---|
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Effective amount" or "effective dose" refers to the amount of a drug, compound or pharmaceutical composition necessary to obtain any one or more beneficial or desired therapeutic results. For preventive use, the beneficial or desired results include elimination or reduction of risk, reduction of severity or delay of the disease onset, including the biochemistry, histology and/or behavioral symptoms of the disease, complications thereof and intermediate pathological phenotypes that appear during the developmental process of the disease. For therapeutic applications, the beneficial or desired results include clinical results, such as reducing the incidence of various target antigen-related disorders of the present disclosure or improving one or more symptoms of the disorder, reducing the dose of other agents required to treat the disorder, enhancing the therapeutic effect of another agent, and/or delaying the progression disorders of the patient related to the target antigen of the present disclosure.

"Exogenous" refers to substances produced outside organisms, cells or human bodies according to circumstances. "Endogenous" refers to substances produced inside cells, organisms or human bodies according to circumstances.

"Homology" refers to the sequence similarity between two polynucleotide sequences or between two polypeptides. When the positions in the two sequences compared are occupied by the same base or amino acid monomer subunit, for example if each position of two DNA molecules is occupied by adenine, then the molecules are homologous at that position. The homology percentage between two sequences is a function of the number of matched or homologous positions shared by the two sequences divided by the number of positions compared×100. For example, in the optimal sequence alignment, if 6 out of 10 positions in the two sequences are matched or homologous, then the two sequences are 60% homologous; if 95 out of 100 positions in the two sequences are matched or homologous, then the two sequences are 95% homologous. Generally, when aligning two sequences, comparisons are made to give the maximum percentage homology. For example, the comparison can be performed by the BLAST algorithm, wherein the parameters of the algorithm are selected to give the maximum match between each sequence over the entire length of each reference sequence. The following references relate to the BLAST algorithm that is often used for sequence analysis: BLAST ALGORITHMS: Altschul, S. F. et al., (1990) J. Mol. Biol. 215:403-410; Gish, W. et al., (1993) Nature Genet. 3:266-272; Madden, T. L. et al., (1996) Meth. Enzymol. 266:131-141; Altschul, S. F. et al., (1997) Nucleic Acids Res. 25:3389-3402; Zhang, J. et al., (1997) Genome Res. 7:649-656. Other conventional BLAST algorithms, such as those provided by NCBI BLAST, are also well known to those skilled in the art.

The expressions "cell", "cell line" and "cell culture" as used herein can be used interchangeably, and all such names include the progeny. Therefore, the words "transformant" and "transformed cell" include primary test cells and cultures derived therefrom, regardless of the number of passages. It should also be understood that due to deliberate or unintentional mutations, all offspring cannot be exactly the same in terms of DNA content. Mutant progeny with the same function or biological activity as screened in the original transformed cells is included. It is clearly visible from the context when a different name is referred to.

"Polymerase chain reaction" or "PCR" as used herein refers to a procedure or technique in which a trace amount of a specific moiety of nucleic acid, RNA and/or DNA is amplified as described in, for example, U.S. Pat. No. 4,683,195. Generally speaking, it is necessary to obtain sequence information from the end or outside of the target region, so that oligonucleotide primers can be designed; these primers are the same or similar in terms of sequence to the corresponding strand of the template to be amplified. The 5' terminal nucleotides of the two primers can be identical to the ends of the material to be amplified. PCR can be used to amplify specific RNA sequences, specific DNA sequences from total genomic DNA and cDNA sequences transcribed from total cellular RNA, phage or plasmid sequences, etc. Generally, see Mullis et al. (1987) Cold Spring Harbor, Symp. Ouant. Biol. 51:263; Erlich ed., (1989) PCR TECHNOLOGY (Stockton Press, N.Y.). The PCR used herein is regarded as an example, but not the only example, of a nucleic acid polymerase reaction method for amplifying a nucleic acid test sample, and the method includes using known nucleic acids as primers and nucleic acid polymerases to amplify or produce a specific moiety of the nucleic acid.

"Isolated" refers to a purified state, and in this case means that the designated molecule is substantially free of other biomolecules, for example nucleic acids, proteins, lipids, carbohydrates or other materials, for example cell debris and growth medium. Generally, the term "isolated" is not intended to mean the complete absence of these materials or the absence of water, buffer or salt, unless they are present in an amount that significantly interferes with the experimental or therapeutic use of the compound as described herein.

"Optional" or "optionally" means that the event or environment described later can occur, but does not have to occur, and this description includes occasions where the event or environment occurs or does not occur.

"Pharmaceutical composition" means a mixture containing one or more of the compounds described herein or physiologically/pharmaceutically acceptable salts or prodrugs thereof, and other chemical components, for example physiological/pharmaceutically acceptable carriers and excipients. The purpose of the pharmaceutical composition is to promote the administration to organisms, which facilitates the absorption of the active ingredient and thereby exerts biological activity.

The term "pharmaceutically acceptable carrier" refers to any inactive substance suitable for use in a formulation for the delivery of antibodies or antigen-binding fragments. The carrier can be an anti-adhesive agent, binder, coating, disintegrant, filler or diluent, preservative (such as antioxidant, antibacterial or antifungal agent), sweetener, absorption delaying agent, wetting agent, emulsifier, buffer, etc. Examples of suitable pharmaceutically acceptable carriers include water, ethanol, polyol (for example glycerol, propanediol, polyethylene glycol, etc.), dextrose, vegetable oil (for example olive oil), saline, buffer, buffered saline, and isotonic agent for example sugar, polyol, sorbitol and sodium chloride.

In addition, the present disclosure includes agents for treating TSLP-related diseases, comprising the anti-TSLP antibody of the present disclosure or antigen-binding fragment thereof as an active ingredient.

There is no limitation for the TSLP-related disease in the present disclosure, as long as it is a disease related to TSLP. For example, the therapeutic response induced by the molecule of the present disclosure can be achieved by binding to human TSLP, and then blocking the binding of TSLP to its receptors, or killing cells overexpressing TSLP.

In addition, the present disclosure relates to methods for immunodetection or determination of the target antigen (for example TSLP), reagents for immunodetection or determination of the target antigen (for example TSLP), methods for immunodetection or determination of cells expressing the target antigen (for example TSLP) and diagnostic agents for diagnosing diseases related to target antigen (for example TSLP) positive cells, which includes the antibody or antibody fragment of the present disclosure as active ingredient, which specifically recognizes the target antigen (for example human TSLP) and binds with the amino acid sequence of the extracellular domain or three-dimensional structure thereof.

In the present disclosure, the method used for detection or measurement of the amount of the target antigen (for example TSLP) may be any known method. For example, it includes immunodetection or measurement methods.

The immunodetection or measurement methods are methods of detecting or measuring the amount of antibody or antigen using labeled antigens or antibodies. Examples of immunodetection or measurement methods include radio-immunoassay (RIA), enzyme immunoassay (EIA or ELISA), fluorescence immunoassay (FIA), luminescence immunoassay, western blotting, physicochemical methods, etc.

The aforementioned TSLP-related diseases can be diagnosed by detecting or measuring cells expressing TSLP by using the antibody or antibody fragment of the present disclosure.

In order to detect cells expressing the polypeptide, known immunodetection methods can be used, preferably using immunoprecipitation, fluorescent cell staining, immunohistochemical staining, etc. In addition, fluorescent antibody staining method utilizing the FMAT8100HTS system (Applied Biosystem) can be used.

In the present disclosure, there is no particular limitation for the in vivo sample used for detection or measurement of the target antigen (for example TSLP), as long as it has the possibility of comprising cells expressing the target antigen (for example TSLP), for example histocyte, blood, plasma, serum, pancreatic juice, urine, feces, tissue fluid or culture fluid.

According to the required diagnostic method, the diagnostic agent containing the monoclonal antibody or antibody fragment thereof of the present disclosure can also contain reagents for performing antigen-antibody reaction or reagents for detecting the reaction. The reagents used for performing the antigen-antibody reaction include buffers, salts, etc. The reagents used for detection include reagents commonly used in immunodetection or measurement methods, for example labeled second antibodies that recognize the monoclonal antibody, antibody fragment thereof or conjugate thereof, and substrates corresponding to the label, etc.

In the above specification, presented are the details of one or more embodiments of the present disclosure. Although any methods and materials similar or identical to those described herein can be used to implement or test the present invention, the preferred methods and materials are described below. The other features, purposes and advantages of the present disclosure will be obvious through the specification and the claims. In the specification and the claims, unless otherwise clearly indicated in the context, the singular form includes the cases of plural referent. Unless otherwise defined, all technical and scientific terms used herein have the general meanings understood by those of ordinary skill in the art to which the present invention belongs. All patents and publications cited in the specification are incorporated by reference. The following examples are presented to more comprehensively illustrate the preferred embodiments of the present invention. These examples should not be construed as limiting the scope of the present invention in any way, and the scope of the present invention is defined by the claims.

EXAMPLES

The examples below are incorporated for further description of the present disclosure, but these examples do not limit the scope of the present disclosure.

The experimental methods with unspecified conditions in the examples or test examples of the present disclosure generally follow conventional conditions, or according to the conditions recommended by the raw material or commodity manufacturer. See Sambrook et al., Molecular Cloning: A Laboratory Manual, Cold Spring Harbor; Current Protocols Molecular Biology, Ausubel et al., Greene Publishing Associates, Wiley Interscience, NY. The reagents with unspecified sources are conventional reagents purchased on the market.

Example 1. Expression of TSLP and TSLP Receptor

The sequences encoding His-tagged human TSLP and cyno TSLP, human IgG1-Fc-tagged human TSLP and cyno TSLP, and TSLP receptor extracellular domain sequences were loaded onto phr vector to construct expression plasmids, which were then transfected into HEK293. The specific transfection steps were as follows: on the previous day, HEK293E cells were seeded in Freestyle expression medium (containing 1% FBS) at $0.8 \times 10^6$/ml, placed on a 37° C. constant temperature shaker (120 rpm) and continued culturing for 24 hours. After 24 hours, the transfection plasmid and the transfection reagent PEI were sterilized with 0.22 m filters. Then the transfection plasmid was adjusted to 100 μg/100 ml cells, and the mass ratio of PEI (1 mg/ml) and plasmid was 3:1. Taking the transfection of 200 ml HEK293E cells as an example, 10 ml of Opti-MEM and 200 kg plasmid were taken and mixed well, and let stand for 5 min; another 10 ml of Opti-MEM and 600 kg PEI were taken and mixed well, and let stand for 5 min. The plasmid and PEI were mixed well and let stand for 15 min, better not exceeding 20 min. The mixture of the plasmid and PEI was slowly added to 200 ml HEK293E cells, and placed on a shaker at 8% $CO_2$, 120 rpm and 37° C. for culturing. On day 3 of transfection, the culture was supplemented with 10% volume of supplemented medium. Until day 6 of transfection, samples were taken and centrifuged at 4500 rpm for 10 min to collect the cell supernatant. The supernatant was filtered and purified to obtain the recombinant TSLP and TSLP receptor proteins through Example 2. The purified proteins could be used in the experiments of each example below. The relevant sequences are as follows.

1. Amino acid sequence of his-tagged human TSLP antigen (huTSLP-his)

SEQ ID NO: 1

<u>MFPFALLYVLSVSFRKIFILQLVGLVLT</u>YDFTNCDFEKIKAAYLSTISKDLITYMS

GTKSTEFNNTVSCSNRPHCLTEIQSLTFNPTAGCASLAKEMFAMKTKAALAIW

CPGYSETQINATQAMKKARKSKVTTNKCLEQVSQLQGLWRRFNRPLLKQQ*GS*

*SDYKDDDDKHHHHHH*
Note:
Underlined is the signal peptide sequence; the italicized part is the Flag-His6-tag.

2. Amino acid sequence of Fc-tagged human TSLP antigen (huTSLP-Fc)

SEQ ID NO: 2

<u>MFPFALLYVLSVSFRKIFILQLVGLVLT</u>YDFTNCDFEKIKAAYLSTISKDLITYMS

GTKSTEFNNTVSCSNRPHCLTEIQSLTFNPTAGCASLAKEMFAMKTKAALAIW

CPGYSETQINATQAMKKARKSKVTTNKCLEQVSQLQGLWRRFNRPLLKQQ*DI*

*EGRMDEPKSSDKTHTCPPCPAPELLGGPSVFLFPPKPKDTLMISRTPEVTCVVVDV*

*SHEDPEVKFNWYVDGVEVHNAKTKPREEQYNSTYRVVSVLTVLHQDWLNGKEYK*

*CKVSNKALPAPIEKTISKAKGQPREPQVYTLPPSRDELTKNQVSLTCLVKGFYPSDIA*

*VEWESNGQPENNYKTTPPVLDSDGSFFLYSKLTVDKSRWQQGNVFSCSVMHEALH*

*NHYTQKSLSLSPGK*
Note:
Underlined is the signal peptide sequence; the italicized part is the linker-human Fc-tag.

3. Amino acid sequence of his-tagged cyno TSLP antigen (cynoTSLP-his)

SEQ ID NO: 3

<u>METDTLLLWVLLLWVPGSTG</u>YDFTNCDFQKIEADYLRTISKDLITYMSGTKST

DFNNTVSCSNRPHCLTEIQSLTFNPTPRCASLAKEMFARKTKATLALWCPGYSE

TQINATQAMKKARKSKVTTNKCLEQVSQLLGLWRRFIRTLLKQQ*GSSDYKDD*

*DDKHHHHHH*
Note:
Underlined is the signal peptide sequence; the italicized part is the flag-His6-tag.

4. Amino acid sequence of Fc-tagged cyno TSLP antigen (cynoTSLP-Fc)

SEQ ID NO: 4

<u>METDTLLLWVLLLWVPGSTG</u>YDFTNCDFQKIEADYLRTISKDLITYMSGTKST

DFNNTVSCSNRPHCLTEIQSLTFNPTPRCASLAKEMFARKTKATLALWCPGYSE

TQINATQAMKKARKSKVTTNKCLEQVSQLLGLWRRFIRTLLKQQ*DIEGRMDE*

*PKSSDKTHTCPPCPAPELLGGPSVFLFPPKPKDTLMISRTPEVTCVVVDVSHEDPE*

*VKFNWYVDGVEVHNAKTKPREEQYNSTYRVVSVLTVLHQDWLNGKEYKCKVSNK*

*ALPAPIEKTISKAKGQPREPQVYTLPPSRDELTKNQVSLTCLVKGFYPSDIAVEWES*

*NGQPENNYKTTPPVLDSDGSFFLYSKLTVDKSRWQQGNVFSCSVMHEALHNHYT*

*QKSLSLSPGK*
Note:
Underlined is the signal peptide sequence; the italicized part is the linker-human Fc-tag.

5. Amino acid sequence of Fc-tagged human TSLP receptor extracellular domain (human-TSLPR-Fc-ECD):

SEQ ID NO: 5

<u>GAAEGVQIQIIYFNLETVQVTWNASKYSRTNLTFHYRFNGDEAYDQCTNYLL</u>

<u>QEGHTSGCLLDAEQRDDILYFSIRNGTHPVFTASRWMVYYLKPSSPKHVRFSW</u>

<u>HQDAVTVTCSDLSYGDLLYEVQYRSPFDTEWQSKQENTCNVTIEGLDAEKCY</u>

<u>SFWVRVKAMEDVYGPDTYPSDWSEVTCWQRGEIRDACAETPTPPKPKLSK</u>*DI*

*EGRMDEPKSSDKTHTCPPCPAPELGGPSVFLFPPKPKDTLMISRTPEVTCVVVDV*

-continued
*SHEDPEVKFNWYVDGVEVHNAKTKPREEQYNSTYRWSVLTVLHQDWLNGKEYK*

*CKVSNKALPAPIEKTISKAKGQPREPQVYTLPPSRDELTKNQVSLTCLVKGFYPSDIA*

*VEWESNGQPENNYKTFPPVLDSDGSFFLYSKLTVDKSRWQQGNVFSCSVMHEALH*

NHYTQKSLSLSPGK
Note:
The underlined part is the human-TSLPR extracellular domain, and the italicized part is linker-human Fc-tag.

Example 2. Purification of TSLP and TSLP Receptor (TSLPR) Recombinant Proteins 2.1 Purification of His-Tagged TSLP Recombinant Proteins of Each Species The cell expression supernatant samples were centrifuged at high speed to remove impurities and filtered. Nickel columns were equilibrated with PBS solution and washed with 10 times of the column volume. The filtered supernatant samples were applied to the columns. The columns were washed with PBS solution containing 30 mM imidazole until the $A_{280}$ reading dropped to baseline. The target proteins were then eluted with PBS solution containing 300 mM imidazole, and the elution peaks were collected. The proteins were concentrated and exchanged into PBS, and aliquoted for use after being identified as correct by LC-MS. Obtained were his-tagged human TSLP and cyno TSLP.

2.1 Purification of Human Fc-Tagged TSLP of Each Species and Human TSLP Receptor Extracellular Domain Recombinant Proteins The cell expression supernatant samples were centrifuged at high speed to remove impurities. The recombinant antibody expression supernatant was purified by Protein A columns. The columns were washed with PBS until the A280 reading dropped to baseline. The target proteins were eluted with 100 mM acetate buffer pH 3.5, and neutralized with 1 M Tris-HCl pH 8.0. The obtained proteins were concentrated and exchanged into new solution, and aliquoted for use after being identified as correct by electrophoresis and LC-MS.

Example 3. Construction and Identification of Recombinant TSLP Receptor and IL7Rα Receptor Cell Lines In order to screen antibodies that can block TSLP from binding to TSLP receptor, CHO-K1 and BaF3 cell lines simultaneously expressing both human TSLP receptor and human IL7Rα (TSLPR/IL7Rα) were constructed. Lentivirus was used to package the target gene TSLPR/IL7 Rα and cloned into the target cell lines to form stable high-expressing cell lines. Firstly, human TSLPR and human IL7Rα genes were cloned into the plasmids pCDH-CMV-MCS-EF1-puro and pCDH-CMV-MCS-EF1-Neo (SBI, CD500B-1) respectively. Then the lentivirus infection method was used to insert human TSLPR into CHO-K1 and BaF3 cell lines, which were cultured under the selection pressure of 10 μg/ml puromycin (Gibco, US) for three weeks. Then, the second round of infection was carried out. The human IL7Rα gene was inserted into the cell lines and screened with 1 mg/ml G418 (Gibco, US) and 10 μg/ml puromycin for two to three weeks. Finally, CHO-K1 and BaF3 monoclonal cell lines with simultaneous high expression of TSLPR and IL7Rα were screened out by the flow sorting method.

Example 4. Preparation and Screening of Anti-Human TSLP Antibodies

Anti-human TSLP monoclonal antibodies were produced by immunizing laboratory SJL white mice, female, 6-8 weeks old (Beijing Charles River Laboratory Animal Technology Co., Ltd., animal production license number: SCXK (Beijing) 2012-0001). Housing environment: SPF level. After the mice were purchased, they were kept in a laboratory environment for 1 week, with 12/12 hours light/dark cycle adjustment, temperature 20-25° C.; humidity 40-60%. Mice that had adapted to the environment were immunized with recombinant proteins huTSLP-Fc (25 μg), huTSLP-his (12.5 μg) and cyno TSLP-his (12.5 μg) and TiterMax, Alum or CpG adjuvant. After 4-5 immunizations, mice with high antibody titers in the serum and the titers tending to reach a plateau were selected and sacrificed. The spleen cells were collected and fused with myeloma cells. Splenic lymphocytes and the myeloma cell Sp2/0 cells (ATCC® CRL-8287™) were fused to obtain hybridoma cells by using optimized PEG-mediated fusion steps.

For the initial screening, ELISA binding assays for human and cyno TSLP, assays of blocking human TSLP from binding to its receptor TSLPR, and experiments of inhibiting TSLP-induced proliferation of BaF3 cells were performed. After transferring the hybridoma cells to 24-well plates, the supernatant was re-screened. Hybridoma clones were obtained after two rounds of subcloning of the selected positive clones, and were used for antibody production and purification was performed by affinity methods.

The monoclonal hybridoma cell lines No. 3, No. 119, No. 179 and No. 199 with good activity were obtained after screening, and the hybridoma cells in logarithmic growth phase were collected. RNA was extracted with NucleoZol (MN), and reverse transcription was performed (PrimeScript™ Reverse Transcriptase, Takara, cat #2680A). The cDNA obtained by reverse transcription was amplified by PCR using mouse Ig-Primer Set (Novagen, TB326 Rev.B 0503) and sent to a sequencing company for sequencing. Murine anti-TSLP antibodies were obtained after sequencing: mab3, mab119, mab179 and mab199 sequences, the amino acid sequence of the variable regions thereof are as follows:

>mab3 murine heavy chain variable region sequence:
SEQ ID NO: 6
EVQLQQSGPVLVKPGASVKMSCKASGYTFT<u>DDYMNW</u>VKQSHGKSLEWIG<u>I</u>

<u>ISPYNGGTSYNQKFKG</u>KATLTVDKSSSTAYMELNSLTSEDSAVYYCAR<u>ED</u>

<u>YDYDGYAMDH</u>WGQGTSVTVSS

>mab3 murine light chain variable region sequence:
SEQ ID NO: 7
QIVLSQSPAILSASPGEKVTMTCRASSSVSYMHWYQQKPGSSPKPWIYATSNLASGVPARFSGSGSGTSYSLTISRVEAEDAATYYCQQWSSNRTFGGGTKLEIK >mab11 murine heavy chain variable region sequence:
SEQ ID NO: 8
QAYLQQSGAELVRPGASVKMSCKASGFAFTTYNMHWVKHTPGQGLEWIGAIYPGNGETSYNQKFKDRATLTVDKSSRTAYMQLSSLTSEDSAVYFCAREDDYGEGYFDVWGAGTTVTVSS >mab119 murine light chain variable region sequence:
SEQ ID NO: 9
DIVLTQSPASLAVSLGQRATISCRASESVDNSGLSFMHWYQQKPGQPPRLLLYRASNLGSGIPARFSGSGSGTDFTLTLNPVETDDVATYYCQQINTDPLTFGAGTKLELK >mab179 murine heavy chain variable region sequence:
SEQ ID NO: 10
QVQLQQSGAELVRPGTSVKVSCKASGYAFTNYLIEWVKQRPGQGLEWIGVIDPGNGDTNYNENFKGKATLTADKSSSTAYIELSRLTSEDSAVYFCAREDNTGTAFDYWGQGTTLTVSS >mab179 murine light chain variable region sequence:
SEQ ID NO: 11
SIVMTQTPKFLLVSAGDRVTISCKASQSVSSDVTWYQQKPGQSPKLLIYYVSNHYTGVPDRFTGSGYGTDFTFTISSVQAEDLAVYFCQQHHRFPLTFGAGTKLELK >mab199 murine heavy chain variable region sequence:
SEQ ID NO: 12
QVQLQQSGPQLVRPGASVKISCKASGYSFTTYWMHWVKQRPGQGLEWIGMIDPSDSETTLIQKFKDKATLTVDKSSSTAYMQLSSPTSEDSAVYYCARTLDGYYDYWGQGTTLTVSS >mab199 murine light chain variable region sequence:
SEQ ID NO: 13
DIQMTQSPASLSASVGETVTITCRASENIYSYLAWYQQKQGKSPQLLVYFAKTLAEGVPSRFSGSVSGTQFSLKINSLQPEDFGSYYCQHHYGTPWTFGGGTKLEIK The amino acid sequences of the CDR regions obtained according to the Kabat numbering rules are shown in the following table:

TABLE 6

Sequences of heavy chain and light chain CDR regions of antibodies from hybridoma clones

| Antibody | Heavy chain | | Light chain | |
|---|---|---|---|---|
| mab3 | HCDR1 | DDYMN SEQ ID NO: 14 | LCDR1 | RASSSVSYMH SEQ ID NO: 17 |
| | HCDR2 | IISPYNGGTSYNQKFKG SEQ ID NO: 15 | LCDR2 | ATSNLAS SEQ ID NO: 18 |
| | HCDR3 | EDYDYDGYAMDH SEQ ID NO: 16 | LCDR3 | QQWSSNRT SEQ ID NO: 19 |
| mab119 | HCDR1 | TYNMH SEQ ID NO: 20 | LCDR1 | RASESVDNSGLSFMH SEQ ID NO: 23 |
| | HCDR2 | AIYPGNGETSYNQKFKD SEQ ID NO: 21 | LCDR2 | RASNLGS SEQ ID NO: 24 |
| | HCDR3 | EDDYGEGYFDV SEQ ID NO: 22 | LCDR3 | QQINTDPLT SEQ ID NO: 25 |
| mab179 | HCDR1 | NYLIE SEQ ID NO: 26 | LCDR1 | KASQSVSSDVT SEQ ID NO: 29 |
| | HCDR2 | VIDPGNGDTNYNENFKG SEQ ID NO: 27 | LCDR2 | YVSNHYT SEQ ID NO: 30 |
| | HCDR3 | EDNTGTAFDY SEQ ID NO: 28 | LCDR3 | QQHHRFPLT SEQ ID NO: 31 |
| mab199 | HCDR1 | TYWMH SEQ ID NO: 32 | LCDR1 | RASENIYSYLA SEQ ID NO: 35 |
| | HCDR2 | MIDPSDSETTLIQKFKD SEQ ID NO: 33 | LCDR2 | FAKTLAE SEQ ID NO: 36 |
| | HCDR3 | TLDGYYDY SEQ ID NO: 34 | LCDR3 | QHHYGTPWT SEQ ID NO: 37 |

Chimeric antibodies were formed by linking the light and heavy chain variable regions of the aforementioned murine antibody with the light and heavy chain constant regions of the human antibody (such as the kappa constant region as shown in SEQ TD NO: 134 and the IgG1-YTE constant region as shown in SEQ ID NO: 133). The chimeric antibody corresponding to clone mab3 was named Ch3, and so forth for other antibodies.

Example 5. Design of Humanization of Anti-Human TSLP Monoclonal Antibodies

In order to reduce the immunogenicity of murine antibodies, the screened mab3, mab119, mab179 and mab199 antibodies with excellent in vivo and in vitro activities were humanized. Humanization of the murine monoclonal antibodies was performed according to the methods published in many documents in the art. Briefly, human antibody constant domains were used to replace parental (murine antibody) constant domains, human germline antibody sequences were selected according to the homology between the murine and human antibodies, and CDR grafting was performed. Then, based on the three-dimensional structure of the murine antibody, the amino acid residues of VL and VH were subjected to back-mutation, and the constant regions of the murine antibody were replaced with human constant regions, resulting in the final humanized molecule.

5.1 Selection and Back Mutations of the Human FR Regions for Mab3

(1) Selection and Back Mutations of the Human FR Regions

For mab3, the humanized VH template was IGHV1-3*01+IGHJ6*01, and the humanized VL template was IGKV3-20+IGKJ4*01. The CDRs of mab3 were grafted to the human template, and the variable region sequences obtained after grafting are as follows:

hu3 VL-CDR grafted:
SEQ ID NO: 38
EIVLTQSPATLSLSPGERATLSCRASSSVSYMHWYQQKPGQAPRLLIY

ATSNLASGIPARFSGSGSGTDFTLTISRLEPEDFAVYYCQQWSSNRTF

GGGTKVEIK hu3 VH-CDR grafted:
EVQLVQSGALVKKPGASVKVSCKASGYIIDDYMNWVRQAPGQRLEW

MGIISPYNGGTSYNQKFKGRVTITRDTSASTAYMELSSLRSEDTAVYY

CAREDYDYDGYAMDHWGQGTTVTVSS

Back mutation design of the mab3 humanized antibody is as shown in the following table:

TABLE 7

Back mutations of the mab3 humanized antibody

| hu3VL | | hu3VH | |
|---|---|---|---|
| hu3VL1 | Grafted | hu3VH1 | Grafted |
| hu3VL2 | L46P, F71Y | hu3VH2 | I69L, R71V, T73K |
| hu3VL3 | L46P, L47W, I58V, F71Y | hu3VH3 | R38K, M48I, V67A, I69L, R71V, T73K |
| hu3VL4 | L46P, L47W, I58V, D70S, F71Y | | |

Note:
Grafted represents grafting the murine antibody CDRs into the human germline FR region sequences. L46P represents that according to the Kabat numbering system, the L at position 46 is mutated back to P.

The sequences of the variable regions of the mab3 humanized antibody are as follows:

>hu3VL1 (hu3 VL-CDR grafted)
SEQ ID NO: 38
EIVLTQSPATLSLSPGERATLSCRASSSVSYMHWYQQKPGQAPRLLIYAT

SNLASGIPARFSGSGSGTDFTLTISRLEPEDFAVYYCQQWSSNRTFGGGT

KVEIK

>hu3VL2
SEQ ID NO: 39
EIVLTQSPATLSLSPGERATLSCRASSSVSYMHWYQQKPGQAPRPLIYAT

SNLASGIPARFSGSGSGTDYTLTISRLEPEDFAVYYCQQWSSNRTFGGGT

KVEIK

>hu3VL3
SEQ ID NO: 40
EIVLTQSPATLSLSPGERATLSCRASSSYSYMHWYQQKPGQAPRPWIYAT

SNLASGVPARFSGSGSGTDYTLTISRLEPEDFAVYYCQQWSSNRTFGGGT

KVEIK

>hu3VL4
SEQ ID NO: 41
EIVLTQSPATLSLSPGERATLSCRASSSYSYMHWYQQKPGQAPRPWIYAT

SNLASGVPARFSGSGSGTSYTLTISRLEPEDFAVYYCQQWSSNRTFGGGT

KVEIK

>h3VH1 (hu3 VH-CDR Grafted)
SEQ ID NO: 42
EVQLVQSGAEVKKPGASVKVSCKASGYTFTDDYMNWVRQAPGQRLEWMGI

ISPYNGGTSYNQKFKGRVTITRDTSASTAYMELSSLRSEDTAVYYCARED

YDYDGYAMDHWGQGTTVTVSS

>hu3VH2
SEQ ID NO: 43
EVQLVQSGAEVKKPGASVKVSCKASGYTFTDDYMNWVRQAPGQRLEWMGI

ISPYNGGTSYNQKFKGRVTLTVDKSASTAYMELSSLRSEDTAVYYCARED

YDYDGYAMDHWGQGTTVTVSS

>hu3VH3
SEQ ID NO: 44
EVQLVQSGAEVKKPGASVKVSCKASGYTFTDDYMNWVKQAPGQRLEWIGI

ISPYNGGTSYNQKFKGRATLTVDKSASTAYMELSSLRSEDTAVYYCARED

YDYDGYAMDHWGQGTTVTVSS

Note:
The single underline represents CDR regions, and the double underline represents back mutation sites.

The aforementioned light and heavy chain variable regions were combined with human germline light and heavy chain constant region sequences to form the final complete light and heavy chain sequences, thus obtaining the antibody with full-length sequence. Exemplarily, for the mab3 humanized antibody in the present disclosure, the heavy chain constant region is the IgG1-YTE constant region shown in SEQ ID NO: 133, and the light chain constant region is the kappa chain constant region shown in SEQ ID NO: 134, but they can also be replaced with other constant regions known in the art.

The sequences of the heavy and light chain variable regions of the obtained mab3 humanized antibodies are shown in the following table:

TABLE 8

Heavy and light chain variable region
sequences of mab3 humanized antibody

| Antibody | VH (SEQ ID No.) | VL (SEQ ID No.) |
|---|---|---|
| hu3-01 | 42 | 39 |
| hu3-02 | 42 | 40 |
| hu3-03 | 42 | 41 |
| hu3-04 | 43 | 38 |
| hu3-05 | 43 | 39 |
| hu3-06 | 43 | 40 |
| hu3-07 | 43 | 41 |
| hu3-08 | 44 | 39 |
| hu3-09 | 44 | 40 |
| hu3-10 | 44 | 41 |

The binding activity of mab3 humanized antibody to human TSLP was detected by ELISA method, and the results showed that mab3 humanized antibodies have very good binding ability to human TSLP.

(2) Point Mutation to Hu3 Antibody

It was found by detection that there were hot spots on the MDH sequence of HCDR3 and the NTR sequence of LCDR3 of the mab3 humanized antibody. Therefore, the corresponding hot spots were mutated. The sequences of the CDR regions of the mab3 humanized antibodies obtained after mutation are as follows:

TABLE 9

HCDR3 and LCDR3 sequences after mutation

| hu3 HCDR3-H110Y | EDYDYDGYAMDY SEQ ID NO: 45 |
|---|---|
| hu3 LCDR3-N93D | QQWSSDRT SEQ ID NO: 46 |

Note:
The positions of mutation sites in Table 9 are numbered according to the natural order of the variable region sequences.

It can be concluded that the CDR sequences of the mab3 humanized antibody are as follows:

TABLE 10

CDRs after mutation of mab3 humanized antibody

| Heavy chain | | Light chain | |
|---|---|---|---|
| HCDR1 | DDYMN SEQ ID NO: 14 | LCDR1 | RASSSVSYMH SEQ ID NO: 17 |
| HCDR2 | IISPYNGGTSYNQ KFKG SEQ ID NO: 15 | LCDR2 | ATSNLAS SEQ ID NO: 18 |
| HCDR3 (general formula) | EDYDYDGYAMDX1 SEQ ID NO: 47 | LCDR3 (general formula 1) | QQWSSX2RT SEQ ID NO: 48 |

Wherein, $X_1$ is selected from H or Y, $X_2$ is selected from N or D.

Exemplarily, the CDRs and heavy and light chain variable regions of the humanized antibody hu3-11 obtained after mutation are as follows:

TABLE 11

CDR regions of hu3-11

| Heavy chain | | Light chain | |
|---|---|---|---|
| HCDR1 | DDYMN SEQ ID NO: 14 | LCDR1 | RASSSVSYMH SEQ ID NO: 17 |
| HCDR2 | IISPYNGGTSYNQ KFKG SEQ ID NO: 15 | LCDR2 | ATSNLAS SEQ ID NO: 18 |
| HCDR3-H110Y | EDYDYDGYAMDY SEQ ID NO: 45 | LCDR3-N93D | QQWSSDRT SEQ ID NO: 46 |

>Light chain variable region of hu3-11
(hu3VL4-N93D)
SEQ ID NO: 49
EIVLTQSPATLSLSPGERATLSCRASSSVSYMHWYQQKPGQAPRPWIYAT

SNLASGVPARFSGSGSGTSYTLTISRLEPEDFAVYYCQQWSSDRTFGGGT

KVEIK

>Heavy chain variable region of hu3-11
(hu3VH2-H110Y)
SEQ ID NO: 50
EVQLVQSGAEVKKPGASVKVSCKASGYTFTDDYMNWVRQAPGQRLEWMGI

ISPYNGGTSYNQKFKGRVTLTVDKSASTAYMELSSLRSEDTAVYYCARED

YDYDGYAMDYWGQGTTVTSS

The light and heavy chain variable regions after hot spot mutation were recombined with human germline light and heavy chain constant region sequences to form complete light and heavy chain sequences, thus obtaining the antibody with full-length sequence.

The binding activity of the antibody obtained after mutation to human TSLP was detected by using ELISA method. The results showed that the affinity activity of hu3-11 to human TSLP is still high, indicating that the hot spot mutations on the HCDR3 and LCDR3 of the mab3 humanized antibody do not affect the activity of antibody.

(3) Affinity Maturation of Hu3-11 Antibody

The hu3-11 molecule was subjected to affinity maturation. The process of affinity maturation was as follows:

Construction of the yeast library: degenerate primers were designed, and the designed mutant amino acids were introduced into the antibody hu3-11 scFv mutant libraries by PCR method, with the size of each library of about 109. The constructed yeast libraries were verified for their diversity by sequencing method.

In the first round of screening, about $5 \times 10^{10}$ cells from the hu3-11-scFv mutant libraries and biotinylated TSLP-Fc protein (1-10 µg/ml) were incubated in 50 ml 0.1% bovine serum albumin (BSA)-containing phosphate buffered saline (PBSA) for 1 hour at room temperature. Then, the mixture was washed with 0.1% PBSA to remove unbound antibody fragments. Then, 100 µl of streptomycin beads (Milenyi Biotec, Auburn, CA) were added to the hu3-11-scFv antibody mutant libraries bound to the biotinylated TSLP-Fc, and were loaded on the AutoMACS system for sorting. The cells with high affinity to TSLP-Fc were collected from the antibody library and induced at 250 rpm and 20° C. for 18 h. The obtained enriched library was subjected to the second round of screening against biotinylated recombinant TSLP-Fc protein.

For the third and fourth rounds of screening, the library cells from the previous round were incubated with biotinylated recombinant TSLP-Fc protein (0.1-1 μg/ml) and 10 μg/ml Mouse Anti-cMyc (9E10, sigma) antibody in 0.1% PBSA at room temperature for 1 h. The mixture was washed with 0.1% PBSA to remove unbound antibody fragments. Goat anti-mouse-Alexa488 (A-11001, life technologies) and Streptavidin-PE (S-866, Life technologies) were added and incubated at 4° C. for 1 h. The mixture was washed with 0.1% PBSA to remove unbound antibody fragments. Finally, antibodies with high affinity were screened out by FACS screening (BD FACSAria™ FUSION).

The hu3-11-scFv mutant libraries underwent 2 rounds of MACS screening and 2 rounds of FACS screening by utilizing biotinylated TSLP-Fc antigen. About 400 yeast single clones were then selected for culturing and inducing expression. The binding of yeast single clones to TSLP-Fc antigen was detected by using FACS, and yeast single clones with high affinity were selected and subjected to sequencing verification. The sequenced clones were compared and analyzed. After removing redundant sequences, the non-redundant sequences were converted into full-length antibodies for mammalian cell expression.

The sequences of the light chain variable regions obtained by affinity maturation are as follows:

```
>hu3VL5
                                            SEQ ID NO: 51
EIVLTQSPATLSLSPGERATLSCRASSSVSYMHWYQQKPGQAPRPWIYAT

SNLASGVPARFSGSGSGTSYTLTISRLEPEDFAVYYCQQSDNVRGFGGGT

KVEIK

>hu3VL6
                                            SEQ ID NO: 52
EIVLTQSPATLSLSPGERATLSCRASSSVSYMHWYQQKPGQAPRPWIYAT

SNLASGVPARFSGSGSGTSYTLTISRLEPEDFAVYYCQQSDSGREFGGGT

KVEIK
```

The obtained light chain variable regions were recombined with the heavy chain variable regions of the mab3 humanized antibody to obtain a new mab3 humanized antibody. Exemplarily, huVL5 and huVL6 were respectively combined with hu3VH2-H110Y to obtain the new antibody molecules hu3-12 and hu3-13, which in details are as shown as follows:

TABLE 12

Antibodies obtained by affinity maturation

| Antibody | hu3VH | hu3VL |
|---|---|---|
| hu3-12 | hu3VH2-H110Y | hu3VL5 |
| hu3-13 | hu3VH2-H110Y | hu3VL6 |

The CDR sequences of the mab humanized antibody obtained after affinity maturation are shown as follows:

TABLE 13

Antibody CDRs of mab3 humanized antibody obtained by affinity maturation

| Antibody | Heavy chain | | Light chain | |
|---|---|---|---|---|
| hu3-12 | HCDR1 | DDYMN SEQ ID NO: 14 | LCDR1 | RASSSVSYMH SEQ ID NO: 17 |

TABLE 13-continued

Antibody CDRs of mab3 humanized antibody obtained by affinity maturation

| Antibody | Heavy chain | | Light chain | |
|---|---|---|---|---|
| | HCDR2 | IISPYNGGTSYNQ KFKG SEQ ID NO: 15 | LCDR2 | ATSNLAS SEQ ID NO: 18 |
| | HCDR3-H110Y | EDYDYDGYAMDY SEQ ID NO: 45 | LCDR3-V1 | QQSDNVRG SEQ ID NO: 53 |
| hu3-13 | HCDR1 | DDYMN SEQ ID NO: 14 | LCDR1 | RASSSVSYMH SEQ ID NO: 17 |
| | HCDR2 | IISPYNGGTSYNQ KFKG SEQ ID NO: 15 | LCDR2 | ATSNLAS SEQ ID NO: 18 |
| | HCDR3-H110Y | EDYDYDGYAMDY SEQ ID NO: 45 | LCDR3-V2 | QQSDSGRE SEQ ID NO: 54 |

The obtained new antibody mab3 humanized antibody was subjected to ELISA to detect its binding activity to human TSLP. The results showed that hu3-12 and hu3-13 still have high binding ability to human TSLP. It showed that changes of LCDR3 would not affect the activity of the hu3 series of antibodies.

In summary, the CDRs of the mab3 humanized antibody have the sequences shown as follows:

TABLE 14

General formula sequences of CDR regions of mab3 humanized antibody

| Heavy chain | | Light chain | |
|---|---|---|---|
| HCDR1 | DDYMN SEQ ID NO: 14 | LCDR1 | RASSSVSYMH SEQ ID NO: 17 |
| HCDR2 | IISPYNGGTSYNQ KFKG SEQ ID NO: 15 | LCDR2 | ATSNLAS SEQ ID NO: 18 |
| HCDR3 (general formula) | EDYDYDGYAMDX$_1$ SEQ ID NO: 47 | LCDR3 (general formula 2) | QQSDX$_3$X$_4$RX$_5$ SEQ ID NO: 55 |

Wherein, $X_1$ is H or Y, $X_3$ is N or S, $X_4$ is V or G, $X_5$ is G or E.

The combinations of the antibody heavy and light chain variable regions of the mab3 humanized antibody after hot spot mutation and affinity maturation are shown in the following table:

TABLE 15

Sequences of antibodies after affinity maturation

| Antibody | VH (SEQ ID NO) | VL (SEQ ID NO) |
|---|---|---|
| hu3-11 | 50 | 49 |
| hu3-12 | 50 | 51 |
| hu3-13 | 50 | 52 |

5.2 Selection and back mutations of the human FR regions for mab119

For mab119, IGHV1-69*02 and HJ6*01 were selected as templates for the VH, and IGKV4-1*01 and IGKJ2*01 as well as IGKV3-11*01 and IGKJ2*01 were selected as templates for the VL. The CDR regions of the murine antibody were grafted to the selected humanized templates, and the FR regions were subjected to back mutation to obtain different light chain and heavy chain variable regions. The variable region sequences obtained by CDR grafting are as follows:

\>hu119-VL CDR (Grafted, IGKV4-1*01)
SEQ ID NO: 56
DIVMTQSPDSLAVSLGERATINCRASESVDNSGLSFMHWYQQKPGQPPKL

LIYRASNLGSGVPDRFSGSGSGTDFTLTISSLQAEDVAVYYCQQINTDPL

TFGQGTKLEIK

\>hu119VL4 (Grafted, IGKV3-11*01)
SEQ ID NO: 59
EIVLTQSPATLSLSPGERATLSCRASESVDNSGLSFMHWYQQKPGQAPRL

LIYRASNLGSGIPARFSGSGSGTDFTLTISSLEPEDFAVYYCQQINTDPL

TFGQGTKLEIK

\>hu119-VH CDR (Grafted, IGHV1-69*02)
SEQ ID NO: 62
EVQLVQSGAEVKKPGSSVKVSCKASGGTFSTYNMHWVRQAPGQGLEWMGA

IYPGNGETSYNQKFKDRVTITADKSTSTAYMELSSLRSEDTAVYYCARED

DYGEGYFDVWGQGTTVTVSS

Back mutations of the mab119 humanized antibody are as shown in the following table:

TABLE 16

Back mutations of mab119

| hu119VL | | | hu119VH | |
|---|---|---|---|---|
| hu119VL1 | Grafted (IGKV4-1*01) | | hu119VH1 | Grafted (IGHV1-69*02) |
| hu119VL2 | Grafted (IGKV4-1*01) + M4L | | hu119VH2 | G27F, I69L, A71V |
| hu119VL3 | Grafted (IGKV4-1*01) + I48L, V58I | | hu119VH3 | G27F, M48I, V67A, I69L, A71V |
| hu119VL4 | Grafted (IGKV3-11*01) | | hu119VH4 | G27F, R38K, Q39H, M48I, V67A, I69L, A71V |
| hu119VL5 | Grafted (IGKV3-11*01) + A43P, I48L | | hu119VH5 | M48I, V67A, I69L, A71V |
| hu119VL6 | Grafted (IGKV3-11*01) + E1D, A43P, I48L | | hu119VH6 | V2A, G27F, M48I, V67A, I69L, A71V |
| | | | hu119VH7 | M48I, V67A, I69L, A71V, S76R |
| | | | hu119VH8 | V2A, G27F, M48I, V67A, I69L, A71V, S76R |

Note:
For example, M4L represents that according to the Kabat numbering system, M at position 4 is mutated back to L. Grafted represents that the murine antibody CDR is implanted into the human germline FR region sequence.

The specific sequences of the variable regions of the mab119 humanized antibody are as follows:

\>hu119VL1 (Grafted (IGKV4-1*01))
SEQ ID NO: 56
DIVMTQSPDSLAVSLGERATINCRASESVDNSGLSFMHWYQQKPGQPPKL

LIYRASNLGSGVPDRFSGSGSGTDFTLTISSLQAEDVAVYYCQQINTDPL

TFGQGTKLEIK

\>hu119VL2
SEQ ID NO: 57
DIVLTQSPDSLAVSLGERATINCRASESVDNSGLSFMHWYQQKPGQPPKL

LIYRASNLGSGVPDRFSGSGSGTDFTLTISSLQAEDVAVYYCQQINTDPL

TFGQGTKLEIK

\>hu119VL3
SEQ ID NO: 58
DIVMTQSPDSLAVSLGERATINCRASESVDNSGLSFMHWYQQKPGQPPKL

LLYRASNLGSGIPDRFSGSGSGTDFTLTISSLQAEDVAVYYCQQINTDPL

TFGQGTKLEIK

\>hu119VL4 (Grafted, IGKV3-11*01)
SEQ ID NO: 59
EIVLTQSPATLSLSPGERATLSCRASESVDNSGLSFMHWYQQKPGQAPRL

LIYRASNLGSGIPARTSGSGSGTDFTLTISSLEPEDFAVYYCQQINTDPL

TFGQGTKLEIK

\>hu119VL5
SEQ ID NO: 60
EIVLTQSPATLSLSPGERATLSCRASESVDNSGLSFMHWYQQKPGQPPRL

LLYRASNLGSGIPARFSGSGSGTDFTLTISSLEPEDFAVYYCQQINTDPL

TFGQGTKLEIK

\>hu119VL6
SEQ ID NO: 61
DIVLTQSPATLSLSPGERATLSCRASESVDNSGLSFMHWYQQKPGQPPRL

LLYRASNLGSGIPARTSGSGSGTDFTLTISSLEPEDFAVYYCQQINTDPL

TFGQGTKLEIK

\>hu119VH1 (Grafted)
SEQ ID NO: 62
EVQLVQSGAEVKKPGSSVKVSCKASGGTFSTYNMHWVRQAPGQGLEWMGA

IYPGNGETSYNQKFKDRVTYTADKSTSTAYMELSSLRSEDTAVYYCARED

DYGEGYFDVWGQGTTVTVSS

\>hu119VH2
SEQ ID NO: 63
EVQLVQSGAEVKKPGSSVKVSCKASGFTFSTYNMHWVRQAPGQGLEWMGA

IYPGNGETSYNQKFKDRVTLTVDKSTSTAYMELSSLRSEDTAVYYCARED

DYGEGYFDVWGQGTTVTVSS

```
>hu119VH3
                            SEQ ID NO: 64
EVQLVQSGAEVKKPGSSVKVSCKASGFTFSTYNMHWVKHAPGQGLEWIGA
IYPGNGETSYNQKFKDRATLTVDKSTSTAYMELSSLRSEDTAVYYCARED
DYGEGYFDVWGQGTTVTVSS

>hu119VH4
                            SEQ ID NO: 65
EVQLVQSGAEVKKPGSSVKVSCKASGFTFSTYNMHWVKHAPGQGLEWIGA
IYPGNGETSYNQKFKDRATLTVDKSTSTAYMELSSLRSEDTAVYYCARED
DYGEGYFDVWGQGTTVTVSS

>hu119VH5
                            SEQ ID NO: 66
EVQLVQSQAEVKKPGSSVKVSCKASGGTFSTYNMHWVRQAPGQGLEWIGA
IYPGNGETSYNQKFKDRATLTVDKSTSTAYMELSSLRSEDTAVYYCARED
DYGEGYFDVWGQGTTVTVSS

>hu119VH6
                            SEQ ID NO: 67
EAQLVQSGAEVKKPGSSVKVSCKASGFTFSTYNMHWVRQAPGQGLEWIGA
IYPGNGETSYNQKFKDRATLTVDKSTSTAYMELSSLRSEDTAVYYCARED
DYGEGYFDVWGQGTTVTVSS

>hu119VH7
                            SEQ ID NO: 68
EVQLVQSGAEVKKPGSSVKVSCKASGGTFSTYNMHWVRQAPGQGLEWIGA
IYPGNGETSYNQKFKDRATLTVDKSTRTAYMELSSLRSEDTAVYYCARED
DYGEGYFDVWGQGTTVTVSS

>hu119VH8
                            SEQ ID NO: 69
EAQLVQSGAEVKKPGSSVKVSCKASGFTFSTYNMHWVRQAPGQGLEWIGA
IYPGNGETSYNQKFKDRATLTVDKSTRTAYMELSSLRSEDTAVYYCARED
DYGEGYFDVWGQGTTVTVSS
Note:
The single underline represents variable regions,
and the double underline represents back
mutations.
```

The aforementioned light and heavy chain variable regions were combined with human germline light and heavy chain constant region sequences to form the final complete light and heavy chain sequences, thus obtaining the antibody with full-length sequence. Exemplarily, for the mab119 humanized antibody in the present disclosure, the heavy chain constant region is the IgG1-YTE constant region shown in SEQ ID NO: 133, and the light chain constant region is the kappa chain constant region shown in SEQ ID NO: 134, but they can also be replaced with other constant regions known in the art.

The heavy and light chain variable regions of the mab119 humanized antibody are shown in Table 17.

TABLE 17

Heavy and light chain variable regions of the mab119 humanized antibody

| Antibody | VH (SEQ ID NO) | VL (SEQ ID NO) |
|---|---|---|
| hu119-01 | 62 | 56 |
| hu119-02 | 63 | 56 |
| hu119-03 | 64 | 56 |
| hu119-04 | 65 | 56 |
| hu119-05 | 62 | 57 |
| hu119-06 | 63 | 57 |
| hu119-07 | 64 | 57 |
| hu119-08 | 65 | 57 |
| hu119-09 | 62 | 58 |
| hu119-10 | 63 | 58 |
| hu119-11 | 64 | 58 |
| hu119-12 | 65 | 58 |
| hu119-13 | 64 | 59 |
| hu119-14 | 66 | 59 |
| hu119-15 | 67 | 59 |
| hu119-16 | 68 | 59 |
| hu119-17 | 69 | 59 |
| hu119-18 | 64 | 60 |
| hu119-19 | 66 | 60 |
| hu119-20 | 67 | 60 |
| hu119-21 | 68 | 60 |
| hu119-22 | 69 | 60 |
| hu119-23 | 64 | 61 |
| hu119-24 | 66 | 61 |
| hu119-25 | 67 | 61 |
| hu119-26 | 68 | 61 |
| hu119-27 | 69 | 61 |

The binding activity of the humanized antibody to human TSLP was detected by ELISA method, and the results showed that mab119 humanized antibodies can specifically bind to human TSLP.

(2) Mutations of hu119

It was found by detection that a hot spot was present in the LCDR1 DNS sequence of the mab119 humanized antibody, thus, the corresponding site was mutated to N31S or N31Q. The LCDR1 sequences obtained after mutation are as follows:

TABLE 18

LCDR1 after site mutation of mab119 humanized antibody

| hu119 LCDR1-N31S | RASESVDSSGLSFMH SEQ ID NO: 70 |
|---|---|
| hu119 LCDR1-N31Q | RASESVDQSGLSFMH SEQ ID NO: 71 |

Note:
The positions of mutation sites in Table 19 are numbered according to the natural order.

Exemplarily, the hu119VL2, hu119VL6 mutant sequences obtained after mutation are as follows:

```
>hu119VL2-N31S
                            SEQ ID NO: 72
DIVLTQSPDSLAVSLGERATINCRASESVDSSGLSFMHWYQQKPGQPPKL
LIYRASNLGSGVPDRFSGSGSGTDFTLTISSLQAEDVAVYYCQQINTDPL
TFGQGTKLEIK

>hu119VL2-N31Q
                            SEQ ID NO: 73
DIVLTQSPDSLAVSLGERATINCRASESVDQSGLSFMHWYQQKPGQPPKL
LIYRASNLGSGVPDRFSGSGSGTDFTLTISSLQAEDVAVYYCQQINTDPL
TGQGTKLEIK
```

```
>hu119VL6-N31S
                                       SEQ ID NO: 74
DIVLTQSPATLSLSPGERATLSCRASESVDSSGLSFMHWYQQKPGQPPRL

LLYRASNLGSGIPARFSGSGSGTDFTLTISSLEPEDFAVYYCQQINTDPL

TFGQGTKLEIK

>hu119VL6-N31Q
                                       SEQ ID NO: 75
DIVLTQSPATLSLSPGERATLSCRASESVDQSGLSFMHWYQQKPGQPPRL

LLYRASNLGSGIPARFSGSGSGTDFTLTISSLEPEDFAVYYCQQINTDPL

TFGQGTKLEIK
Note:
The single underline represents variable regions,
and the double underline represents back
mutations.
```

The obtained hu119VL2, hu119VL6 mutants were combined with hu119VH to obtain new humanized hu119 antibodies. Exemplarily, hu119VL2-N31S, hu119VL2-N31Q were respectively combined with hu119VH3 to obtain antibodies hu119-28 and hu119-29; hu119VL3-N31S was combined with hu119VH8 to obtain the antibody hu119-30. Exemplary combinations of variable regions of the mutated antibodies are as follows:

TABLE 19

Combinations of the humanized antibody variable regions after hot spot mutation

| | hu119VH | hu119VL |
|---|---|---|
| hu119-28 | hu119VH3 | hu119VL2-N31S |
| hu119-29 | hu119VH3 | hu119VL2-N31Q |
| hu119-30 | hu119VH8 | hu119VL6-N31S |

The affinity of the antibody obtained after mutation with human TSLP was detected by using ELISA method. The results showed that hu119-28 and hu119-29 antibodies still have relatively high affinity with human TSLP, showing that the N31S and N31Q mutations of LCDR2 will not affect the anti-TSLP antibody activity.

In summary, the CDRs of the mab119 humanized antibody have the sequences shown as follows:

TABLE 20

CDRs of mab119 humanized antibody

| HCDR1 | TYNMH SEQ ID NO: 20 | LCDR1-general formula | RASESVDX$_6$SGLSFMH SEQ ID NO: 76 |
|---|---|---|---|
| HCDR2 | AIYPGNGETSYNQKFKD SEQ ID NO: 21 | LCDR2 | RASNLGS SEQ ID NO: 24 |
| HCDR3 | EDDYGEGYFDV SEQ ID NO: 22 | LCDR3 | QQINTDPLT SEQ ID NO: 25 |

Wherein, X$_6$ is selected from N, S and Q.

5.3. Humanization of Mab179
(1) Template Selection and Back Mutations for Humanization of Mab179 Murine Antibody For mab179, IGHV1-69*02 and IGHJ6*01 were selected as templates for the VH, and IGKV4-1*01 and IGKJ2*01 or IGKV2-29*02 and IGKJ2*01 were selected as templates for the VL. The CDR regions of the murine antibody were grafted to the selected humanized templates, and the FR regions were subjected to back mutation to obtain light chain and heavy chain variable regions with different sequences. The humanized variable region sequences and back mutations are as follows:

```
>hu179VL1 (Graft (IGKV4-1*01))
                                       SEQ ID NO: 77
DIVMTQSPDSLAVSLGERATINCKASQSVSSDVTWYQQKPGQPPKLLIYY

VSNHYTGVPDRFSGSGSGTDFTLTISSLQAEDVAVYYCQQHHRFPLTFGQ

GTKLEIK

>hu179VL5 (Grafted (IGKV2-29*02))
                                       SEQ ID NO: 81
DIVMTQTPLSLSVTPGQPASISCKASQSVSSDVTWYLQKPGQSPQLLIYY

VSNHYTGVPDRFSGSGSGTDFTLKISRVEAEDVGVYYCQQHHRFPLTFGQ

GTKLEIK

>hu179VH1 (Grafted)
                                       SEQ ID NO: 85
EVQLVQSGAEVKKPGSSVKASCKASGGTFSNYLIEWVRQAPGQGLEWMGV

IDPGNGPTNYNENFKGRVTITADKSTSTAYMELSSLRSEDTAVYYCARED

NTGTAFDYWGQGTTVTVSS
```

TABLE 21

Templates and back mutations for Humanization of mab179

| hu179VL1VL | | hu179VH | |
|---|---|---|---|
| hu179VL1 | Graft (IGKV4-1*01) | hu179VH1 | Graft (IGHV1-69*02) |
| hu179VL2 | Graft (IGKV4-1*01) P43S | hu179VH2 | G27Y, I69L |
| hu179VL3 | Graft (IGKV4-1*01) P43S, L73F | hu179VH3 | G27Y, M48I, V67A, I69L, M80I |
| hu179VL4 | Graft (IGKV4-1*01) D1S, P43S | hu179VH4 | G27Y, R38K, M48I, R66K, V67A, I69L, M80I, S82bR |
| hu179VL5 | Grafted(IGKV2-29*02) | hu179VH5 | G27Y, T28A, M48I, V67A, I69L |
| hu179VL6 | Graft (IGKV2-29*02), D1S | | |
| hu179VL7 | Graft (IGKV2-29*02) D1S, L73F | | |
| hu179VL8 | Graft (IGKV2-29*02) D1S, S67Y | | |

Note:
For example, P43S represents that according to the Kabat numbering system, P at position 43 is mutated back to S. Grafted represents that the murine antibody CDRs are implanted into the human germline FR region sequences.

The variable regions of the mab179 humanized antibody are shown as follows:

```
>hu179VL1 (Graft (IGKV4-1*01))
                                       SEQ ID NO: 77
DIVMTQSPDSLAVSLGERATINCKASQSVSSDVTWYQQKPGCPPKLLIYY

VSNHYTGVPDRESGSGSGTDFTLTISSLQAEDVAVYYCQQHHRFPLTFGQ

GTKLEIK

>hu179VL2
                                       SEQ ID NO: 78
DIVMTQSPDSLAVSLQERATINCKASQSVSSDVTWYQQKPGQSPKLLIYY

VSNHYTGVPDRFSGSGSGTDFILTISSLQAEDVAVYYCQQHHRFPLTFGQ

GTKLEIK
```

>hu179 VL3
SEQ ID NO: 79
DIVMTQSPDSLAVSLGERATINCKASQSVSSDVTWYQQKPGQSPKLLIYY
VSNHYTGVPDRFSGSGSGTDFTFTISSLQAEDVAVYYCQQHRFPLTFGQ
GIKLEIK

>hu179 VL4
SEQ ID NO: 80
STVMTQSPDSLAVSLGERATINCKASQSVSSDVTWYQQKPGQSPKLLIYY
VSNHYTGVPDRFSGSGSGTDFTLTISSLQAEDVAVYYCQQHRFPLTFGQ
GTKLEIK

>hu179 VL5 (Grafted (IGKV2-29*02))
SEQ ID NO: 81
DIVMTQTPLSLSVTPGQPASISCKASQSVSSDVTWYLQKPGQSPQLLIYY
VSNHYTGVPDRPSGSGSGTDFTLKISRVEAEDVGVYYCQQHRFPLTFGQ
GTKLEIK >hu179VL6
SEQ ID NO: 82
SIVMTQTPLSLSVTPGQPASISCKASQSVSSDVTWYLQKPGQSPQLLIYY
VSNHYTGVPDRFSGSGSGTDFTLKISRVEAEDVGVYYCQQHRFPLTFGQ
GTKLEIK >hu179VL7
SEQ ID NO: 83
SIVMTQTPLSLSVTPGQPASISCKASQSVSSDVTWYLQKPGQSPQLLIYY
VSNHYTGVPDRFSGSGSGTDFTFKISRVEAEDVGVYYCQQHRFPLTFGQ
GTKLEIK >hu179VL8
SEQ ID NO: 84
SIVMTQTPLSLSVTPGQPASISCKASQSVSSDVTWYLQKPGQSPQLLIYY
VSNHYTGVPDRFSGSGYGTDFTLKISRVEAEDVGVYYCQQHRFPLTFGQ
GTKLEIK >hu179VH1 (Grafted)
SEQ ID NO: 85
EVQLVQSGAEVKKPGSSVKVSCKASGGTFSNYLIEWVRQAPGQGLEWMGV
IDPGNGDTNYNENFKGRVTTTADKSTSTAYMELSSLRSEDTAVYYCARED
NTGTAFDYWGQGTTVTVSS >hu179VH2
SEQ ID NO: 86
EVQLVQSGAEVKKPGSSVKVSCKASGYTFSNYLIEWVRQAPGQGLEWMGV
IDPGNGDTNYNENFKGRVTLTADKSTSTAYMELSSLRSEDTAVYYCARED
NTGTAFDYWGQGTTVTVSS >hu179VH3
SEQ ID NO: 87
EVQLVQSGAEVKKPGSSVKVSCKASGYTFSNYLIEWVRQAPGQGLEWIGV
IDPGNGDTNYNENFKGRATLTADKSTSTAYIELSSLRSEDTAVYYCARED
NTGTAFDYWGQGTTVTVSS >hu179VH4
SEQ ID NO: 88
EVQLVQSGABVKKPGSSVKVSCKASGYTFSNYLIEWVKQAPGQGLEWIGV
IDPGNGDTNYNENFKGKATLTADKSTSTAYIELSRLRSEDTAVYYCARED
NTQTAFDYWGQGTTVTVSS >hu179VH5
SEQ ID NO: 89
EVQLVQSGAEVKKPGSSVKVSCKASGYAPSNYLIEWVRQAPGQGLEWIGV
IDPGNGDTNYNENFKGRATLTADKSTSTAYMELSSLRSEDTAVYYCARED
NTGTAFDYWGQGTTVTVSS Note:
The single underlined part represents CDRs, and the double underlined represents back mutation sites.

The aforementioned light and heavy chain variable regions were combined with human germline light and heavy chain constant region sequences to form the final complete light and heavy chain sequences, thus obtaining the antibody with full-length sequence. Exemplarily, for the mab199 humanized antibody in the present disclosure, the heavy chain constant region is the IgG1-YTE constant region shown in SEQ ID NO: 133, and the light chain constant region is the kappa chain constant region shown in SEQ ID NO: 134, but they can also be replaced with other constant regions known in the art.

TABLE 22

Combinations of heavy and light chain variable regions of the mab179 humanized antibody

| Antibody | VH (SEQ ID NO) | VL (SEQ ID NO) |
| --- | --- | --- |
| hu179-01 | 85 | 77 |
| hu179-02 | 85 | 78 |
| hu179-03 | 86 | 77 |
| hu179-04 | 86 | 78 |
| hu179-05 | 87 | 77 |
| hu179-06 | 87 | 78 |
| hu179-07 | 87 | 79 |
| hu179-08 | 87 | 81 |
| hu179-09 | 87 | 82 |
| hu179-10 | 87 | 83 |
| hu179-11 | 87 | 84 |
| hu179-12 | 88 | 77 |
| hu179-13 | 88 | 78 |
| hu179-14 | 89 | 79 |
| hu179-15 | 89 | 80 |
| hu179-16 | 89 | 81 |
| hu179-17 | 89 | 82 |
| hu179-18 | 89 | 83 |
| hu179-19 | 89 | 84 |

The affinity of mab179 humanized antibody with human TSLP was detected by using ELISA method, and the results showed that mab179 humanized antibodies have very good affinity with human TSLP.

(2) Mutations of Hu179 Antibody

It was found by detection that there were hot spots on the HCDR2 and LCDR2 sequences of the mab179 humanized antibody. Therefore, the corresponding hot spots were mutated to eliminate the risk of molecule modification.

In one of the embodiments, GNG of HCDR2 of hu179VH1 was subjected to amino acid mutation, and the sequences of hu179VH1 after mutation are:

hu179VH1-N55Q
SEQ ID NO: 90
EVQLVQSGAEVKKPGSSVKVSCKASGGTFSNYLIEWVRQAPGQGLEWMGV
IDPGQGDTNYNENFKGRVTTTADKSTSTAYMELSSLRSEDTAVYYCARED
NTCAFDYWGQGTTVTVSS

-continued hu179VH1-N55V
SEQ ID NO: 91
EVQLVQSGAEVKKPGSSVKVSCKASGGTFSNYLIEWVRQAPGQGLEWMGV

IDPGVGDTNYNENFKGRVTTTADKSTSTAYMELSSLRSEDTAVYYCARED

NTGTAFDYWGQGTTVTVSS hu179VH1-G56V
SEQ ID NO: 92
EVQLVQSGAEVKKPGSSVKVSCKASGGTFSNYLIEWVRQAPGQGLEWMGV

IDPGNVDTNYNENFKGRVTTTADKSTSTAYMELSSLRSEDTAVYYCARED

NTGTAFDYWGQGTTVTVSS
Note:
The single underlined part represents CDRs, and
the double underlined represents back mutation
sites.

The sequences of HCDR2 regions of the mab179 humanized antibody obtained after mutation are as follows:

TABLE 23

| HCDR2 mutants of the mab179 humanized antibody | |
|---|---|
| hu179 HCDR2-N55Q | VIDPGQGDTNYNENFKG<br>SEQ ID NO: 93 |
| hu179 HCDR2-N55V | VIDPGVGDTNYNENFKG<br>SEQ ID NO: 94 |
| hu179 HCDR2-G56V | VIDPGNVDTNYNENFKG<br>SEQ ID NO: 95 |

Note:
The positions of mutation sites in Table 24 are numbered according to the natural order.

The CDR regions of the mab179 humanized antibody can be obtained from above, and are shown as follows:

TABLE 24

| CDRs of mab179 humanized antibody after mutation | | | |
|---|---|---|---|
| HCDR1 | NYLIE<br>SEQ ID NO: 26 | LCDR1 | KASQSVSSDVT<br>SEQ ID NO: 29 |
| HCDR2<br>(general<br>formula) | VIDPGX$_7$X$_8$DTNYN<br>ENFKG<br>SEQ ID NO: 96 | LCDR2 | YVSNHYT<br>SEQ ID NO: 30 |
| HCDR3 | EDNTGTAFDY<br>SEQ ID NO: 28 | LCDR3 | QQHHRFPLT<br>SEQ ID NO: 31 |

Wherein, $X_7$ is selected from N, Q or V, $X_8$ is selected from G or V.

The hu179VH1 mutants obtained after mutation were combined with the humanized hu179VL to obtain new mab179 humanized antibodies. Exemplary antibodies of combination of hu179VH1 mutant and hu179VL2 are as follows:

TABLE 25

| Combinations of the antibody variable regions after mutation | | | |
|---|---|---|---|
| Variable region | hu179VH1-N55Q | hu179VH1-N55V | hu179VH1-G56V |
| hu179VL2 | hu179-20 | hu179-21 | hu179-22 |

The affinity of the antibody obtained after mutation with human TSLP was detected by using ELISA method. The results showed that antibodies after HCDR2 mutation still maintain relatively high affinity with human TSLP. This showed that the N55Q, N55V and G56V point mutations of HCDR2 of the mab179 humanized antibody will basically not affect the affinity activity of the antibody with TSLP.

According to the same method, N55Q, N55V and G56V point mutations (numbered by the natural order) were made on hu179VH2, hu179VH3, hu179VH4 and hu179VH5 respectively, and the heavy and light chain variable regions obtained by mutation were recombined to obtain new mab179 humanized antibodies. Exemplarily, the mutated sequence of hu179VH3 is shown as follows:

>hu179VH3-N55V
SEQ ID NO: 97
EVQLVQSGAEVKKPGSSVKVSCKASGYTFSNYLIEWVRQAPGQGLEWIG

VIDPGVGDTNYNENFKGRATLTADKSTSTAYIELSSLRSEDTAVYYCAR

EDNTGTAFDYWGQGTTVTVSS
Note:
The single underlined part represents CDRs, and
the double underlined represents back mutation
sites.

In some other examples, LCDR2 of mab179 humanized antibody was subjected to amino acid mutation. Exemplarily, the sequences of hu179VL2 after mutation are as follows:

>hu179VL2-Y50E
SEQ ID NO: 98
DIVMTQSPDSLAVSLGERATINCKASQSVSSDVTWYQQKPGQSPKLLIY

EVSNHYTGVPDRFSGSGSGTDFTLTISSLQAEDVAVYYCQQHHRFPLTF

GQGTKLEIK

>hu179VL2-S52D
SEQ ID NO: 99
DIVMTQSPDSLAVSLGERATINCKASQSVSSDVTWYQQKPGQSPKLLIY

YVDNHYTGVPDRFSGSGSGTDFTLTISSLQAEDVAVYYCQQHHRFPLTF

GQGTKLEIK

>hu179VL2-S52E
SEQ ID NO: 100
DIVMTQSPDSLAVSLGERATINCKASQSVSSDVTWYQQKPGQSPKLLIY

YVENHYTGVPDRFSGSGSGTDFTLTISSLQAEDVAVYYCQQHHRFPLTF

GQGTKLEIK

>hu179VL2-N53Q
SEQ ID NO: 101
DIVMTQSPDSLAVSLGERATINCKASQSVSSDVTWYQQKPGQSPKLLIY

YVSQHYTGVPDRFSGSGSGTDFTLTISSLQAEDVAVYYCQQHHRFPLTF

GQGTKLEIK

>hu179VL2-N53D
SEQ ID NO: 102
DIVMTQSPDSLAVSLGERATINCKASQSVSSDVTWYQQKPGQSPKLLIY

YVSDHYTGVPDRFSGSGSGTDFTLTISSLQAEDVAVYYCQQHHRFPLTF

GQGTKLEIK

```
>hu179VL2-N53E
                                               SEQ ID NO: 103
DIVMTQSPDSLAVSLGERATINCKASQSVSSDVTWYQQKPGQSPKLLIY
YVSEHYTGVPDRFSGSGSGTDFTLTISSLQAEDVAVYYCQQHHREPLTF
GQGTKLEIK

>hu179VL2-H54Y
                                               SEQ ID NO: 104
DIVMTQSPDSLAVSLGERATINCKASQSVSSDVTWYQQKPGQSPKLLIY
YVSNYYTGVPDRFSGSGSGTDFTLTISSLQAEDVAVYYCQQHHRFPLTF
GQGTKLEIK

>hu179VL2-H54D
                                               SEQ ID NO: 105
DIVMTQSPDSLAVSLGERATINCKASQSVSSDYTWYQQKPGQSPKLLIY
YVSNDYTGVPDRFSGSGSGTDFTLTISSLQAEDVAVYYCQQHHRFPLTF
GQGTKLEIK

>hu179VL2-H54E
                                               SEQ ID NO: 106
DIVMTQSPDSLAVSLGERATINCKASQSYSSDYIWYQQKPGQSPKLLIY
YVSNEYTGVPDRFSGSGSGTDFTLTISSLQAEDYAYYYCQQHHRFPLTF
GQGTKLEIK

>hu179VL2-Y55E
                                               SEQ ID NO: 107
DIVMTQSPDSLAVSLGERATINCKASQSVSSDVTWYQQKPGQSPKLLIY
YVSNHETGVPDRFSGSGSCTDFTLTISSLQAEDVAVYYCQQHHRFPLTF
GQGTKLEIK
Note:
The single underlined part represents CDRs, and
the double underlined represents back mutation
sites.
```

The sequences of the mab179 humanized antibody LCDR2 obtained after mutation are as follows:

TABLE 26

| LCDR2 mutants of the mab179 humanized antibody | |
|---|---|
| Mutant | Sequence |
| hu179 LCDR2-Y50E | EVSNHYT<br>SEQ ID NO: 108 |
| hu179 LCDR2-S52D | YVDNHYT<br>SEQ ID NO: 109 |
| hu179 LCDR2-S52E | YVENHYT<br>SEQ ID NO: 110 |
| hu179 LCDR2-N53Q | YVSQHYT<br>SEQ ID NO: 111 |
| hu179 LCDR2-N53D | YVSDHYT<br>SEQ ID NO: 112 |
| hu179 LCDR2-N53E | YVSEHYT<br>SEQ ID NO: 113 |
| hu179 LCDR2-H54Y | YVSNYYT<br>SEQ ID NO: 114 |
| hu179 LCDR2-H54D | YVSNDYT<br>SEQ ID NO: 115 |
| hu179 LCDR2-H54E | YVSNEYT<br>SEQ ID NO: 116 |

TABLE 26-continued

| LCDR2 mutants of the mab179 humanized antibody | |
|---|---|
| Mutant | Sequence |
| hu179 LCDR2-Y55E | YVSNHET<br>SEQ ID NO: 117 |

It can be seen from the above that the general formula of LCDR2 of mab179 humanized antibody is: $X_9VX_{10}X_{11}X_{12}X_{13}T$ (SEQ ID NO: 118), wherein $X_9$ is selected from Y or E, $X_{10}$ is selected from S, D or E, $X_{11}$ is selected from N, Q, D or E; $X_{12}$ is selected from H, Y, D or E; $X_{13}$ is selected from E or Y. The CDR regions of the mab179 humanized antibody are as shown in the following table:

TABLE 27

| CDRs of mab179 humanized antibody | | | |
|---|---|---|---|
| HCDR1 | NYLIE<br>SEQ ID NO: 26 | LCDR1 | KASQSVSSDVT<br>SEQ ID NO: 29 |
| HCDR2 | VIDPGX$_7$X$_8$DTNYNENFKG<br>SEQ ID NO: 96 | LCDR2 | X$_9$VX$_{10}$X$_{11}$X$_{12}$X$_{13}$T<br>SEQ ID NO: 118 |
| HCDR3 | EDNTGTAFDY<br>SEQ ID NO: 28 | LCDR3 | QQHHRFPLT<br>SEQ ID NO: 31 |

Wherein, $X_7$ is selected from N, Q or V, $X_8$ is selected from G or V; $X_9$ is selected from Y or E; $X_{10}$ is selected from S, D or E; $X_{11}$ is selected from N, Q, D or E; $X_{12}$ is selected from H, Y, D or E; $X_{13}$ is selected from E or Y.

The hu179VL2 mutants obtained after mutation were combined with the humanized hu179 heavy chain variable regions to obtain new mab179 humanized antibodies. As an example, hu179VL2 mutants were combined with hu179VH1, hu179VH3, and the CDRs and the combinations of the heavy and light chain variable regions of the obtained mab179 humanized antibodies are shown as follows:

TABLE 28

| The sequences of CDR regions of the mab179<br>humanized antibody after LCDR2 mutation | | | |
|---|---|---|---|
| HCDR1 | NYLIE<br>SEQ ID NO: 26 | LCDR1 | KASQSVSSDVT<br>SEQ ID NO: 29 |
| HCDR2 | VIDPGNGDTNYNENFKG<br>SEQ ID NO: 27 | LCDR2 | X$_5$VX$_6$X$_7$X$_8$X$_9$T<br>SEQ ID NO: 118 |
| HCDR3 | EDNTGTAFDY<br>SEQ ID NO: 28 | LCDR3 | QQHHRFPLT<br>SEQ ID NO: 31 |

Wherein, $X_5$ is selected from Y or E; $X_6$ is selected from S, D or E; $X_7$ is selected from N, Q, D or E; $X_8$ is selected from H, Y, D or E; $X_9$ is selected from E or Y.

TABLE 29

| Combinations of heavy and light chain variable regions<br>of mab179 humanized antibody after LCDR2 mutation | | |
|---|---|---|
| Antibody | VH (SEQ ID NO) | VL (SEQ ID NO) |
| hu179-23 | 85 | 102 |
| hu179-24 | 85 | 104 |
| hu179-25 | 87 | 98 |
| hu179-26 | 87 | 99 |

TABLE 29-continued

Combinations of heavy and light chain variable regions of mab179 humanized antibody after LCDR2 mutation

| Antibody | VH (SEQ ID NO) | VL (SEQ ID NO) |
|---|---|---|
| hu179-27 | 87 | 100 |
| hu179-28 | 87 | 101 |
| hu179-29 | 87 | 103 |
| hu179-30 | 87 | 105 |
| hu179-31 | 87 | 106 |
| hu179-32 | 87 | 107 |

The affinity of the mab179 humanized antibodies obtained after LCDR2 mutation with human TSLP was detected by using ELISA method. The results showed that antibodies obtained after hot spot site mutation to LCDR2 still have relatively good affinity with human TSLP. This showed that hot spot site mutation to LCDR2 will not affect the binding activity of the mab179 humanized antibodies.

According to the same method, N53Q, N53D, N53S, H54Y, Y50E, S52D, S52E, N53E, H54D, H54E, Y55E mutations were made on LCDR2 of hu179VL3, hu179VL4, hu179VL5, hu179VL6, hu179VL7 and hu179VL8. The light chain variable regions and the heavy chain variable regions after mutation were combined to form new mab humanized antibodies. In one embodiment, the sequence of hu179VL8 after mutation is shown as follows:

hu179L8-N53E:
SEQ ID NO: 119
SIVMTQPLSLSVTPGQPASISCKASQSVSSDVTWYLQKPGQSPQLLIYYV
SEHYTGVPDRFSGSGYGTDFTLKISRVEAEDVGVYYCQQHHRFPLTFGQG
TKLEIK hu179VL8-N53E and hu179VH3-N55V obtained by mutation were combined to obtain a new antibody molecule hu179-33, the CDR sequences of which are shown as follows:

TABLE 30

CDR regions of hu179-33 antibody

| HCDR1 | NYLIE SEQ ID NO: 26 | LCDR1 | KASQSVSSDVT SEQ ID NO: 29 |
|---|---|---|---|
| HCDR2-N55V | VIDPGVGDTNYNENFKG SEQ ID NO: 94 | LCDR2-N53E | YVSEHYT SEQ ID NO: 113 |
| HCDR3 | EDNTGTAFDY SEQ ID NO: 28 | LCDR3 | QQHHRFPLT SEQ ID NO: 31 |

The binding activity of antibodies obtained after mutation to human TSLP was detected by Biacore. Exemplary binding activity of antibodies is shown as follows:

TABLE 31

Affinity of hu179-33 with human TSLP

| Antibody | Affinity to huTSLP KD (M) |
|---|---|
| AMG157 | 8.12E-12 |
| hu179-33 | 9.03E-13 |

The results showed that antibody hu179-33 has relatively high specific binding activity to human TSLP. This indicated that point mutations of hot spots on both HCDR2 and LCDR2 will not affect the affinity of the mab179 humanized antibody to human TSLP. It can be seen that in the mab179 humanized antibody molecule, mutations of N55Q, N55V, G56V made on HCDR2, and mutations of N53Q, N53D, N53S, H54Y, Y50E, S52D, S52E, N53E, H54D, H54E, Y55E made on LCDR2 will not affect the binding of the antibody to human TSLP, i.e., will not affect the activity of anti-TSLP antibodies.

5.4 Selection and Back Mutations of the Human FR Regions for Mab199 Antibody

For mab199, IGHV1-46*01 and HJ6*01 were selected as templates for the VH, and IGKV1-39*01 and IGKJ4*01 were selected as templates for the VL. The CDR regions of the murine antibody were grafted to the selected humanized templates, and the FR region was subjected to back mutation to obtain light chain and heavy chain variable regions with different sequences. The back mutations are as shown in Table 32.

TABLE 32

Design of back mutations for mab199

| hu199VL | | hu199VH | |
|---|---|---|---|
| hu199VL1 | Grafted | hu199VH1 | Grafted |
| hu199VL2 | I48V | hu199VH2 | R71V, T73K, V78A |
| hu199VL3 | A43S, K45Q, I48V, D70Q | hu199VH3 | M69L, R71V, T73K, V78A |
| hu199VL4 | G66V | hu199VH4 | M48I, V67A, M69L, R71V, T73K, V78A |
| hu199VL5 | I48V, G66V | hu199VH5 | R38K, M48I, R66K, V67A, M69L, R71V, T73K, V78A |
| hu199VL6 | A43S, K45Q, I48V, G66V, D70Q | hu199VH6 | R38K, R66K, R71V, T73K, V78A |
| | | hu199VH7 | R38K, R67K, M69L, R71V, T73K, V78A |

Note:
For example, I48V represents that according to the Kabat numbering system, I at position 48 is mutated back to V. Grafted represents that the murine antibody CDRs are implanted into the human germline FR region sequences.

The variable regions of the mab199 humanized antibody are shown as follows:

>hu199VL1 (Grafted)
SEQ ID NO: 120
DIQMTQSPSSLSASVGDRVTITCRASENIYSYLAWYQQKPGKAPKLLIY
FAKTLAEGVPSRFSGSGSGTDFTLTISSLQPEDFATYYCQHHYGTPWTF
GGGTKVEIK >hu199VL2
SEQ ID NO: 121
DIQMTQSPSSLSASVGDRVTTTCRASENIYSYLAWYQQKPGKAPKLLVY
FAKTLAEGVPSRFSGSGSGTDFTLTISSLQPEDFATTYCQHHYGTPWT
FGGGTKVEIK >hu199VL3
SEQ ID NO: 122
DIQMTQSPSSLSASVGDRVTITCRASENIYSLAWYQQKPGKSPQLLVYF
AKTLAEGVPSRFSGSGSGTQFTLTISSLQPEDFATYYCQHHYGTPWTFG
GGTKVEIK >hu199VL4

SEQ ID NO: 123

DIQMTQSPSSLSASVCDRVTITC<u>RASENIYSYLA</u>WYQQKPGKAPKLLIY

<u>FAKTLAEG</u>VPSRFSGS<u>V</u>SGTDFTLTISSSLQPEDFATYYC<u>QHHYGTPWT</u>

FGGGTKVEIK

>hu199VL5

SEQ ID NO: 124

DIQMTQSPSSLSASVGDRVTITC<u>RASENIYSYLA</u>WYQQKPGKAPKLL<u>V</u>Y

<u>FAKTLAEG</u>VPSRFSGS<u>V</u>SGTDFTLISSLQPEDFATYYC<u>QHHYGTPWT</u>FG

GGTKVEIK

>hu199VL6

SEQ ID NO: 125

DIQMTQSPSSLSASVGDRVTITC<u>RASENIYSYLA</u>WYQQKPGKS<u>PQ</u>LL<u>V</u>Y

<u>FAKTLAEG</u>VPSRFSGS<u>V</u>SGT<u>Q</u>FTLTSSLQPEDFATYYC<u>QHHYCPWT</u>FGG

GTKVEIK

>hu199VH1 (Grafted)

SEQ ID NO: 126

EVQLVQSGAEVKKPGASVKVSCKASGYTFT<u>TYWMH</u>WVRQAPGQGLEWMG

<u>MIDPSDSETTLIQKFK</u>DRVTMT<u>RD</u>T<u>S</u>TST<u>V</u>YMELSSLRSEDTAVYYCAR

<u>TLDGYYDY</u>WGQGTTVTVSS

>hu199VH2

SEQ ID NO: 127

EVQLVQSGAEVKKPGASVKVSCKASGYTFT<u>TYWMH</u>WVRQAPGQGLEWMG

<u>MIDPSDSETTLIQKFK</u>DRVTMT<u>VD</u>K<u>S</u>TST<u>A</u>YMELSSLRSEDTAVYYCAR

<u>TLDGYYDY</u>WGQGTTVTVSS

>hu199VH3

SEQ ID NO: 128

EVQLVQSGAEVKKPGASVKVSCKASGYTFT<u>TYWMH</u>WVRQAPGQGLEWMG

<u>MIDPSDSETTLIQKFK</u>DRVT<u>L</u>T<u>VD</u>K<u>S</u>TST<u>A</u>YMELSSLRSEDTAVYYCAR

<u>TLDGYYDY</u>WQQGTTVTVSS

>hu199VH4

SEQ ID NO: 129

EVQLVQSGAEVKKPGASVKVSCKASGYTFT<u>TYWMH</u>WVRQAPGQGLEW<u>I</u>G

<u>MIDPSDSETTLIQKFK</u>D<u>RA</u>TLT<u>VD</u>K<u>S</u>TST<u>A</u>YMELSSLRSEDTAVYYCAR

<u>TLDGYYDY</u>WGQGTTVTVSS hu199VH5

SEQ ID NO: 130

EVQLVQSGAEVKKPGASVKVSCKASGYTFT<u>TYWMH</u>WV<u>K</u>QAPGQGLEW<u>I</u>G

<u>MIDPSDSETTLIQKFK</u>D<u>KA</u>TL<u>T</u>VDKSTST<u>A</u>YMELSSLRSEDTAVYYCAR

<u>TLDGYYDY</u>WGQGTTVTVSS

>hu199VH6

SEQ ID NO: 131

EVQLVQSGAEVKKPGASVKVSCKASGYTFT<u>TYWMH</u>WV<u>K</u>QAPGQGLEWMG

<u>MIDPSDSETTLIQKFK</u>D<u>K</u>VTMT<u>VD</u>K<u>S</u>TST<u>A</u>YMELSSLRSEDTAVYYCAR

<u>TLDGYYDY</u>WGQGTTVTVSS

>hu199VH7

SEQ ID NO: 132

EVQLVQSGAEVKKPGASVKVSCKASGYTFT<u>TYWMH</u>WV<u>K</u>QAPGQGLEWMG

<u>MIDPSDSETTLIQKFK</u>D<u>K</u>VT<u>L</u>T<u>VD</u>K<u>S</u>TST<u>A</u>YMELSSLRSEDTAVYYCAR

<u>TLDGYYDY</u>WGQGTTVTVSS

Note:

The single underlined part represents CDRs, and the double underlined represents back mutation sites.

The aforementioned light and heavy chain variable regions were combined with human germline light and heavy chain constant region sequences to form the final complete light and heavy chain sequences, thus obtaining the antibody with full-length sequence. For the mab199 humanized antibodies, if there is no clear description in the present disclosure, the light chain constant region is the constant region shown in SEQ ID NO: 134, and the heavy chain constant region is the constant region shown in SEQ ID NO: 133.

The obtained mab199 humanized antibodies are shown as follows:

TABLE 33

Sequences of heavy and light chain variable regions of the mab199 humanized antibodies

| Antibody | VH (SEQ ID NO) | VL (SEQ ID NO) |
| --- | --- | --- |
| hu199-01 | 127 | 120 |
| hu199-02 | 127 | 121 |
| hu199-03 | 127 | 122 |
| hu199-04 | 127 | 123 |
| hu199-05 | 127 | 124 |
| hu199-06 | 127 | 125 |
| hu199-07 | 128 | 120 |
| hu199-08 | 128 | 121 |
| hu199-09 | 128 | 122 |
| hu199-10 | 128 | 123 |
| hu199-11 | 128 | 124 |
| hu199-12 | 128 | 125 |
| hu199-13 | 129 | 120 |
| hu199-14 | 129 | 121 |
| hu199-15 | 129 | 122 |
| hu199-16 | 129 | 123 |
| hu199-17 | 129 | 124 |
| hu199-18 | 129 | 125 |
| hu199-19 | 130 | 120 |
| hu199-20 | 130 | 121 |
| hu199-21 | 130 | 122 |
| hu199-22 | 130 | 123 |
| hu199-23 | 130 | 124 |
| hu199-24 | 130 | 125 |
| hu199-25 | 131 | 120 |
| hu199-26 | 131 | 121 |
| hu199-27 | 131 | 122 |
| hu199-28 | 131 | 123 |
| hu199-29 | 131 | 124 |
| hu199-30 | 131 | 125 |
| hu199-31 | 132 | 120 |

TABLE 33-continued

Sequences of heavy and light chain variable regions of the mab199 humanized antibodies

| Antibody | VH (SEQ ID NO) | VL (SEQ ID NO) |
|---|---|---|
| hu199-32 | 132 | 121 |
| hu199-33 | 132 | 122 |
| hu199-34 | 132 | 123 |
| hu199-35 | 132 | 124 |
| hu199-36 | 132 | 125 |

The activity of the mab199 humanized antibodies blocking the binding of TSLP to TSLP receptor was detected by using ELSA method, and the detection results are as follows:

TABLE 34

Activity of mab199 humanized antibody blocking the binding of TSLP to TSLP receptor

| Antibody | IC50 (nM) | Antibody | IC50 (nM) | Antibody | IC50 (nM) | Antibody | IC50 (nM) |
|---|---|---|---|---|---|---|---|
| hu199-01 | 0.1912 | hu199-10 | 0.3910 | hu199-191 | 0.6584 | hu199-28 | 0.4619 |
| hu199-02 | 0.2193 | hu199-11 | 0.3648 | hu199-20 | 0.4001 | hu199-29 | 0.5543 |
| hu199-03 | 0.2077 | hu199-12 | 0.3700 | hu199-21 | 0.5353 | hu199-30 | 0.3493 |
| hu199-04 | 0.4242 | hu199-13 | 0.2395 | hu199-22 | 0.3449 | hu199-31 | 0.3044 |
| hu199-05 | 0.4726 | hu199-14 | 0.3112 | hu199-23 | 0.3370 | hu199-32 | 0.2870 |
| hu199-06 | 0.3806 | hu199-15 | 0.2866 | hu199-24 | 0.4960 | hu199-33 | 0.2055 |
| hu199-07 | 0.2834 | hu199-16 | 0.7367 | hu199-25 | 0.2460 | hu199-34 | 0.7107 |
| hu199-08 | 0.2828 | hu199-17 | 0.6111 | hu199-26 | 0.3651 | hu199-35 | 0.4849 |
| hu199-09 | 0.2732 | hu199-18 | 0.4806 | hu199-27 | 0.3544 | hu199-36 | 0.7273 |
| Ch199 | 0.4266 | | | | | | |

The results showed that the mab199 humanized antibodies still have relatively high activity of blocking the binding of TSLP to TSLP receptor.

5.5 Antibody Constant Regions

The heavy chain constant region of humanized antibody and chimera antibody can be selected from the group consisting of the constant regions of IgG1, IgG2, IgG4 and variants thereof. Exemplarily, IgG1-YTE constant region was used in the present disclosure, and its sequence is as shown in SEQ ID NO: 133. The light chain constant region can be selected from the light chain constant regions of human κ, λ chain or variants thereof. Exemplarily, human κ chain constant region was used in the present disclosure, and its sequence is as shown in SEQ ID NO: 134.

>IgG1-YTE heavy chain constant region:
SEQ ID NO: 133
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTL<u>YITRE</u>PEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK
Note:
Underlined refers to the designed M252Y, S254T, T256E mutations >κ light chain constant region:
SEQ ID NO: 134
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGEC

The humanized heavy and light chain variable regions in the present disclosure were recombined with the above constant regions to obtain the full-length sequences of the heavy and light chains. Exemplarily, the antibody sequences are as follows:

```
hu3-13 antibody heavy chain:
                                         SEQ ID NO: 135
EVQLVQSGAEVKKPGASVKVSCKASGYTFDDYMNWVRQAPGQRLEWMGII

SPYNGGTSYNQKFKGRVTLTVDKSASTAYMELSSLRSEDTAVYYCAREDYDY

DGYAMDYWGQGTTVTVSSASTKGPSVFPLAPSSKSTSGGTAALGCLVKDYFPEP

VTVSWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLYITREPEVTCVVVDVS

HEDPEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEAL

HNHYTQKSLSLSPGK hu3-13 antibody light chain:
                                         SEQ ID NO: 136
EIVLTQSPATLSLSPGERATLSCRASSSVSYMHWYQQKPGQAPRPWIYATSNLA

SGVPARFSGSGSGTSYTLTISRLEPEDFAVYYCQQSDSGREFGGGTKVEIKRTVA

APSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC hu119-30 antibody heavy chain
                                         SEQ ID NO: 137
EAQLVQSGAEVKKPGSSVKVSCKASGFTFSTYNMHWVRQAPGQGLEWIGAI

YPGNGETSYNQKFKDRATLTVDKSTRTAYMELSSLRSEDTAVYYCAREDDYG

EGYFDVWGQGTTVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVD

KKVEPKSCDKTHTCPPCPAPELLGGPSVFLFPPKPKDTLYITREPEVTCVVVDVSH

EDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALH

NHYTQKSLSLSPGK hu119-30 antibody light chain
                                         SEQ ID NO: 138
DIVLTQSPATLSLSPGERATLSCRASESVDSSGLSFMHWYQQKPGQPPRLLLYR

ASNLGSGIPARFSGSGSGTDFTLTISSLEPEDFAVYYCQQINTDPLTFGQGTKLEI

KRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSENRGEC hu179-33 antibody heavy chain
                                         SEQ ID NO: 139
EVQLVQSGAEVKKPGSSVKVSCKASGYTFSNYLIEWVRQAPGQGLEWIGVID

PGYGDTNYNENFKGRATLTADKSTSTAYIELSSLRSEDTAVYYCAREDNTGTA

FDYWGQGTTVTVSSASTKGPSVFPLAPSSKSTSGGTAALGCLVKDYFPEPVTVSW

NSGALTSGVMTFPAVLQSSGLYSLSSVVTVPSSSLGTQTYICNVNHKPSNTKVDKKV

EPKSCDKTHTCPPCPAPELLGGPSVFLFPPKPKDTLYITREPEVTCVVVDVSHEDP

EVKFNWYVDGVEVHNAKTKPREEQYNSTYRVVSVLTVLHQDWLNGKEYKCKVSN
```

```
-continued
KALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYT

QKSLSLSPGK hu179-33 antibody light chain
                                            SEQ ID NO: 140
SIVMTQTPLSLSVTPGQPASISCKASQSVSSDVTWYLQKPGQSPQLLIYYVSEH

YTGVPDRFSGSGYGTDFTLKISRVEAEDVGVYYCQQHHRFPLTFGQGTKLEIK

RTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC hu199-36 antibody heavy chain
                                            SEQ ID NO: 141
EVQLVQSGAEVKKPGASVKVSCKASGYTFTTYWMHWVKQAPGQGLEWMG

MIDPSDSETTLIQKFKDKVTLTVDKSTSTAYMELSSLRSEDTAVYYCARTLDG

YYDYWGQGTTVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLYITREPEVTCVVVDVSHED

PEVKFNWYVDGVEVHNAKTKPREEQYNSTYRVYSVLTVLHQDWLNGKEYKCKVS

NKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHY

TQKSLSLSPGK hu199-36 antibody light chain:
                                            SEQ ID NO: 142
DIQMTQSPSSLSASVGDRVTITCRASENIYSYLAWYQQKPGKSPQLLVYFAKT

LAEGVPSRFSGSVSGTQFTLTISSLQPEDFATYYCQHHYGTPWTFGGGTKVEIK

RTVAAPSVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGEC
Note:
The underlined part represents CDR, and the italicized part
represents constant region.
```

AMG157 was used as a positive control for the present disclosure, and its sequence is as shown in SEQ ID NO: 143 and SEQ ID NO: 144.

```
Heavy chain sequence of AMG157
                                            SEQ ID NO: 143
QMQLVESGGGVVQPGRSLRLSCAASGFTFRTYGMHWVRQAPGKGLEWVAV

IWYDGSNKHYADSVKGRFTITRDNSKNTLNLQMNSLRAEDTAVYYCARAP

QWELYHEAEDIWGQGTMVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSHEDPEVQFNWYVDGVEVHNAKTKPREEQFNST

FRVVSVLTVVHQDWLNGKEYKCKVSNKGLPAPIEKTISKTKGQPREPQVY

TLPPSREEMTKNQVSLTCLVKGFYPSDIAVEWESNGQPENNYKTTPPMLD

SDGSFFLYSKLTVDKSRWQQGNVFSCSVMHEALHNHYTQKSLSLSPGK

Light chain sequence of AMG157
                                            SEQ ID NO: 143
SYVLTQPPSVSVAPGQTARITCGGNNLGSKSVHWYQQKPGQAPVLYYYDD

SDRPSWIPERESGSNSGNTATLTISRGEACDEADYYCQYWDSSSDHYYFG

-continued
GGTKLTVLGQPKAAPSVTLFPPSSEELQANKATLVCLISDFYPGAVTVAW

KADSSPVKAGVETTTPSKQSNNKYAASSYLSLTPEQWKSHRSTSCQVTHE

GSTVEKTVAPTECS
```

In addition, when testing the antibody activity, the present disclosure also used human TSLP receptor and human IL7Rα to construct cell lines, and their sequences are as follows:

```
Full-length amino acid sequence of human TSLP
receptor:
                                            SEQ ID NO: 145
MGRLVLLWGAAVFLLGGWMALGQGGAAEGVQIQIIYFNLETVQVTWNAS

KYSRTNLTFHYRFHGDEAYDQCTNYLLQEGHTSGCLLQAEQRDDILYFS

IRHGTHPVFTASRWMVYYLKPSSPKHVRFSWHQDAVTVTCSDLSYGDLL

YEVQYRSPFDTEWQSKQENTCNVTIEGLDAEKCYSFWVRVKAMEDVYGP

DTYPSDWSEVTCWQRGEIRDACAETPTPPKPKLSKFILISSLAILLMVS

LLLLSLWKLWRVKKFLIPSVPDPKSIFPGLFEIHQGNFQEWITDTQNVA
```

-continued

HLHKMAGAEQESGPEEPLVVQLAKTEAESPRMLDPQTEEKEASGGSLQL

PHQPLQGGDVVTIGGFTFVMNDRQLAKTEAESPRMLDPQTEEKEASGGS

LQLPHQPLQGGDVVTIGGFTFVMNLSYVAL

Note:
The underlined part refers to the signal peptide

Full-length amino acid sequence of human IL7Rα
(Uniprot ID: P16871)
SEQ ID NO: 146
<u>MTILGTTFGMVFSLLQVVSGE</u>SGYAQNGDLEDAELDDYSFSCYSQLEVN

GSQHSLTCAFEDPDVNTTNLEFEICGALVEVKCLNFRKLQEIYFIETKK

FLLIGKSNICKVGEKSLTCKKIDLTTIVKPEAPFDLSVIYREGANDFVV

TFNTSHLQKKYVKVLMHDVAYRQEKDENKWTHVNLSSTKLTLLQRKLQP

AAMYEIKVRSIPDHYFKGFWSEWSPSYYFRTPEINNSSGEMDPILLTIS

ILSFFSVALLVILACVLWKKRIKPIVWPSLPDHKKTLEHLCKKPRKNLN

VSFNPESFLDCQIHRVDDIQARDEVEGFLQDTFPQQLEESEKQRLGGDV

QSPNCPSEDVVITPESFGRDSSLTCLAGNVSACDAPILSSSRSLDCRES

GKNGPHVYQDLLLSLGTTNSTLPPPFSLQSGILTLNPVAQGQPILTSLG

SNQEEAYVTMSSPYQNQ

Note:
The underlined part refers to the signal peptide

The antibodies of the present disclosure can be cloned, expressed and purified using conventional gene cloning and recombinant expression methods.

TEST EXAMPLES

Biological Evaluation of In Vitro Activity

Test Example 1: ELSA Detection of the Binding of Anti-TSLP Antibodies to Human TSLP Human TSLP-his (SEQ ID NO: 1) was diluted to 1 μg/ml with pH 7.4 PBS (Shanghai BasalMedia, B320) buffer, added at 100 μg/well to 96-well microtiter plates (Corning, CLS3590-100EA) and incubated overnight at 4° C. After discarding the liquid, 200 μl/well of blocking solution with 5% skimmed milk (Bright Dairy skimmed milk powder) diluted in PBS was added and incubated in a 37° C. incubator for 2 hours for blocking. After blocking was over, the blocking solution was discarded, and the plates were washed with PBST buffer (PBS containing 0.1% tween-20, pH 7.4) for 3 times. The antibodies to be tested and the positive antibody AMG157 at different concentrations diluted with the sample diluent were added at 100 μl/well and incubated in a 37° C. incubator for 1 hour. After incubation was over, the plates were washed with PBST for 3 times. HRP-labeled goat anti-mouse secondary antibody (Jackson Immuno Research, 115-035-003) diluted with sample diluent was added at 100 μl/well and incubated at 37° C. for 1 hour. After washing the plate with PBST for 6 times, 50 μl/well TMB chromogenic substrate (KPL, 52-00-03) was added and incubated at room temperature for 10-15 min, and 50 μl/well 1 M $H_2SO_4$ was added to stop the reaction. The absorption value was read by using a NOVOStar microplate reader at 450 nm. The EC50 value of the TSLP antibodies binding to TSLP was calculated and the results are shown in the following table.

TABLE 35

Results of binding activity of antibodies to human TSLP

| Antibody | EC50 (nM) |
|---|---|
| Ch3 | 0.4929 |
| hu3-01 | 0.8494 |
| hu3-02 | 0.6285 |
| hu3-03 | 0.5545 |
| hu3-04 | 0.4353 |
| hu3-05 | 0.5168 |
| hu3-06 | 0.594 |
| hu3-07 | 0.3853 |
| hu3-08 | 0.4687 |
| hu3-09 | 0.4941 |
| hu3-10 | 0.3879 |
| hu3-12 | 0.1519 |
| hu3-13 | 0.1477 |
| Ch119 | 0.851 |
| hu119-01 | 0.107 |
| hu119-02 | 0.1938 |
| hu119-03 | 0.1593 |
| hu119-04 | 0.1881 |
| hu119-05 | 0.1445 |
| hu119-06 | 0.2206 |
| hu119-07 | 0.2132 |
| hu119-08 | 0.2015 |
| hu119-09 | 0.1492 |
| hu119-10 | 0.2329 |
| hu119-11 | 0.174 |
| hu119-12 | 0.2034 |
| hu119-13 | 0.3438 |
| hu119-14 | 0.345 |
| hu119-15 | 0.3497 |
| hu119-16 | 0.366 |
| hu119-17 | 0.3515 |
| hu119-18 | 0.3455 |
| hu119-19 | 0.3533 |
| hu119-20 | 0.3412 |
| hu119-21 | 0.3987 |
| hu119-22 | 0.351 |
| hu119-23 | 0.3404 |
| hu119-24 | 0.3446 |
| hu119-25 | 0.3575 |
| hu119-26 | 0.3782 |
| hu119-27 | 0.3347 |
| hu119-28 | 0.2648 |
| hu119-29 | 0.2729 |
| hu119-28 | 0.2648 |
| hu119-29 | 0.2729 |
| Ch179 | 0.2023 |
| hu179-01 | 0.1248 |
| hu179-02 | 0.1697 |
| hu179-03 | 0.138 |
| hu179-04 | 0.1886 |
| hu179-05 | 0.1416 |
| hu179-06 | 0.2188 |
| hu179-07 | 0.4478 |
| hu179-08 | 1.01615 |
| hu179-09 | 0.1573 |
| hu179-10 | 0.19 |
| hu179-11 | 0.1369 |
| hu179-12 | 0.1437 |
| hu179-13 | 0.2011 |
| hu179-14 | 0.2053 |
| hu179-15 | 0.2035 |
| hu179-16 | 0.2287 |
| hu179-17 | 0.218 |
| hu179-18 | 0.2458 |
| hu179-19 | 0.1616 |
| hu179-20 | 0.7077 |
| hu179-21 | 0.9784 |
| hu179-22 | 0.7519 |
| hu179-23 | 0.997 |
| hu179-24 | 0.6358 |
| hu179-25 | 0.1313 |
| hu179-26 | 0.2006 |
| hu179-27 | 0.1799 |
| hu179-28 | 0.0906 |
| hu179-29 | 0.2041 |
| hu179-30 | 0.246 |

TABLE 35-continued

Results of binding activity of antibodies to human TSLP

| Antibody | EC50 (nM) |
| --- | --- |
| hu179-31 | 0.2012 |
| hu179-32 | 0.145 |
| Ch199 | 0.5157 |
| AMG157 | 0.7219 |

The results showed that the antibodies in the present disclosure have very good binding activity with human TSLP.

Test Example 2: Biacore Detection of the Affinity of Anti-TSLP Humanized Antibodies with Different Species of TSLP The affinity of the humanized TSLP antibodies to be tested with human and cyno TSLP was detected by a Biacore T200 (GE) instrument.

The molecules to be tested were affinity captured by Protein A biosensor chips (Cat. #29127556, GE). Then the antigens (huTSLP-his, cynoTSLP-his, prepared in Example 1) were allowed to flow across the chip surface, and the reaction signal was detected in real time by using the Biacore T200 instrument to obtain the binding and dissociation curves. After the dissociation of each experimental cycle was completed, the biosensor chips were washed and regenerated with glycine-hydrochloric acid regeneration solution (pH 1.5, Cat. #BR-1003-54, GE). The data was fit with a (1:1) Langmuir model by using BIAevaluation version 4.1, GE software to obtain the affinity value, as shown in the following table.

TABLE 36

Affinity of anti-TSLP antibodies with TSLP of different species

| Antibody | affinity to huTSLP KD (M) | affinity to Cyno TSLP KD (M) |
| --- | --- | --- |
| AMG157 | 8.12E−12 | 9.22E−12 |
| hu179-33 | 9.03E−13 | 3.04E−11 |
| hu3-13 | 1.0E−12 | 3.40E−10 |
| hu119-30 | 5.0E−12 | 1.95E−09 |
| hu199-36 | 10.5E−12 | 1.72E−11 |

The results showed that the anti-TSLP antibodies in the present disclosure have relatively high affinity to human TSLP, and can also bind to cyno TSLP.

Test Example 3: ELSA-Based Experiment of Anti-TSLP Antibodies Blocking the Binding of TSLP to TSLP Receptor The TSLP receptor has two subunits, TSLPR and IL7R, of which TSLPR is a specific receptor for TSLP, and IL7R is a common receptor for TSLP and IL7. TSLP binds first to TSLPR and then to IL7R. This test example was used to identify whether the TSLP antibodies can block the binding of TSLP to the extracellular domain of recombinant expressed TSLPR receptor protein.

The ELISA plates were coated with human-TSLPR-Fc-ECD (2 μg/ml, SEQ ID NO: 5) and incubated overnight at 4° C. After discarding the liquid, 200 μl/well blocking solution with 5% skimmed milk diluted in PBS was added and incubated in a 37° C. incubator for 2 hours for blocking. After blocking was over, the blocking solution was discarded and the plates were washed with PBST buffer (PBS containing 0.05% tween-20, pH7.4) for 3 times. Biotin-labeled huTSLP-Fc antigen was prepared at 3 nM, and the antibodies to be tested was serially diluted starting from 200 nM. The antigen and antibody were 1:1 mixed, then placed at 37° C. for 15 min, added at 100 μl per well to the microtiter plates and placed at 37° C. for 1 h. The plates were washed with PBST for 3 times. Streptavidin-Peroxidase Polymer diluted to 1:4000 with the sample diluent was added at 100 μl/well and incubated at 37° C. for 1 hour. After washing the plates with PBST for 5 times, 100 μl/well TMB chromogenic substrate (KPL, 52-00-03) was added and incubated at room temperature for 3-10 min, and 100 μl/well 1M $H_2SO_4$ was added to stop the reaction. The absorption value was read by using a NOVOStar microplate reader at 450 nm. The IC50 value of the TSLP antibodies blocking the binding of TSLP to TSLPR was calculated and the results are shown in Table 37 and FIG. 1.

TABLE 37

Results of blocking activity of antibodies

| Antibody | hu179-33 | hu119-30 | hu3-13 | hu199-36 |
| --- | --- | --- | --- | --- |
| IC50 (nM) | 0.5038 | 0.5192 | 0.4975 | 0.5693 |

The results showed that all the antibodies of the present disclosure can strongly inhibit the binding of TSLP to its receptor TSLPR.

Test Example 5: FACS-Based Experiment of TSLP Antibody Blocking the Binding of TSLP to TSLP Receptor This test example was used to identify whether the anti-TSLP antibodies can respectively block the binding of TSLP to TSLPR/IL7R receptors on the surface of CHOK1 cell line.

The detailed method was: CHOK1-TSLPR/IL7R was cultured with DME/F12 containing 10% FBS, 1 mg/ml G418 and 10 μg/ml puromycin. CHOK1-TSLPR/IL7R cells in good condition were centrifuged (1000 rpm, 5 min), washed once with 2% FBS in PBS. The cells were counted and adjusted to a cell concentration of $1 \times 10^6$/ml. 50 μl of cells were added to round-bottomed 96-well plates. The antibodies to be tested were diluted with PBS solution containing 2% BSA, with an initial concentration of 20 nM and 8 gradients at a ratio of 1:4. Biotin-labeled TSLP-Fc antigen was prepared at 2 nM. The antigen and antibody were 1:1 mixed and placed at 37° C. for 15 min. The mixture was added at 50 μl per well to the 96-well plates where the cells have been plated, and incubated at 4° C. for 1 hour. After incubation was over, the plates were centrifuged at 4° C. (800 g, 5 min) and the supernatant was discarded. The plates were washed twice with 200 μl of pre-cooled PBS by centrifugation. 1:1000 diluted PE-SA secondary antibody was added and incubated at 4° C. in the dark for 40 min. Then the plates were centrifuged at 4° C. (800 g, 5 min) and the supernatant was discarded. 200 μl of pre-cooled PBS was added to blow up the cells, which were washed by centrifugation at 4° C. for three times. 100 μl PBS was added and the plate was loaded onto the machine for plate reading. The IC50 value of TSLP antibodies blocking the binding of TSLP to TSLPR/IL7R was calculated according to the value of the fluorescence signals. The results are as shown in Table 38.

TABLE 38

| Results of antibodies blocking cell surface TSLPR | | | | | |
|---|---|---|---|---|---|
| Antibody | AMG157 | hu179-33 | hu119-30 | hu3-13 | hu199-36 |
| IC50 (nM) | 0.2068 | 0.1867 | 0.1368 | 0.1325 | 0.2270 |

The results showed that the antibodies of the present disclosure can all relatively strongly block the binding of TSLP to cell surface TSLPR/IL7R.

Test Example 6: Anti-TSLP Antibodies Inhibited TSLP-Induced Chemokine Production TSLP can induce the naive myeloid dendritic cells (mDCs) to be matured and to secrete the chemokine thymus activation regulatory chemokine (TARC) and osteoprotegerin (OPG), thereby further mediating the innate and adaptive immune inflammatory response. This test example was used to verify that the obtained antibodies can block TSLP-induced chemokine production by mDCs, thereby blocking the occurrence of innate and adaptive inflammation response.

Figure 4A:
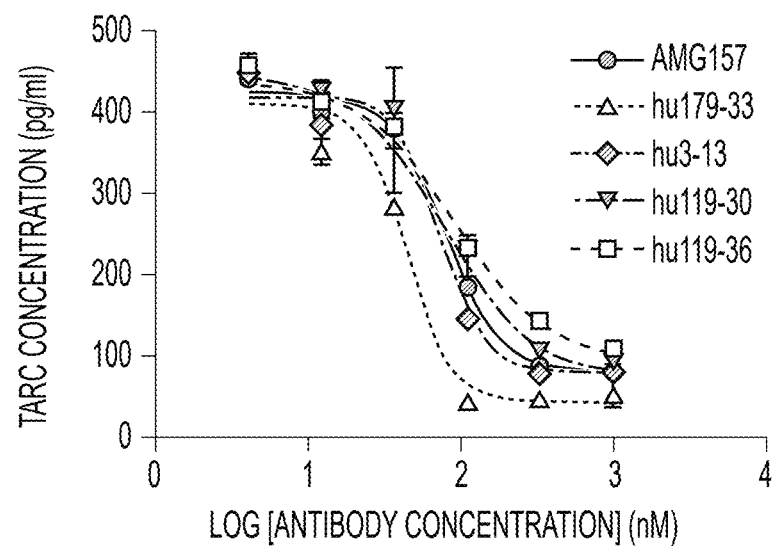
FIG. 4A shows the antibody activity of inhibiting the TSLP-induced production of the chemokine TARC.
Figure 4B:
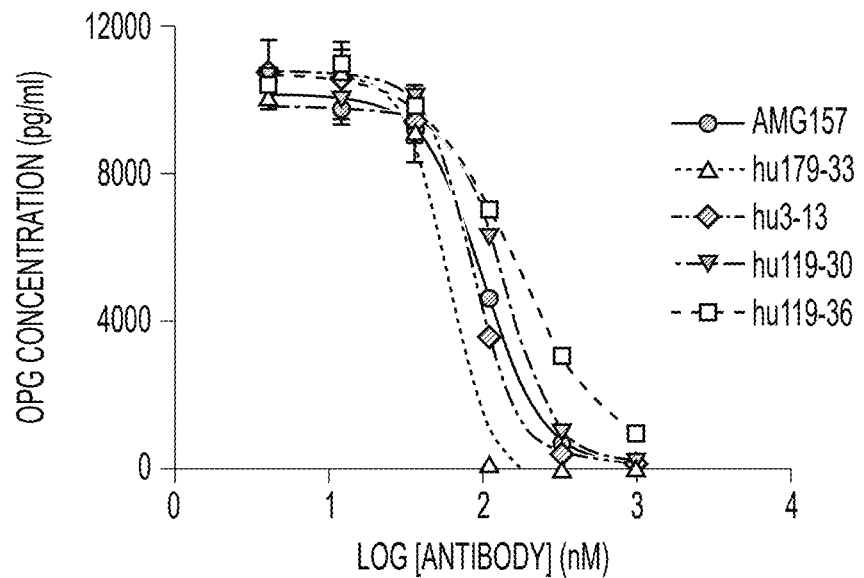
FIG. 4B shows the antibody activity of inhibiting the TSLP-induced production of the chemokine OPG.
Figure 5A:
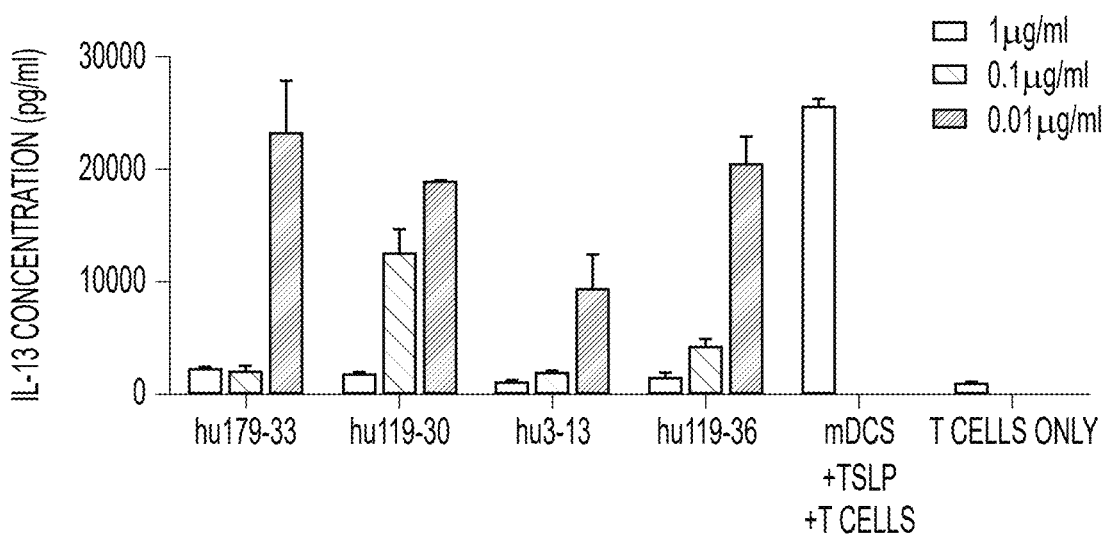
FIG. 5A shows the antibody activity of inhibiting the production of the Th2 cytokine IL-13.
Figure 5B:
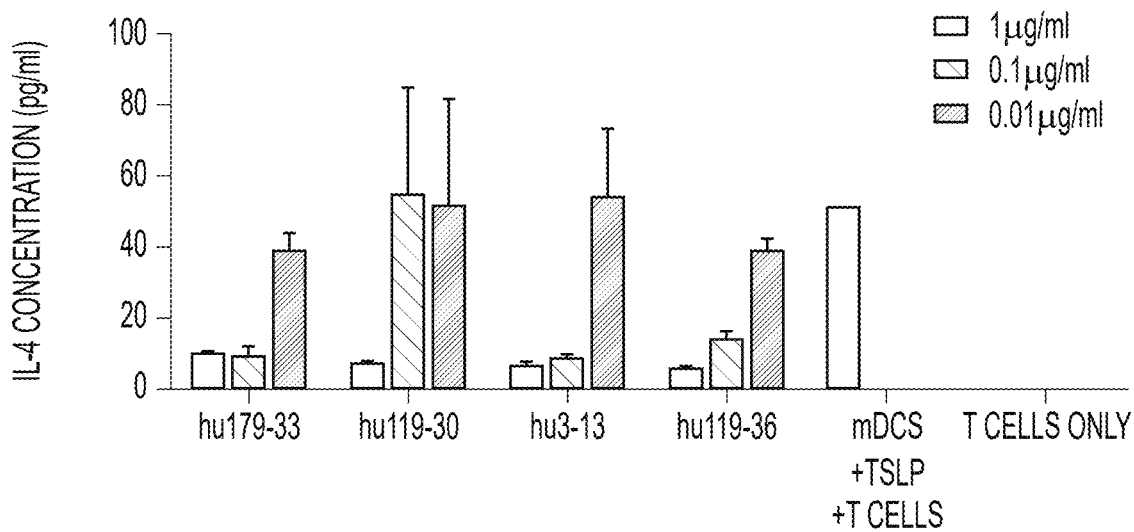
FIG. 5B shows the antibody activity of inhibiting the production of the Th2 cytokine IL-4.
Figure 5C:
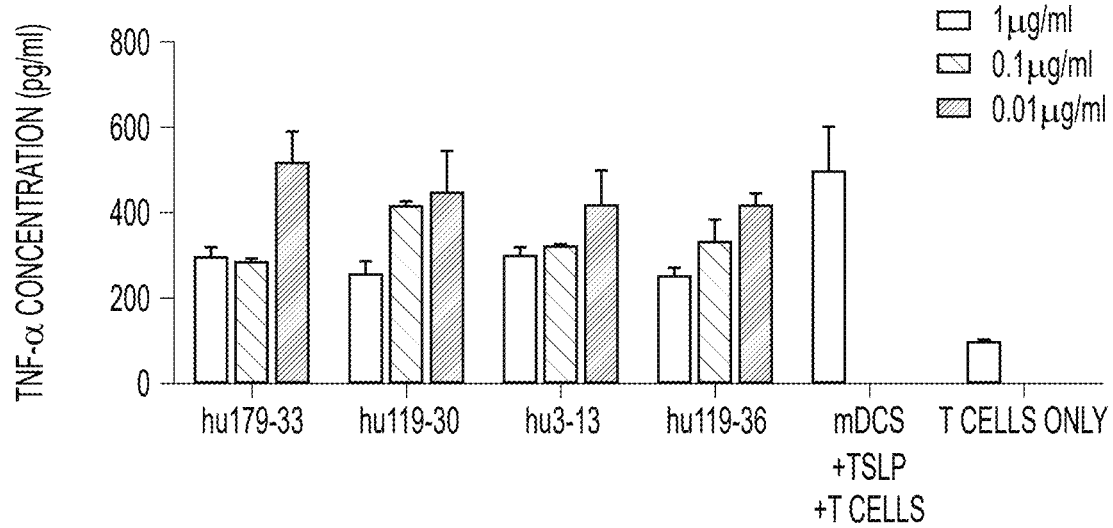
FIG. 5C shows the antibody activity of inhibiting the production of the Th2 cytokine TNF-α.
Figure 5D:
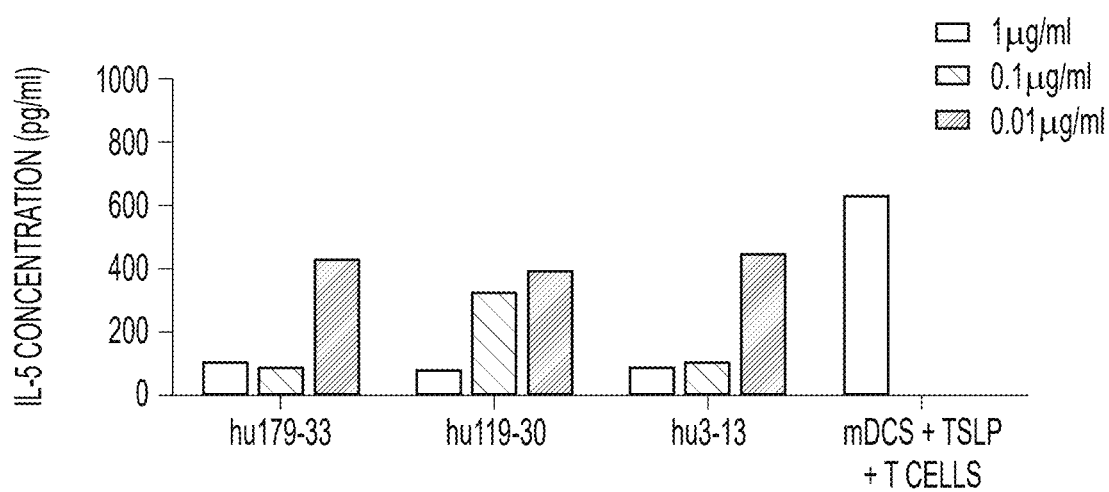
FIG. 5D shows the antibody activity of inhibiting the production of the Th2 cytokine IL-5.

Naive myeloid mDCs were separated and purified from human peripheral blood mononuclear cells (PBMCs) by using magnetic bead sorting method (CD1c (BDCA-1)+ Dendritic Cell Isolation Kit, Miltenyi Biotec). The obtained mDCs were seeded in 96-well cell culture plates. Serially diluted antibody samples and human TSLP (huTSLP-his, final concentration of 50 ng/ml) were pre-incubated for about 45 minutes (37° C.) and then respectively added to each cell culture well containing mDCs to stimulate mDCs in vitro. The plates were placed in an incubator to culture for 48 hours. The cell culture supernatant was collected and diluted properly, and then the chemokine content therein was detected by using ELISA method. TARC was detected by using human CCL17/TARC Quantikine ELISA Kit from R&D Company; OPG content was detected by using human CCL22/MDC Quantikine ELISA Kit (R&D), and the results are shown in FIG. 4A-FIG. 4B.

The results showed that all the antibodies in the present disclosure can significantly inhibit TSLP-induced TARC and OPG chemokine production, indicating that the antibodies in the present disclosure can block the occurrence of innate and adaptive inflammatory response.

Test Example 7. Anti-TSLP Antibodies Blocked the Proliferation of BaF3-TLSPR/IL7R Cells Induced by Native TSLP BaF3-hTSLPR/hIL7R cells can proliferate under the stimulation of native TSLP. Binding of antibodies to native TSLP reduces the stimulatory effect of TSLP on BaF3-hTSLPR/hTL7R cells.

NHLF cells (BeNa Culture Collection BNCC340764) and HLF1 cells (BeNa Culture Collection BNCC337730) were cultured until the cells grew to 80%, and the supernatant was discarded. Human lung fibroblasts, NHLF (BeNa Culture Collection BNCC340764) and HLF1 (BeNa Culture Collection BNCC337730), were stimulated with 10 ng/ml human IL1-β (Sino Biological GMP-10139-HNAE), 20 ng/ml IL13 (R&D 213-ILB-005), 20 ng/ml TNF-α (PEPRO-TECH 300-01A) for 72 hours to induce the production of native TSLP. After stimulation was over, the cell supernatant was collected and centrifuged at 4500 rpm for 5 min to remove cell debris. The supernatant was collected, concentrated for about 10 times by concentration columns, and filtered for later use.

BaF3-hTSLPR/hIL17R cells were cultured in RPMI1640 with 10% FBS (10 ng/mL mIL3, R&D 213-ILB-005), adjusted to a density of $1×10^4$ cells/ml and cultured in a 37° C., 5% $CO_2$ incubator to Logarithmic growth phase. The cells were collected, centrifuged at 800 rpm/min for 5 min, and the supernatant was discarded; the cells were washed with PBS for three times to remove the cytokines that stimulate their proliferation in the culture medium. The cells were resuspended in RPMI1640 medium with 4% FBS, seeded into 96-well plates at 4000 cells/50 μl/well and cultured in an incubator for 2 h. The antibodies to be tested was serially diluted by using native TSLP at 10-fold ratio, with an initial antibody concentration of 100 nM, resulting in 3 dilution gradients, 100 nM, 10 nM and 1 nM. 50 μl/well of the diluted antibody/antigen mixture was added to the cells with the final antibody concentration of 50 nM, 5 nM, 0.5 nM. The plates were incubated in a 37° C., 5% $CO_2$ incubator for 72 h. Then 30 μL CellTiter-Glo (Promega) was added to each well and incubated in the dark at room temperature for 10 min, and detected by using the Luminescence program with Cytation5 cell imager. The results are shown in the following table.

TABLE 39

| Results of anti-TSLP antibodies inhibiting the proliferation of BaF3-TLSPR/IL7R cells | | | | |
|---|---|---|---|---|
| Antibody | AMG157 | hu179-33 | hu3-13 | hu119-30 |
| IC50 (nM) | 3.379 | 0.02279 | 0.2888 | 1.533 |

The results showed that all the antibodies obtained in the present disclosure can significantly inhibit the activity of native TSLP to stimulate the proliferation of BaF3, especially hu179-33, the activity of which was more than 100 times of that of AMG157.

Test Example 8: Experiment of Anti-TSLP Antibodies Inhibiting TSLP-Induced Proliferation of BaF3 Cells Overexpressing TSLPR/IL7R TSLP can bind to TSLPR/IL7R on the surface of BaF3, thereby promoting the proliferation of BaF3. This test example was used to identify whether the antibodies of the present disclosure can block the activity of TSLP to induce the proliferation of BaF3.

Figure 3:
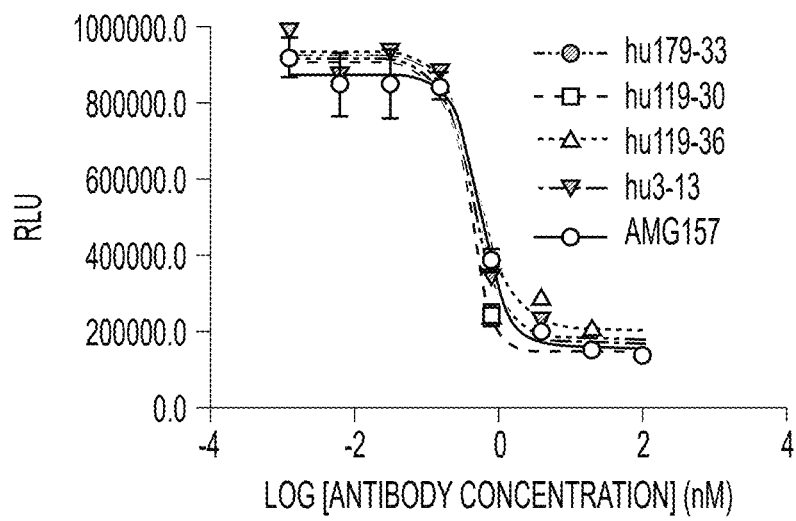
FIG. 3: The antibody inhibits TSLP-induced proliferation activity of BaF3 cells.

Specifically, BaF3 cells overexpressing TSLPR/IL7R were cultured in RPMI1640 with 10% FBS and 2 ng/mL rhIL3 (MultiSciences, Catalog No. 96-AF-300-03-20), cultured in a 37° C., 5% $CO_2$ incubator, with the cell density not exceeding $1×10^6$ cells/ml. When detecting the antibodies, cells in logarithmic growth phase were washed with PBS for three times and centrifuged at 800 rpm for 5 min. The cell density was adjusted to 8000 cells/well/90 μl with RPMI1640 (2% FBS, recombinant human TSLP-Fc: 40 ng/ml). 10 μl of serially diluted antibody to be tested was added to the 96-well plates and cultured for 2 days. 30 μl cell titer was added and mixed for detection. IC50 was calculated according to the reading. The results are shown in Table 40 and FIG. 3.

TABLE 40

Inhibition of the proliferation activity of BaF3 cells by antibodies

| Antibody | AMG157 | hu179-33 | hu119-30 | hu3-13 | hu199-36 |
|---|---|---|---|---|---|
| IC50 (nM) | 0.5730 | 0.4092 | 0.4305 | 0.4436 | 0.4760 |

The results showed that all the antibodies of the present disclosure have relatively strong ability to inhibit TSLP-mediated proliferation of BaF3 cells.

Test Example 9: Humanized Anti-TSLP Antibodies Blocked TSLP-Induced Differentiation of Native CD4+ T Cells into Th2 Cells TSLP can induce the maturation of primary myeloid mDC cells. Mature mDC cells highly express OX40 ligand, which can bind to OX40 on the surface of native CD4+ T cells, thereby differentiating the native CD4+ T into Th2 cells, which produce factors related to immune response such as IL4/IL5/IL13, etc., leading to Th2 inflammatory response in the body. This test example was used to detect whether the antibodies obtained in the present disclosure can block TSLP-induced differentiation of Th2 cells.

Naive myeloid DCs were separated and purified from human peripheral blood mononuclear cells (PBMCs) by using magnetic bead sorting method (CD1c (BDCA-1)+ Dendritic Cell Isolation Kit, Miltenyi Biotec). The obtained mDCs were seeded in 96-well cell culture plates. Serially diluted antibody samples and recombinant expressed human TSLP (huTSLP-his, final concentration 50 ng/ml) were pre-incubated (37° C.) for about 45 minutes and then respectively added to each cell culture well containing mDCs and cultured at 37° C. for 24 hours. The mature mDCs after stimulation were collected and washed with PBS twice. CD4+CD45RA+ native T cells were extracted from PBMCs by magnetic bead separation method (Myltenyi, Biotec). The native T cells obtained by separation and the mature mDCs were mixed and seeded in 96-well cell culture plates at a ratio of 5:1, and co-cultured for 6 days. The cells were collected and seeded in 96-well plates pre-coated with anti-CD3 (10 μg/ml), and anti-CD28 (1 μg/mL) was added to stimulate the differentiated T cells again. The cells were cultured for 24 hours and finally the cell culture supernatant was collected. Th2-related cytokines secreted by cells in the supernatant were detected by ELISA. TL-4 and IL-5 cytokines were detected by ELISA kits from R&D, and TNF-α and IL-13 were detected by ELISA kits from NeoBioscience. The results are shown in FIG. 5A-FIG. 5D.

The results showed that the antibodies obtained in the present disclosure can significantly inhibit the production of Th2 cytokines IL4, IL5, IL13 and TNF-α, indicating that the antibodies obtained in the present disclosure can block TSLP-induced differentiation of Th2 cells.

What is claimed is:

1. A method for treating a human patient having a TSLP-related disease, the method comprising administering to the human patient a therapeutically effective amount of an anti-TSLP antibody comprising:
   (i) a heavy chain variable region comprising HCDR1, HCDR2 and HCDR3 as shown in SEQ ID NO: 26, SEQ ID NO: 94 and SEQ ID NO: 28, respectively; and,
   (ii) a light chain variable region comprising LCDR1, LCDR2 and LCDR3 as shown in SEQ ID NO: 29, SEQ ID NO: 113 and SEQ ID NO: 31, respectively;
   wherein the TSLP-related disease is asthma, or nasal polyposis.

2. The method of claim 1, wherein the anti-TSLP antibody further comprises a heavy chain variable region comprising the sequence of SEQ ID NO: 97, and a amino acid sequence of the light chain variable region comprising the sequence of SEQ ID NO: 119.

3. The method of claim 2, wherein the anti-TSLP antibody further comprises an antibody heavy chain constant region and a light chain constant region; wherein the heavy chain constant region is selected from the group consisting of human IgG1, IgG2, IgG3 and IgG4 constant regions; and wherein the light chain constant region is selected from the group consisting of human antibody κ (kappa), human antibody λ (lambda) chain constant regions.

4. The method of claim 3, wherein the anti-TSLP antibody further comprises a heavy chain constant region as shown in SEQ ID NO: 133, and a light chain constant region as shown in SEQ ID NO: 134.

5. The method of claim 4, wherein the anti-TSLP antibody further comprises a heavy chain region as shown in SEQ ID NO: 139, and a light chain region as shown in SEQ ID NO: 140.

6. A method for treating asthma in a human patient comprising administering a therapeutically effective amount of an anti-TSLP antibody comprising (i) a heavy chain variable region that comprises HCDR1, HCDR2 and HCDR3 as shown in SEQ ID NO: 26, SEQ ID NO: 94 and SEQ ID NO: 28, respectively; and, (ii) a light chain variable region that comprises LCDR1, LCDR2 and LCDR3 as shown in SEQ ID NO: 29, SEQ ID NO: 113 and SEQ ID NO: 31, respectively.

7. A method for treating nasal polyposis in a human patient comprising administering a therapeutically effective amount of an anti-TSLP antibody comprising (i) a heavy chain variable region that comprises HCDR1, HCDR2 and HCDR3 as shown in SEQ ID NO: 26, SEQ ID NO: 94 and SEQ ID NO: 28, respectively; and, (ii) a light chain variable region that comprises LCDR1, LCDR2 and LCDR3 as shown in SEQ ID NO: 29, SEQ ID NO: 113 and SEQ ID NO: 31, respectively.

8. A method for treating asthma in a human patient comprising administering a therapeutically effective amount of an anti-TSLP antibody comprising a heavy chain variable region as shown in SEQ ID NO: 97, and a light chain variable region as shown in SEQ ID NO: 119.

9. A method for treating nasal polyposis in a human patient comprising administering a therapeutically effective amount of an anti-TSLP antibody comprising a heavy chain variable region as shown in SEQ ID NO: 97, and a light chain variable region as shown in SEQ ID NO: 119.

* * * * *